(12) United States Patent
Fraley et al.

(10) Patent No.: US 8,334,139 B1
(45) Date of Patent: Dec. 18, 2012

(54) PLASMIDS FOR TRANSFORMING PLANT CELLS

(75) Inventors: Robert T. Fraley, Glendale, MO (US); Stephen G. Rogers, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 06/783,336

(22) Filed: Oct. 4, 1985

Related U.S. Application Data

(63) Continuation of application No. 06/458,411, filed on Jan. 17, 1983, now abandoned, and a continuation-in-part of application No. 06/458,414, filed on Jan. 17, 1983, now abandoned.

(51) Int. Cl.
  *C12N 15/84* (2006.01)
  *C12N 15/54* (2006.01)
  *C12N 1/20* (2006.01)
  *C12N 1/21* (2006.01)

(52) U.S. Cl. ............... 435/469; 435/194; 435/252.2; 435/252.33; 435/320.1

(58) Field of Classification Search .......... 435/172, 435/253, 172.3, 317, 30, 52; 935/30, 35
  See application file for complete search history.

(56) References Cited

U.S. PATENT DOCUMENTS

| | | | | |
|---|---|---|---|---|
| 4,237,224 | A * | 12/1980 | Cohen et al. ............... | 435/172 |
| 4,407,956 | A | 10/1983 | Howell | |
| 4,459,355 | A | 7/1984 | Cello | |
| 4,536,475 | A * | 8/1985 | Anderson ............... | 435/172.3 |
| 4,652,525 | A * | 3/1987 | Rutter et al. ............ | 435/252.33 |
| 4,762,785 | A | 8/1988 | Comai | |
| 4,886,753 | A | 12/1989 | Marcker et al. | |
| 5,034,322 | A * | 7/1991 | Rogers et al. ............ | 435/252.2 |
| 5,106,739 | A * | 4/1992 | Comai et al. ............... | 800/294 |
| 5,352,605 | A * | 10/1994 | Fraley et al. ............... | 435/418 |
| 5,530,196 | A | 6/1996 | Fraley et al. | |
| 6,051,757 | A | 4/2000 | Barton et al. | |
| 6,174,724 | B1 | 1/2001 | Rogers et al. | |

FOREIGN PATENT DOCUMENTS

| | | |
|---|---|---|
| CA | 1169793 | 6/1984 |
| EP | 0 027 662 | 4/1981 |
| EP | 0 067 553 | 12/1982 |
| EP | 0067553 | 12/1982 |
| EP | 0 122 791 | 4/1983 |
| EP | 0 086 537 | 8/1983 |
| EP | 0086537 | 8/1983 |
| EP | 83 10 0255 | 11/1983 |
| EP | 0 131 623 | 1/1984 |
| EP | 0 116 718 | 8/1984 |
| EP | 0 290 799 A2 | 11/1988 |
| EP | 0 142 924 B1 | 4/1992 |
| FR | 2500847 | 9/1985 |
| WO | WO 82/03087 | 9/1982 |
| WO | 8301176 | 4/1983 |
| WO | WO 83/01176 | 4/1983 |
| WO | WO 84/02913 | 8/1984 |

OTHER PUBLICATIONS

Matzke et al, J. Mol. Appl. Gen. vol. 1 pp. 39-49 (1981).*
De Greve et al, Nature vol. 300 pp. 752-754 Dec. 1982.*
Otten et al, Mol. Gen. Genet. vol. 183 pp. 209-213 (1981).*
Chilton et al, Nature vol. 295 pp. 432-434.*
White et al, PNAS USA vol. 79 pp. 3193-3197 May 1982.*
Derwent Abstract of Patent Publication WP8301176-K16 (1983).*
Dewent Abstract of Patent Publication EP-67553-K01 (1983).*
Dewent Abstract of Patent Publication EP-27662-D19 (1981).*
Chemical Abstracts of French patent 2500847 1982.*
Zamboyski et al, J. Molecular and Applied Genetics vol. 1 pp. 361-370 (1982).*
Schell et al, Genetic Engineering to Biotechnology—The Critical Transition, John Wiley & Sons Ltd. pp. 41-53, Proceedings of a Symposium in Rome Italy Sep. 20-23, 1981.*
Simpson et al, Cell vol. 29 pp. 1005-1014 Jul. 1982.*
Thomoshow et al, Cell vol. 19 pp. 729-739 Mar. 1980.*
Depicker et al, Journal of Molecular and Applied Genetics vol. 1 pp. 561-573.*
Chilton, Genetic Engineering of Osmoregulation, Plenum. Publ. New York pp. 23-39 (1980).*
Leeman et al, Molecular Biology of Plant Tumors, Academy Press N. Y. pp. 537-545 (1982).*
Hoorykoss et al, Genetic Engineering Principle and Methods vol. 1, Plenum Press N.Y. pp. 151-179 (1979).*
Van Montogu et al, Current Topics in Microbiology and Immunology, vol. 96, Springer Verlag pp. 238-254 (1982).*
Leemans et al, J. Mol. Appl. Gen vol. 1 pp. 149-164 (1981).*

(Continued)

*Primary Examiner* — Anne Grunberg
(74) *Attorney, Agent, or Firm* — Marshall, Gerstein & Borun LLP

(57) ABSTRACT

This invention relates to several plasmids which are useful for genetically transforming plant cells. A first plasmid, such as pMON120, contains a T-DNA border, one or more marker genes, a unique cleavage site, and a region of Ti plasmid homology. A gene which is expressed in plant cells may be inserted into this plasmid to obtain a derivative plasmid, such as pMON128 which expresses neomycin phosphotransferase in plant cells. The derivative plasmid is inserted into a suitable microorganism, such as *A. tumefaciens* which contains a Ti plasmid. The inserted plasmids recombine with Ti plasmids to form co-integrate plasmids. Only a single crossover event is required to create the desired co-integrate plasmid. *A. tumefaciens* cells with co-integrate plasmids are selected and co-cultured with plant cells. The co-integrate Ti plasmids enter the plant cells and insert a segment of T-DNA which does not contain tumorigenic genes into the plant genome. The transformed plant cell(s) may be regenerated into a morphologically normal plant which will pass the inserted gene(s) to its descendants.

21 Claims, 37 Drawing Sheets

OTHER PUBLICATIONS

Schell et al, From Genetic Engineering to Biotechnology—The Critical Transistors, El. Whelon et al, Wiley & Sons Pub pp. 41-52 (May 21, 1982).*
Zambrogski et al, Journal of Molecular and Applied Genetics vol. 1 pp. 361-370 Jun. 1, 1982.*
Chilton et al, Stadler Symp. vol. 13 pp. 39-52 (1981).*
Depicker et al, Journal of Molecular and Applied Genetics vol. 1 pp. 561-573 Dec. 1, 1982.*
Ooms et al, Plasmid 1, 15-29 1982.*
Geraglty et al, Nucleic Acids Res. vol. 9 pp. 5163-5174 1981.*
Fitzgerald et al Cell vol. 24 pp. 251-260 Apr. 1981.*
Marx, J. Science 216: 1305 (Jun. 1982).*
Herrera-Estrella et al. Nature 303: 209-213 (May 1983).*
Barton et al. Cell 32: 1033-1043 (Apr. 1983).*
Gelvin, S. Plant Molecular Biology 8: 355-359 (1987).*
Bennetzen et al. Journal of Biological Chemistry 257(6): 3018-3025 (1982).*
Ellis et al. EMBO Journal 6(1): 11-16 (1987).*
Keith et al. EMBO Journal 5(10): 2419-2425 (1986).*
Llewellyn et al. pp. 593-607 In: Molecular Form and Function of the Plant Genome, van Vloten-Doting et al, eds., Plenum Publishing: New York (1985).*
Messing et al. pp. 211-227 In: Genetic Engineering of Plants, An Agricultural Perspective, Kosuge et al, eds., Plenum Press: New York (1983).*
Lewin, B., ed. pp. 174-194 In: Genes, John Wiley and Sons: New York (1983).*
Alberts et al, eds. pp. 406-408 In: Molecular Biology of the Cell, Garland Publishing: New York (1983).*
Wiborg et al. Nucleic Acids Research 10(11): 3487-3494 (1982).*
Brisson et al. Proc. Natl. Acad. Sci. USA 79: 4055-4059 (Jul. 1982).*
Franck et al. Cell 21: 285-294 (Aug. 1980).*
Gardner et al. Nucleic Acids Research 9(12): 2871-2888 (1981).*
Hu et al. EMBO Journal 1(11): 1337-1342 (1982).*
Kridl et al. Gene 28: 113-118 (1984).*
Depicker et al. Journal of Molecular and Applied Genetics 1(6): 561-573 (1982).*
Heidicker, G. Nucleic Acids Research 11(14): 4891-4906 (1983).*
Dunsmuir et al. Journal of Molecular and Applied Genetics 2(3): 285-300 (1983).*
Jones et al. EMBO Journal 4(10): 2411-2418 (1985).*
Guilley et al. Cell 30: 763-773 (Oct. 1982).*
Shaw et al. Nucleic Acids Research 12(20): 7831-7846 (1984).*
Schernthaner et al. EMBO Journal 7(5): 1249-1255 (1988).*
Matzke et al. EMBO Journal 3(7): 1525-1531 (1984).*
Sengupta-Gopalan et al. Proc. Natl. Acad. Sci. USA 82: 3320-3324 (1985).*
Murai et al. Science 222: 476-482 (1983).*
Herman et al. Molecular and Cellular Biology 6(12): 4486-4492 (Dec. 1986).*
Lamppa et al. Nature 316: 750-752 (1985).*
Nagy et al. EMBO Journal 4(12): 3063-3068 (1985).*
Schoffl et al. EMBO Journal 4(5): 1119-1124 (1985).*
Goldsbrough et al. Mol. Gen. Genet. 202: 374-381 (1986).*
Stougaard et al. Proc. Natl. Acad. Sci. USA 84: 5754-5757 (1987).*
Facciotti et al. Bio/Technology 3: 241-246 (1985).*
Kaulen et al. EMBO Journal 5(1): 1-8 (1986).*
Rosahl et al. EMBO Journal 6(5): 1155-1159 (1987).*
Colot et al. EMBO Journal 6(12): 3559-3564 (1987).*
A. Kleinhofs and R. Behki, "Prospects for Plant Genome Modification by Nonconventional Methods," *Ann. Rev. Genet. 1977* 11: 79-101 (1977).
Abstracts from "Advances in Gene Technology: Molecular Genetics Plants and Animals," 15th Miami Winter Symposium, Jan. 1983.
Barker et al., "Nucleotide sequence of the T-DNA region from the *Agrobacterium tumefaciens* Octopine Ti plasmid pTi15955", *Plant Molecular Biology*, 2:335-350 (1983).
Beachy et al., "Molecular characterization of a soybean variety lacking a subunit of the 7S seed storage protein", *Plant Molecular Biology*, Arco Solar-UCLA Symposium, Apr. 16-22, pp. 413-422 (1983).

Beachy et al., "Accumulation and assembly of soybean μ-coglycimin in seeds of transformed petunia plants", *EMBO J.*, 4(12):3047-3053 (1985).
Bedbrook et al., "Molecular cloning and sequencing of cDNA encoding the precursor to the small subunit of chloroplast ribulose-1,5-bisphosphate carboxylase", *Nature*, 287:692-697 (1980).
Bevan et al., "A chimaeric antibiotic resistance gene as a selectable marker for plant cell transformation", *Nature*, 304:184-187 (1983).
Brisson & Verma, "Soybean leghemoglobin gene family: Normal, pseudo, and truncated genes", *Proc. Natl. Acad. Sci. USA*, 79:4055-4059 (1982).
Brogile et al., "Structural analysis of nuclear genes coding for the precursor to the small subunit of wheat ribulose-1,5-bisphosphate carboxylase", *Bio/Technology*, 55-61 (1983).
Brogile et al., "Light-regulated expression of a pea ribulose-1,5-bisphosphate carboxylase small subunit gene in transformed plant cells", *Science*, 224:838-843 (1984).
Cairnes et al., "Translation of animal virus-RNA in the cytoplasm of a plant cell", *PNAS*, 75(11):5557-5559 (1978).
Cairns et al., "Expression of a DNA Animal Virus Genome in a Plant Cell", *FEBS Letters*, 96(2):295-297 (1978).
Chilton et al., "T-DNA from *Agrobacterium* Ti plasmid in the nuclear DNA fraction of crown gall tumor cells", *Proc. Natl. Acad. Sci. USA*, 77(7):4060-4064 (1977).
Chilton et al., "*Agrobacterium rhizogenes* inserts T-DNA into the genomes of the host plant root cells", *Nature*, 295:432-434 (1982).
Chilton et al., "Multiple Viral Specific Transcripts from the Genome of Cauliflower Mosaic Virus", Proceedings of the Miami Winter Symposium, Jan. 1983, published in *Advances in Gene Technology: Molecular Genetics of Plants and Animals* (Ahmad et al., eds.), p. 564 (1983).
Chilton et al., "Ti and Ri Plasmids as Vectors for Genetic Engineering of Higher Plants", Proceedings of the Miami Winter Symposium, Jan. 1983, published in *Advances in Gene Technology: Molecular Genetics of Plants and Animals* (Ahmad et al., eds.), pp. 14-15 (1983).
Cocking et al., "Aspects of plant genetic manipulation" *Nature*, 293:265-270 (1981).
Colbere-Garapin et al., "A New Dominant Hybrid Selective Marker for Higher Eukaryotic Cells", *J. Mol. Biol.*, 150-1-14 (1981).
Davey et al., "Transformation in plants: potential and reality", (Abstract of Conference paper from University of Nottingham) (1982).
DeGreve et al., "Nucleotide sequence and transcript map of the *Agrobacterium tumefaciens* Ti plasmid-encoded octopine synthase gene", *J. Mol. Appl. Genet.*, 1(6):499-511 (1982).
DeGreve et al., "Regeneration of normal and fertile plants that express octopine synthase, from tobacco crown galls after deletion of tumour-controlling functions", *Nature*, 300:752-754 (1982).
Depicker et al., "Plant Cell Transformation by *Agrobacterium* Plasmids", Proceedings of a symposium held Aug. 15-19, 1982 at the University of California, Davis published in *Genetic Engineering of Plants: An Agricultural Perspective, Basic Life Sciences* (Kosuge et al., eds. 1983), pp. 143-176 (1982).
Dix et al., "A Cell Line of *Nicotiana sylvestris* with Resistance to Kanamycin and Streptomycin", *Molec. Gen. Genet.*, 157:285-290 (1977).
Fischer et al., "Structure and flanking regions of soybean seed protein genes", *Cell*, 29:651-660 (1982).
Flavell et al., "Selectable marker genes: safe for plants?", *Bio/Technology*, 10:141-144 (1992).
Fraley et al., "Use of a Chimeric Gene to Confer Antibiotic Resistance to Plant Cells", Proceedings of the Miami Winter Symposium, Jan. 1983, published in *Advances in Gene Technology: Molecular Genetics of Plants and Animals* (Ahmad et al., eds.), pp. 211-221 (1983).
Franck et al., "Nucleotide sequence of cauliflower mosaic virus DNA", *Cell*, 21:285-294 (1980).
Gardner et al., "Plant Viral Vectors: CaMV As an Experimental Tool", Proceedings of a symposium held Aug. 15-19, 1982 at the University of California, Davis, published in Genetic Engineering of Plants: an Agricultural Perspective, Basic Life Sciences (Kosuge et al., eds. 1983), pp. 121-142 (1982).

Gardner et al., "The complete nucleotide sequence of an infectious clone of cauliflower mosaic virus by M13mp7 shotgun sequencing", *Nucleic Acids Res.*, 9:2871-2888 (1981).
Garfinkel et al., "Genetic Analysis of Crown Gall: Fine Structure Map of the T-DNA by Site-Directed Mutagenesis", *Cell*, 27:143-153 (1981).
Geraghty et al., "The primary structure of a plant storage protein: zein", *Nucl. Acids Res.*, 9(19):5163-5174 (1981).
Gerlach et al., "cDNA cloning and induction of the alcohol dehydrogenase gene (Adh1) of maize", *PNAS USA*, 79:2981-2985 (1982).
Gordon et al., "Current Developments in the Transformation of Plants", Proceedings of the Miami Winter Symposium, Jan. 1983, published in Advances in *Gene Technology: Molecular Genetics of Plants and Animals* (Ahmad et al., eds.) pp. 37-46 (1983).
Hall et al., "The Phaseolin Family of Seed Protein Genes: Sequences and Properties", published in *Advances in Gene Technology: Molecular Genetics of Plants and Animals*, (Ahmad et al., eds.), pp. 349-367 (1983).
Hernalsteens, "The *Agrobacterium tumefaciens* Ti plasmid as a host vector system for introducing foreign DNA in plant cells", *Nature*, 287:654-656 (1980).
Herrera-Estrella et al., "Chimeric genes as dominant selectable markers in plant cells", *EMBO J.*, 2:987-995 (1983).
Hohn et al., "Cauliflower Mosaic Virus on Its Way to Becoming a Useful Plant Vector", in *Current Topics in Microbiology and Immunology*, 96:193-236 (1982) (Henle et al., eds.).
Holster et al., "The Use of Selectable Markers for the Isolation of Plant-DNA/T-DNA Junction Fragments in a Cosmid Vector", *Molec. Gen. Genet.*, 185:283-289 (1982).
Howell et al., "Cloned Cauliflower Mosaic Virus DNA Infects Turnips (*Brassica rapa*)", *Science*, 208:1265-1267 (1980).
Hu et al., "Primary structure of a genomic zein sequence of maize", *EMBO J.*, 1:1337-1342 (1982).
Hyldig-Nielsen et al., "The primary structures of two leghemoglobin genes from soybean", *Nucleic Acids Res.*, 10(2):689-701 (1982).
Jimenez et al., "Expression of a transposable antibiotic resistance element in *Saccharomyces*", *Nature*, 287:869-871 (1980).
Kemp et al., "*Agrobacterium*-Mediated Transfer of Foreign Genes into Plants", in *Genetic Engineering: Application to Agriculture* (Owens, ed.), pp. 215-228 (1983).
Kim et al., "A 20 nucleotide upstream element is essential for the nopaline synthase (nos) promoter activity", *Plant Molecular Biology*, 24:105-117 (1994).
Kridl et al., "Nucleotide sequence analysis of a zein genomic clone with a short open reading frame", *Gene*, 28:113-118 (1984).
Lebeurier et al., "Infectivities of native and cloned DNA of cauliflower mosaic virus", *Gene*, 12:139-146 (1980).
Lee et al., "Control of tuber protein synthesis in potato", *Plant Molecular Biology*, Arco Solar-UCLA Symposium, Apr. 16-22, 1983, pp. 355-365.
Leemans, Universite Libre de Bruxelles, Thesis, 1-25; 114-125 (1982).
Leemans et al., "Site-Specific Mutagenesis of *Agrobacterium* Ti Plasmids and Transfer of Genes to Plant Cells", *J. Molec. Appl. Genet.*, 1(2):149-164 (1981).
Leemans et al., "Genetic identification of functions of TL-DNA transcripts in octopine crown galls", *EMBO J.*, 1(1):147-152 (1982).
Leemans, "Ti to tomato, tomato to marker", *Bio/Technology*, 11:S22-S26 (1993).
Liu et al., "*Agrobacterium* Ti plasmid indoleacetic acid gene is required for crown gall oncogenesis", *Proc. Natl. Acad. Sci. USA*, 79:2812-2816 (1982).
Maliga et al., "Restoration of Morphogenic Potential in *Nicotiana* by Somatic Hybridisation", *Molec. Gen. Genet.*, 157:291-296 (1977).
Marks et al., "Molecular Structure and Expression of Maize Zein Genes", published in *Advances in Gene Technology: Molecular Genetics of Plants and Animals*, pp. 369-381 (1983).
Matzke et al., "Site-Specific Insertion of Genes into T-DNA of the *Agrobacterium* Tumor-Inducing Plasmid: An Approach to Genetic Engineering of Higher Plant Cells" *J. Molec. Appl. Genet.*, 1:39-49 (1981).

Matzke et al., "Transcription of a zein gene introduced into sunflower using a Ti plasmid vector", *EMBO J.*, 3:1525-1531 (1984).
McKnight et al., "Isolation of Mapping of Small Cauliflower Mosaic Virus DNA Fragments Active as Promoters in *Escherichia coli*", *J. Virol.*, 37(2):673-682 (1981).
Meagher et al., "Plant actin is encoded by diverse multigene families", *Advances in Gene Technology: Molecular Genetics of Plants and Animals*, Miami Winter Symposia, 20:171-187.
Meagher et al., "A Model for a Molecular Cloning System in Higher Plants: Isolation of Plant Viral Promotors", *NATO Advance Study Institute Series*, 29:63-75 (1980).
Messing et al., Proceedings of a symposium held Aug. 15-19, 1982 at the University of California, Davis published in *Genetic Engineering of Plants: An Agricultural Perspective, Basic Life Sciences*, 26:211-227 (Kosuge et al., eds. 1983) (1982).
Messing et al., "Plant gene structure", Proceedings of Symposium held Aug. 15-19, 1982 at the University of California, Davis, published in *Basic Life Sciences*, 26:211-227 (1983).
Messing, Joachim, Expert Opinion for presenting to the European Patent Office in the Opposition Appeal Proceedings T 0387/94-334 (corresponding European Patent Aplication) (1997).
Mulligan et al., "Synthesis of rabbit β-globin in cultured monkey kidney cells following infection with a SV40 β-globin recombinant genome" *Nature*, 277:108-114 (1979).
Mulligan et al., "Expression of a Bacterial Gene in Mammalian Cells", *Science*, 209:1422-1427.
Mulligan et al., "Selection for animal cells that express that *Escherichia coli* gene coding for xanthine-guanine phosphoribosyltransferase", *Proc. Natl. Acad. Sci. USA*, 75(4):2072-2076 (1981).
Murai et al., "Phaseolin gene from bean is expressed after transfer to sunflower via tumor-inducing plasmid vectors", *Science*, 222:476-482 (1983).
O'Hare et al., "Transformation of mouse fibroblasts to methotrexate resistance by a recombinant plasmid expression a prokaryotic dihydrofolate reductase", *PNAS*, 78(3):1527-1531 (1981).
Old et al., *Principles of Gene Manipulation: An Introduction to Genetic Engineering*, 1st ed.(Carr et al., eds.) University of California Press, vol. 2, pp. 9-23 (1980).
Old et al., *Principles of Gene Manipulation: An Introduction to Genetic Engineering*, 2nd ed.(Carr et al., eds.), University of California Press, vol. 2, pp. 121-210 (1981).
Olszewski et al., "A Transcriptionally Active, Covalently Closed Minichromosome of Cauliflower Mosaic Virus DNA Isolated from Infected Turnip Leaves", *Cell*, 29:395-402 (1982).
Otten et al., "Mendelian Transmission of Genes Introduced into Plants by the Ti Plasmids of *Agrobacterium tumefaciens*", *Molec. Gen. Genet.*, 183:209-213 (1981).
Peacock et al., "Gene transfer in maize: controlling elements and the alcohol . . . ", *Advances in Gene Technology: Molecular Genetics of Plants and Animals*, Miami Winter Symposia, vol. 20, pp. 311-325 (1983).
Pedersen et al., "Cloning and sequence analysis reveal structural variation among related zein genes in maize", *Cell*, 29:1015-1026 (1982).
Portetelle et al., *Annales De Gembloux*, 87e annee; 3e trimestre, No. 3:101-123 (1981).
Schell et al., Abstract of "Transfer of genes into plants via the Ti-plasmid of *Agrobacterium tumifaciens*", Proceedings of a conference held Jul. 3-7, 1978 in Wageningen, Netherlands, published in *Broadening the Genetic Base of Crops* (Harten et al., eds.), pp. 255-276 (1979).
Schell et al., Abstract of "Plant cell transformation and genetic engineering", published in *Plant Improvement and Somatic Cell Genetics* (Vasil et al., eds.), Academic Press, NY, pp. 255-276 (1982).
Schell et al., "The Ti Plasmids as Natural and as Practical Gene Vectors for Plants", *Bio/Technology*, Apr. 1983, pp. 175-180 (1983).
Schell et al., "Ti Plasmids as Experimental Gene Vectors for Plants", Proceedings of the Miami Winter Symposium, Jan. 1983, published in *Advances in Gene Technology: Molecular Genetics of Plants and Animals* (Ahmad et al., eds.), pp. 191-209 (1983).

Schoffl et al., "An analysis of mRNAs for a group of heat shock proteins of soybean using cloned cDNAs", *J. Mol. Appl. Genet.*, 1:301-314 (1982).

Schroeder et al., "Ti-Plasmids: Genetic Engineering of Plants", in *Plant Cell Culture in Crop Improvement* (Sen et al., eds.), Plenum Press, NY, pp. 287-297 (1983).

Shah et al., "Complete nucleotide sequence of a soybean actin gene", *Proc. Natl. Acad. Sci. USA*, 79:1022-1026 (1982).

Slightom et al., "Complete nucleotide sequence of a French bean storage protein gene: Phaseolin", *PNAS USA*, 80:1897-1901 (1983).

Sun et al., "Intervening sequences in a plant gene-comparison of the partial sequence of cDNA and genomic DNA of French bean phaseolin", *Nature*, 289:37-41 (1981).

Timko et al., "Nuclear genes encoding the constituent polypeptides of the light-harvesting chlorophyll A/B-protein complex . . . ", *Plant Molecular Biology*, Arco Solar-UCLA Symposium, Apr. 16-22, 1983, pp. 403-412.

Ursic et al., "A New Antibiotic With Known Resistance Factors, G418, Inhibits Plant Cells", *Biochem. Biophys. Res. Commun.*, 101(3):1031-1037 (1981).

Velten et al., "$T_R$ genes involved in agropine production", *Molecular Genetics of the Bacteria-Plant Interaction*, Verlag, Berlin, Puhler, A. (ed.), pp. 303-312 (1983).

Watson, *Molecular Biology of the Gene*, 3rd ed., W.A. Benjamin, Inc., Menlo Park, California, pp. 379-495 (1977).

Wiborg et al., "The nucleotide sequences of two leghemoglobin genes from soybean", *Nucleic Acids Res.*, 10:3487-3494 (1982).

Willmitzer et al., "DNA from Ti plasmid present in nucleus and absent from plastids of crown gall plant cells", *Nature*, 287:359-361 (1980) (Nov. 1992).

Willmitzer et al., "The TL-DNA in octopine crown-gall tumours codes for seven well-defined polyadenylated transcripts", *EMBO J.*, 1(1):139-146 (1982).

Wimpee et al., "Sequence heterogeneity in the RuBP carboxylase small subunit gene family of *Lemna gibba*", *Plant Molecular Biology*, Arco Solar-UCLA Symposium, Apr. 16-22, 1983, pp. 391-401.

Mar. 7, 1997 Decision of the Technical Board of Appeal 3.3.4. In the Opposition Appeal Proceedings T 0387/94-334 of corresponding European Patent Application No. 84900782.8-2106/0131623.

Nov. 3, 1994 Interlocutory Decision of the Opposition Division in the Opposition Proceedings of corresponding European Patent Application No. 84900782.8-2105/0131623.

Notice of Opposition of Max-Planck-Gesellschaft zur in the Opposition Proceedings of corresponding European Patent Application No. 84900782.8-2105/0131623. (Jun. 1991).

Notice of Opposition of ICI Seeds in the Opposition Proceedings of corresponding European Patent Application No. 84900782.8-2105/0131623, (Jun. 1991).

Notice of Opposition of Pioneer Hi-Bred International, Inc. in the Opposition Proceedings of corresponding European Patent Application No. 84900782.8-2105/0131623, (Jun. 1991).

Notice of Opposition of BIOCEM in the Opposition Proceedings of corresponding European Patent Application No. 84900782.8-2105/0131623, (Jun. 1991).

Notice of Opposition of Unilever PLC in the Opposition Proceedings of corresponding European Patent Application No. 84900782.8-2105/0131623, (Jun. 1991).

Notice of Opposition of Agricultural Genetics Co. Ltd. in the Opposition Proceedings of corresponding European Patent Application No. 84900782.8-2105/0131623, (Jun. 1991).

Notice of Opposition of Mogen International N.V. in the Opposition Proceedings of corresponding European Patent Application No. 84900782.8-2105/0131623, (Jun. 1991).

First Response of Monsanto Company to Opponents Notices of Opposition in the Opposition Proceedings of corresponding European Patent Application No. 84900782.8-2105/0131623, Nov. 1992.

Beringer et al, "Transfer of the drug resistance transposon Tn 5 to Rhizobium", *Nature* 276:633-634 (Dec. 7, 1978).

Abstract by M.D. Chilton et al (p. 14-15), from "Advances in Gene Technology: Molecular Genetics of Plants and Animals" distributed to attendees at the fifteenth Miami Winter Symposium, Jan. 17-21, 1983. (Oral presentation corresponding to patent made on Jan. 18, 1983).

M.D. Chilton et al, "Tailoring the *Agrobacterium* Ti Plasmid as a Vector for Plan Genetic Engineering", Stadler Symposium (U. of Mo., Columbia) 13: 39-52 (1981).

M.D. Chilton, "*Agrobacterium* Ti Plasmid as Tool for Genetic Engineering in Plants" p. 23, in Genetic Engineering of Osmoregulation, edited by D.W. Rains et al (Plenum Publ., NY 1980).

Depicker et al, "Nopaline Synthase: Transcript Mapping and DNA Sequence", *Journal of Molecular and Applied Genetics* 1:561-573 (1982).

Fitzgerald et al, "The Sequence of 5"-AAUAAA-3" Forms Part of the Recognition Site for Polyadenylation of Late SV40 mRNAs", *Cell* 24:251-260 (Apr. 1981).

J. L. Fox, "Plant molecular biology beginning to flourish", *Chemical and Engineering News*, pp. 33-44 (Jun. 22, 1981).

Fraley et al, *Proceedings of the National Academy of Science of the USA*, 80(15): 4803-4807 (Aug. 1983).

P. J. J. Hooykaas et al, "*Agrobacterium* Tumor Inducing Plasmids: Potential Vectors for the Genetics Engineering of Plants" *Genetic Enqnq Principles and Methods*, 1:151 edited by J.K. Setlow and A. Hollaender (Plenum Press, NY, 1979).

Kleinhofs and Behki, "Prospects for Plant Genome Modification by Non-Conventional Methods", *Ann. Rev. Genet.* 11: 79-101 (1977).

J. Leemans et al, "Ti Plasmids and Directed Genetic Engineering" in Molecular Biology of Plant Tumors, G. Kahl and J. Schell (eds.) pp. 537-545 (Academic Press NY 1982).

Ooms et al, "Octopine Ti-Plasmid Deletion Mutants of Agrobacterium tumefaciens with Emphasis on the Right Side of the T-Region", *Plasmids*, 7:15-29 (1982).

Ream et al, "Crown gall disease and prospects for genetic manipulation in plants", *Science*, 218:854-859 (Nov. 26, 1982).

J. Schell et al, Abstract from "Advances in Gene Technology: Molecular Genetics of Plants and Animals" distributed to attendees at the fifteenth Miami Winter Symposium, Jan. 17-21, 1983. (Oral presentation corresponding to patent made on Jan. 18, 1983).

Schell et al, "The Use of Ti Plasmids as Gene Vectors for Plants", *Genetic Engineering to Biotechnology—The Critical Transition*, p. 41-53 (1982), Proceedings of a symposium in Rome, Italy Sep. 20-23, 1981.

Simpson et al, "DNA from the A6S/2 Crown Gall Tumor Contains Scrambled Ti-Plasmid Sequences near It Junctions with Plant DNA", *Cell*, 29:1005-1014 (1982).

Thomashow et al, "Integration and Organizaion of Ti Plasmid Sequence n Crown Gall Tumors" *Cell*, 19:729-739 (1980).

M. Van Montagu & J. Schell, "The Ti Plasmids of *Agrobacterium*", *Current Topics in Microbiology and Immunology*, 96:237-254 (1982).

F. White et al, "Tumor induction of *Agrobacterium rhizogenes* involves the transfer of plasmid DNA to the plant genome," *Proc. Natl. Acad. Sci. USA*, 79:3193-3197 (1982).

Zambryski et al, "Tumor Induction by *Agrobacterium tumefacians*: Analysis of Boundaries of T-DNA", *J. Molecular and Applied Genetics* 1:361-370 (1982).

Comai et al, *Chemical Abstracts*, 99:182, abstract 100292j (Sep. 26, 1983).

J.D. Kemp et al, *Chemical Abstracts*, 101:176, abstract 18452n (Jul. 3, 1984).

VanSlogteron et al, *Chemical Abstracts*, 97: 182, abstract 139517v (Oct. 25, 1982).

P.M. Gresshoff, "Growth Inhibition by Glyphosate and Reversal of its Action by Phenylalanine and Tyrosine", *Aust. J. Plant Physiol.*, 6, 177-85 (1979).

Comai et al, "An Altered aroA Gene Product Confers Resistance to the Herbicide Glyphosate", *Science*, vol. 221, pp. 370-371 (Jul. 22, 1983).

Holländer et al, "The Site of the Inhibition of the Shikimate Pathway by Glyphosate" *Plant Physiol.*, 66, 823-829 (1980).

Comai et al, "Expression in plants of a mutant aroA gene from *Salmonella typhimurium*, confers tolerance to glyphosate", *Nature*, vol. 317, pp. 741-744 (Oct. 24, 1985).

Stalker et al., "A Single Amino Acid Substitution in the Enzyme 5-Enolpyruvylshikimate-3-phosphate Synthase Confers Resistance to the Herbicide Glyphosate", *The Journal of Biological Chemistry*, vol. 260, No. 8, pp. 4724-4728 (Apr. 25, 1985).

Schönbrunn et al, "Interaction of the herbicide glyphosate with its target enzyme 5-enolpyruvylshikimate 3-phosphate synthase in atomic detail", *PNAS*, vol. 98, No. 4, pp. 1376-1380 (Feb. 13, 2001).

Barton et al., "Regeneration of Intact Tobacco Plants Containing Full Length Copies of Genetically Engineered T-DNA, and Transmission of T-DNA to R1 Progeny", *Cell*, 32:1033-1043 (1983).

Herrera-Estrella et al., "Expression of chimaeric genes transferred into plant cells using a Ti-plasmid-derived vector", *Nature*, 303:209-213 (1983).

Marx, "Ti Plasmids as Gene Carriers: When suitably modified, tumor-inducing plasmids can transfer genes into plant cells from which normal plants may be regenerated", *Science*, 216:1305 (1982).

Barton et al., "Tobacco Plants Regenerated from Cells Transformed with an Engineered Ti Plasmid Contain the Gene Encoding Yeast Alcohol Dehydrogenase I", *N.A.T.O. FEBS conference*, Italy, p. 152, Aug. 23-Sep. 2, 1982.

Bevan et al., "Multiple Transcripts of T-DNA Detected in Nopaline Crown Gall Tumors", *Journal of Molecular and Applied Genetics*, 1(6):539-546 (1982).

Bevan et al., "T-DNA of the *Agrobacterium* Ti and Ri Plasmids", *Ann. Rev. Genet.*, 16:357-384 (1982).

Bohn et al., "Immunity to Fusarium Wilt in the Tomato", *Science*, 89(2322):603-604 (1939).

Chilton et al., "Cloning Vectors for Plant Genetic Engineering", *Plant Genetic Engineering*, (1993).

Dudits et al., "Plant Regeneration from Intergeneric Cell Hybrids", *Plant Science Letters*, 15:101-112 (1979).

Dudits et al., "Backfusion with Somatic Protoplasts as a Method in Genetic Manipulation of Plants", *Acta boil. Acad. Sci. hung.*, 32(3-4):215-218 (1981).

Gleba et al., "Arabidobrassica": A Novel Plant Obtained by Protoplast Fusion, *Planta*, 149:112-117 (1980).

Hoffmann et al., "Arabidobrassica": Chromosomal recombination and morphogenesis in asymmetric intergeneric hybrid cells, *Planta*, 153:586-593 (1981).

Komarnitsky et al., "Fraction I Protein Analysis of Parasexual Hybrid Plants *Arabidopsis thaliana* + *Brassica campestris*", *Plant Cell Reports*, 1:67-68 (1981).

Melchers et al., "Somatic Hybrid Plants of Potato and Tomato Regenerated from Fused Protoplasts", *Carlsberg Res. Commun.*, 43:203-218 (1978).

Newell et al., "Successful Wide Hybridization Between the Soybean and a Wild Perennial Relative, *G. tomentella* Hayata", *Crop Science*, 22:1062-1065 (1982).

Ooms et al., "Crown gall plant tumors of abnormal morphology, induced by *Agrobacterium tumefaciens* carrying mutated octopine Ti plasmids: analysis of T-DNA functions", *Gene*, 14:33-50 (1981).

Poulsen et al., "Peptide Mapping of the Ribulose Bisphosphate Carboxylase Small Subunit From the Somatic Hybrid of Tomato and Potato", *Carlsberg Res. Commun.*, 45:249-267 (1980).

Schiller et al., "Restriction Endonuclease Analysis of Plastid DNA from Tomato, Potato and Some of Their Somatic Hybrids", *Mol. Gen. Genet.*, 186:453-459 (1982).

Yang et al., "Revertant seedlings from crown gall tumors retain a portion of the bacterial Ti plasmid DNA sequences", *Proc. Natl. Acad. Sci. USA*, 78(7):4151-4155 (1981).

Ahmad, F. et al, "From gene to protein: translation into biotechnology" Miami Winter Symposium, vol. 19, 514 (1982).

Ammerer et al, "Recombinant DNA," Proceedings of the Third Cleveland Symposium on Macromolecules, 185-197 (1981).

Barton et al, "*Bacillus thuringiensis* δ-Endotoxin Expressed in Transgenic *Nicotiana tabacum* Provides Resistance to Lepidopteran Insects", *Plant Physiol*, 85:1103-1109 (1987).

Beck et al, "Nucleotide sequence and exact localization of the neomycin phosphotransferase gene from transposon Tn5," *Gene* 19:327-336 (1982).

Berry-Lowe, S. L., "The Nucleotide Sequence . . . Encoding the Small Subunit of Ribulose—1,5-Bisphosphate Carboxylase in Soybean" *J. Mol. Appl. Gen.* 1:483-498 (1982).

Bevan et al, "Expression of Bacterial Genes in Higher Plants," *J. of Cellular Biology*, Supp. 7B, Abstract 1212, p. 268 (1983).

Brinster et al, "Somatic Expression of Herpes Thymidine Kinase in Mice following Injection of a Fusion Gene into Eggs", *Cell* 27:223-231 (1981).

Condit et al, Abstract: Multiple Viral Specific Transcripts from the Genome of Cauliflower Mosaic Virus, Miami Winter Symposium, Jan. 17-21, 1983.

Goodman et al, "Gene Transfer in Crop Improvement", *Science* 236:48-54 (1987).

Gnonenborn et al, "Propagation of foreign DNA in plants using cauliflower mosaic virus as vector", *Nature* 294:773-776 (1981).

Guilley et al, "Transcription of Cauliflower Mosaic Virus DNA: Detection of Promoter Sequences, and Characterization of Transcripts," *Cell* 23:763-773 (1982).

Herrera-Estrella et al, "Expression of chimaeric genes transferred into plant cells using a Ti-plasmid-derived vector", *Chemical Abstracts*, vol. 99, 17349n (1983).

Howell, et al, "Rescue of in vitro generated mutants of cloned cauliflower mosaic virus genome in infected plants", *Nature* 293:483-486 (1981).

Koncz et al, "A simple method to transfer, integrate and study expression of foreign genes, such as chicken ovalbumin and α-actin in plant tumors", *The EMBO Journal*, vol. 3, No. 5:1029-1037 (1984).

Larkin et al, International Congress of Plant Tissue and Cell Cultivation Abstract, Tokyo Jul. 11-16, 1982.

Lorz et al, "Transformation Studies Using Synthetic DNA Vectors Coding for Antibiotic Resistance," abstract of talk presented at the International Congress of Plant Tissue and Cell Culture, Jul. 11-16, 1982 in Tokyo.

Seeburg, P.H. et al, "Efficient Bacterial Expression of Bovine and Porcine Growth Hormones," *DNA* 2(1): 37 (1983).

Shah et al, "Genes Encoding Actin in Higher Plants: Intron Positions Are Highly Conversed But the Coding Sequences Are Not", *J. Mol. Appl. Genet.* 2:111-126 (1983).

Shaw et al, "A general method for the transfer of cloned genes to plant cells", *Gene* 23:315-330 (1983).

Southern, P.J and P. Berg, "Transformation of Mammalian Cells in Antibiotic Resistance with Bacterial Gene Under Control of the SV40 Early Region Promoter," *J. Mol. Appl. Gen.* 1: 327-341 (1982).

Tuite et al, "Regulated high efficiency expression of human interferon-alpha in *Saccharomyces cerevisiae*," *The EMBO Journal*, 1:603-608 (1982).

Zambryski et al, "Ti plasmid vector for the introduction of DNA into plant cells without alteration of their normal regeneration capacity", *The EMBO Journal*, 2(12):2143-2150, (1980).

\* cited by examiner

FIG. II.

Sau3a FRAGMENT CONTAINING
NOS PROMOTER REGION
(ANTI-SENSE STRAND, 344 bp)

```
 Sau3a
   V        10           20           30           40           50
5'-TGATCATGAG  CGGAGAATTA  AGGGAGTCAC  GTTATGACCC  CCGCCGATGA 60           70           80           90          100
   CGCGGGACAA  GCCGTTTTAC  GTTTGGAACT  GACAGAACCG  CAACGTTGAA
                            SalI
                            V 120          130          140          150
   GGAGCCACTC  AGCCGCGGGT  TTCTGGAGTT  TAATGAGCTA  AGCACATACG
      110

160          170          180          190          200
   TCAGAAACCA  TTATTGCGCG  TTCAAAAGTC  GCCTAAGGTC  ACTATCAGCT 210          220          230          240          250
   AGCAAATATT  TCTTGTCAAA  AATGCTCCAC  TGACGTTCCA  TAAATTCCCC 260          270          280          290          300
   TCGGTATCCA  ATTAGAGTCT  CATATTCACT  CTCAATCCAA  ATAATCTGCA
              mRNA 5' END                    3'-GGTT  TATTAGACGT ──5'
                                             Synthetic
                                              Primer
      310          320          330          340
   ATGGCAATTA  CCTTATACCGC  AACTTCTTTA  CCTATTTCCG  CCGCAGATC
↑                                                         ^
START NOS STRUCTURAL                                     Sau3a
CODON SEQUENCE
```

FIG. 15

PLASMIDS FOR TRANSFORMING PLANT CELLS

This is a continuation of application Ser. No. 06/458,411, filed Jan. 17, 1983, now abandoned, and a continuation-in-part of application Ser. No. 06/458,414, filed Jan. 17, 1983, now abandoned.

TECHNICAL FIELD

This invention is in fields of genetic engineering, plant biology, and bacteriology.

BACKGROUND ART

In the past decade, the science of genetic engineering has developed rapidly. A variety of processes are known for inserting a heterologous gene into bacteria, whereby the bacteria become capable of efficient expression of the inserted genes. Such processes normally involve the use of plasmids which may be cleaved at one or more selected cleavage sites by restriction endonucleases. Typically, a gene of interest is obtained by cleaving one piece of DNA, and the resulting DNA fragment is mixed with a fragment obtained by cleaving a vector such as a plasmid. The different strands of DNA are then connected ("ligated") to each other to form a reconstituted plasmid. See, for example, U.S. Pat. Nos. 4,237,224 (Cohen and Boyer, 1980); 4,264,731 (Shine, 1981); 4,273,875 (Manis, 1981); 4,322,499 (Baxter et al, 1982), and 4,336,336 (Silhavy et al, 1982).

A variety of other reference works are available. Some of these works describe the natural process whereby DNA is transcribed into mRNA and mRNA is translated into protein, see, e.g., L. Stryer, *Biochemistry*, 2nd edition, p 559 et seq. (W. H. Freeman and Co., 1981); A. L. Lehninger, *Biochemistry*, 2nd edition, p. 853 et seq. (Worth Publ., 1975). Other works describe methods and products of genetic manipulation; see, e.g., T. Maniatis et al, *Molecular Cloning, A Laboratory Manual* (Cold Spring Harbor Labs, 1982); J. K. Setlow and A. Hollaender, *Genetic Engineering, Principles and Methods* (Plenum Press, 1979). Hereafter, all references will be cited in abbreviated form; a list of complete citations is included after the Examples.

Most of the genetic engineering work performed to date involves the insertion of genes into various types of cells, primarily bacteria such as *E. coli*, various other microorganisms such as yeast, and mammalian cells. However, many of the techniques and substances used for genetic engineering of animal cells and microorganisms are not directly applicable to genetic engineering involving plants.

As used herein, the term "plant" refers to a multicellular differentiated organism that is capable of photosynthesis, such as angiosperms and multicellular algae. This does not include microorganisms, such as bacteria, yeast, and fungi. The term "plant cell" includes any cell derived from a plant; this includes undifferentiated tissue such as callus or crown gall tumor, as well as plant seeds, propagules, pollen, or plant embryos.

Ti and Ri Plasmids

The tumor-inducing (Ti) plasmid of *Agrobacterium tumefaciens* has been proposed for use as a natural vector for introducing foreign genetic information into plant cells (Hernalsteen et al 1980; Rorsch and Schilperoort, 1978). Certain types of *A. tumefaciens* are capable of infecting a wide variety of plant cells, causing crown gall disease. The process of infection is not fully understood. At least part of the Ti plasmid enters the plant cell. Various metabolic alterations occur, and part of the Ti plasmid is inserted into the genome of the plant (presumably into the chromosomes). The part of the Ti plasmid that enters the plant genome is designated as "transferred DNA" (T-DNA). T-DNA is stably maintained in the plant DNA (Chilton et al, 1977; Yadev et al, 1980; Willmitzer et al, 1980; Otten et al, 1981).

Research by several laboratories has led to the characterization of several structural (i.e., protein coding) genes located in T-DNA (Garfinkel et al 1981; Leemans et al 1982), as well as other DNA sequences which appear to serve various other functions. For example, two sequences referred to as the "left border" and the "right border" appear to delineate T-DNA and may be involved in the process whereby T-DNA is transferred into plant chromosomes (Zambryski et al 1982).

A different species of *Agrobacterium, A. rhizogenes*, carries a "root-inducing" (Ri) plasmid which is similar to the Ti plasmid. Infection of a plant cell by *A. rhizogenes* causes hairy root disease. Like the Ti plasmid, a segment of DNA called "T-DNA" (also referred to by some researchers as "R-DNA") is transferred into the plant genome of an infected cell.

Various other bacteria are also reported to be capable of causing genetic transformation of plant cells, including *A. rubi* and certain bacteria of the genus *Rhizobia* which have been treated with a mutagenic agent. Hooykaas et al, at page 156 of Setlow and Holaender, 1979.

As used herein, the term plant tumor inducing plasmid includes any plasmid (1) which is contained in a microorganism, other than a virus, which is capable of causing genetic transformation of one or more types of plants or plant cells, and (2) which contains a segment of DNA which is inserted into a plant genome. This includes Ri plasmids.

As used herein, the ter "T-DNA" refers to a segment of DNA in or from Plant tumor inducing plasmid (1) which has been inserted into the genome of one or more types of plant cells, or (2) which is contained in a segment of DNA that is located between two sequences of bases which are capable of serving as T-DNA borders. As used herein, the terms "T-DNA border" and "border" are determined and applied empirically; these terms shall refer to a sequence of bases which appears at or near the end of a segment of DNA which is transferred from a plant tumor inducing plasmid into a plant genome.

Despite the existing knowledge of T-DNA and plant tumor inducing plasmids, no one prior to this invention has been able to utilize these vectors for the introduction of foreign genes which are expressed in genetically modified plants. A variety of obstacles to such use have been encountered in genetic engineering efforts. Such obstacles include:

1) the large size (approximately 200,000 base pairs) and resulting complexity of plant tumor inducing plasmids preclude the use of standard recombinant DNA techniques to genetically modify and/or insert foreign genes into specific sites in the T-DNA. For example, there are no known unique restriction endonuclease cleavage sites in a Ti plasmid (Leemans et al, 1982).

2) the T-DNA, which is inserted into and expressed in plant cells, contains genes which are involved in the production of high levels of phytohormones in the transformed plant cells (Leemans et al 1982). The high levels of phytohormones interfere with the normal metabolic and regenerative process of the cells, and prevent the formation of phenotypically normal plants from the cells (Braun and Wood, 1976; Yang et al, 1980). Exceptions to this are rare cases where the T-DNA has undergone extensive spontaneous deletions in planta to eliminate those genes involved in phytohormone production. Under these conditions, normal plants are reported to be obtainable at low frequency (Otten et al, 1981). However, the T-DNA genes involved in phytohormone production could not be deleted prior to this invention, since they were very important in the identification and/or selection of transformed plant cells (Marton et al, 1979):

As described above, simple recombinant DNA techniques for introducing foreign genes into plasmids are not applicable to the large Ti plasmid. As a result, several indirect methods have been developed and are discussed below. The first reported use of the Ti plasmid as a vector was in model experiments in which bacterial transposons were inserted into T-DNA and subsequently introduced into plant cells. The bacterial transposons were reported to be stably maintained in the plant genome (Hernalsteens et al, 1980; Garfinkel et al 1981). However, in these cases the transformed tumor tissues were found to be incapable of regeneration into normal plants, and there was no reported evidence for the expression of bacterial genes in the plant cells. In addition, because the insertion of bacterial transposons is believed to be essentially random, a great deal, of effort was required to identify and localize the position of the inserted DNA in these examples. Therefore, this approach is not likely to be useful to introduce desired genes in a predictable manner into plants.

Other researchers have reported the use of intermediate vectors which replicate in both *E. coli* and *A. tumefaciens* (Matzke and Chilton, 1981; Leemans et al 1981; Garfinkel et al, 1981). The intermediate vectors contain relatively small subfragments of the Ti plasmid which can be manipulated using standard recombinant DNA techniques. The subfragments can be modified by the deletion of specific sequences or by the insertion of foreign genes at specific sites. The intermediate vectors containing the modified T DNA subfragment are then introduced into *A. tumefaciens* by transformation or conjugation. Double recombination between the modified T-DNA fragment on the intermediate vector and its wild-type counterpart on the Ti plasmid results in the replacement of the wild-type copy with the modified fragment. Cells which contain the recombined Ti plasmids can be selected using appropriate antibiotics.

Various foreign DNA's have been inserted at specific sites in the T-DNA by this method and they have been reported to be stably transferred into plant cells (Matzke and Chilton, 1981, Leemans et al 1981, 1982). However, such foreign genes have not been reported to be capable o' f expression in plant cells, and the transformed plant cells remain incapable of regeneration into normal plants. Furthermore, in the procedure described above, it is preferred for a double crossover event to occur, in order to substitute the modified DNA fragment for the wild-type copy. A single crossover results in the formation of a co-integrate plasmid which contains two copies of the T-DNA subfragments. This duplication is undesirable in these methods since homologous recombination, which can occur in *A. tumefaciens* cells or in plant cells, can result in the loss of the inserted foreign gene(s).

A major disadvantage of the above methods is that the frequency of double recombination is quite low, about $10^{-4}$ to $10^{-9}$ (Leemans et al, 1981) and it requires extensive effort to identify and isolate the rare double-crossover recombinants. As a result, the number and types of experiments which can be performed using existing methods for genetically engineering the Ti plasmid is severely limited.

Other Means for Inserting DNA into Plant Cells

A variety of other methods have been reported for inserting DNA into plant cells. One such method involves the use of lipid vesicles, also called liposomes, to encapsulate one or more DNA molecules. The liposomes and their DNA contents may be taken up by plant cells; see, e.g., Lurquin, 1981.

If the inserted DNA can be incorporated into the plant genome, replicated, and inherited, the plant cells will be transformed.

Other alternate techniques involve contacting plant cells with DNA which is complexed with either (a) polycationic substances, such as poly-L-ornithine (Davey et al, 1980), or (b) calcium phosphate (Krens et al, 1982). Using these techniques, all or part of a Ti plasmid has been reportedly inserted into plant cells, causing tumorigenic alteration of the plant cells.

Another method has been developed involving the fusion of bacteria, which contain desired plasmids, with plant cells. Such methods involve converting the bacteria into spheroplasts and converting the plant cells into protoplasts. Both of these methods remove the cell wall barrier from the bacterial and plant cells, using enzymic digestion. The two cell types can then be used together by exposure to chemical agents, such as polyethylene glycol. See Hasezawa et al, 1981.

However, all of the foregoing techniques suffer from one or more of the following problems:

1. transformation efficiencies reported to date have been very low;
2. only small DNA molecules can be inserted into plant cells;
3. only small numbers of DNA molecules can be inserted into plant cells; and/or,
4. a gene which is inserted into a plant cell will not be stably maintained by the plant cell unless it is incorporated into the genome of the plant cell, i.e., unless the gene is inserted into a chromosome or plasmid that replicates in the plant cell.

For these and possibly other reasons, no one has yet reported expression of a gene inserted into a plant cell by any of the foregoing techniques, except for the tumorigenic transformations noted above.

Prior to this invention, no satisfactory method existed for the creation and identification of genetically transformed plant cells which could be routinely regenerated into morphologically normal plants.

SUMMARY OF THE INVENTION

This invention relates to several plasmids which are useful for creating transformed plant cells which are capable of subsequent regeneration into differentiated, morphologically-normal plants. This invention also relates to microorganisms containing such plasmids, and to methods for creating such plasmids and microorganisms.

This invention involves a first plasmid, such as pMON120, which has certain desired characteristics described below. A gene which is capable of being expressed in plant cells may be inserted into this plasmid to obtain a derivative plasmid, such as pMON128. For example, plasmid pMON128 contains a chimeric gene which expresses neomycin phosphotransferase II (NPT II), an enzyme which inactivates certain antibiotics. The chimeric gene is capable of expression in plant cells.

The derivative plasmid is inserted into a suitable microorganism, such as *Agrobacterium tumefaciens* cells which contain plant tumor inducing plasmids. In the *A. tumefaciens* cells, some of the inserted plasmids recombine with, plant tumor inducing plasmids to form a co-integrate plasmid; this is due to a region of homology between the two plasmids. Only a single crossover event is required to create the desired co-integrate plasmid.

Because of the characteristics of the inserted plasmid this invention, the resulting co-integrate plant tumor inducing contain the chimeric gene and/or any other inserted gene within the T-DNA region of the co-integrate plasmid. The inserted gene(s) are surrounded by at least two T-DNA borders, at least one of which was inserted into the plant tumor inducing plasmid by the crossover event. By means of appropriate antibiotics, A. tumefaciens cells which do not have co-integrate plant tumor inducing plasmids with inserted genes are killed.

A. tumefaciens cells with co-integrate plasmids are co-cultured with plant cells, such as protoplasts, protoplast-derived cells, plant cuttings, or intact plants, under conditions which allow the co-integrate plant tumor inducing plasmids, or portions thereof, to enter the plant cells. Once inside the plant cells, a portion of the plant tumor inducing plasmid which is surrounded by the two T-DNA borders is inserted by natural processes into the plant genome. This segment of DNA contains the chimeric gene and/or any other desired gene(s). Preferably, the segment of vector DNA which is inserted into the plant genome does not contain any genes which would render the plant cell incapable of being regenerated into a differentiated, morphologically-normal plant. The transformed plant cell(s) may be regenerated into a morphologically-normal plant which will pass the inserted gene to its descendants.

A variety of uses exist for plants transformed by the method of this invention. For example, a gene which codes for an enzyme, which inactivates a herbicide may be inserted into a plant. Alternately, a gene which codes for a desired mammalian polypeptide such as growth hormone, insulin, interferon, or somatostatin may be inserted into plants. The plants may be grown and harvested, and the polypeptide could be extracted from the plant tissue.

BRIEF DESCRIPTION OF THE DRAWINGS

FIG. 15 represents a DNA fragment which contains a NOS promoter region, a NOS 5' non-translated region, and the first few codons of the NOS structural sequence.

DETAILED DESCRIPTION OF THE INVENTION

Figure 1:
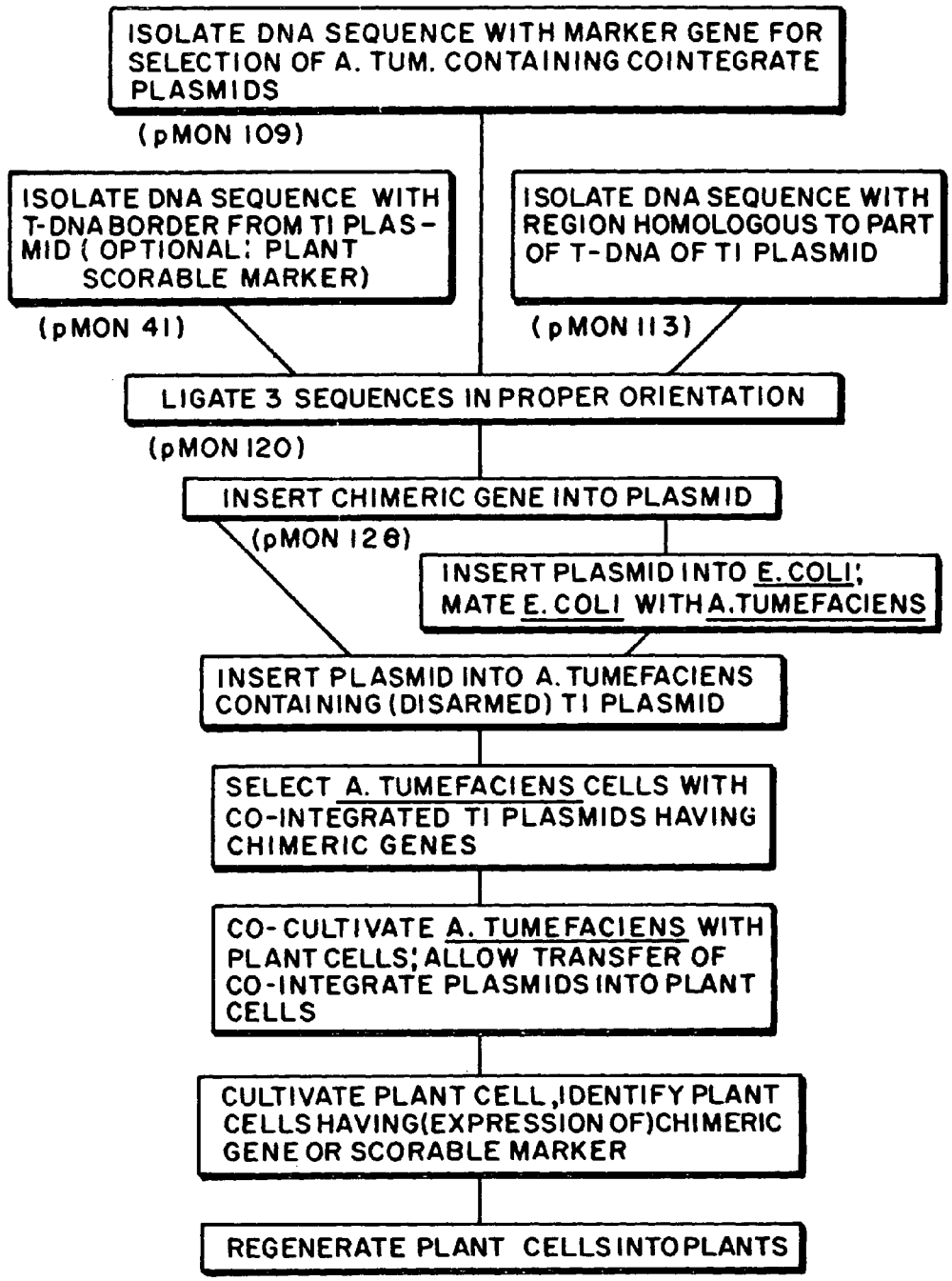
FIG. 1 is a flow chart indicating the steps of this invention, using pMON128 and the NOS-NPT II gene as an example.

In one preferred embodiment of this invention, a variety of chimeric genes were inserted into plant cells using the steps that are summarized on the flow chart of FIG. 1. As shown on FIG. 1, three preliminary plasmids were prepared. Those plasmids were designated as:

1. pMON41, which contained a right border from a nopaline-type Ti plasmid, and the 5' portion of a nopaline synthase (NOS) gene. The construction of plasmid pMON41 is described below and shown in FIG. 2.

2. pMON109, which contained the 3' portion of a NOS gene, and a selectable marker gene (spc/str) which allowed for the selection of *A. tumefaciens* cells having co-integrate Ti plasmids with chimeric genes. The construction of plasmid pMON109 is described below and shown in FIGS. 3, 4, and 5.

3. pMON113, which contained a region of DNA with a sequence that is identical to the sequence within the T-DNA portion of an octopine-type Ti plasmid. This region was designated as the "left inside homology" (LIR) region. The construction of pMON113 is described below and shown in FIG. 6.

Figure 7:
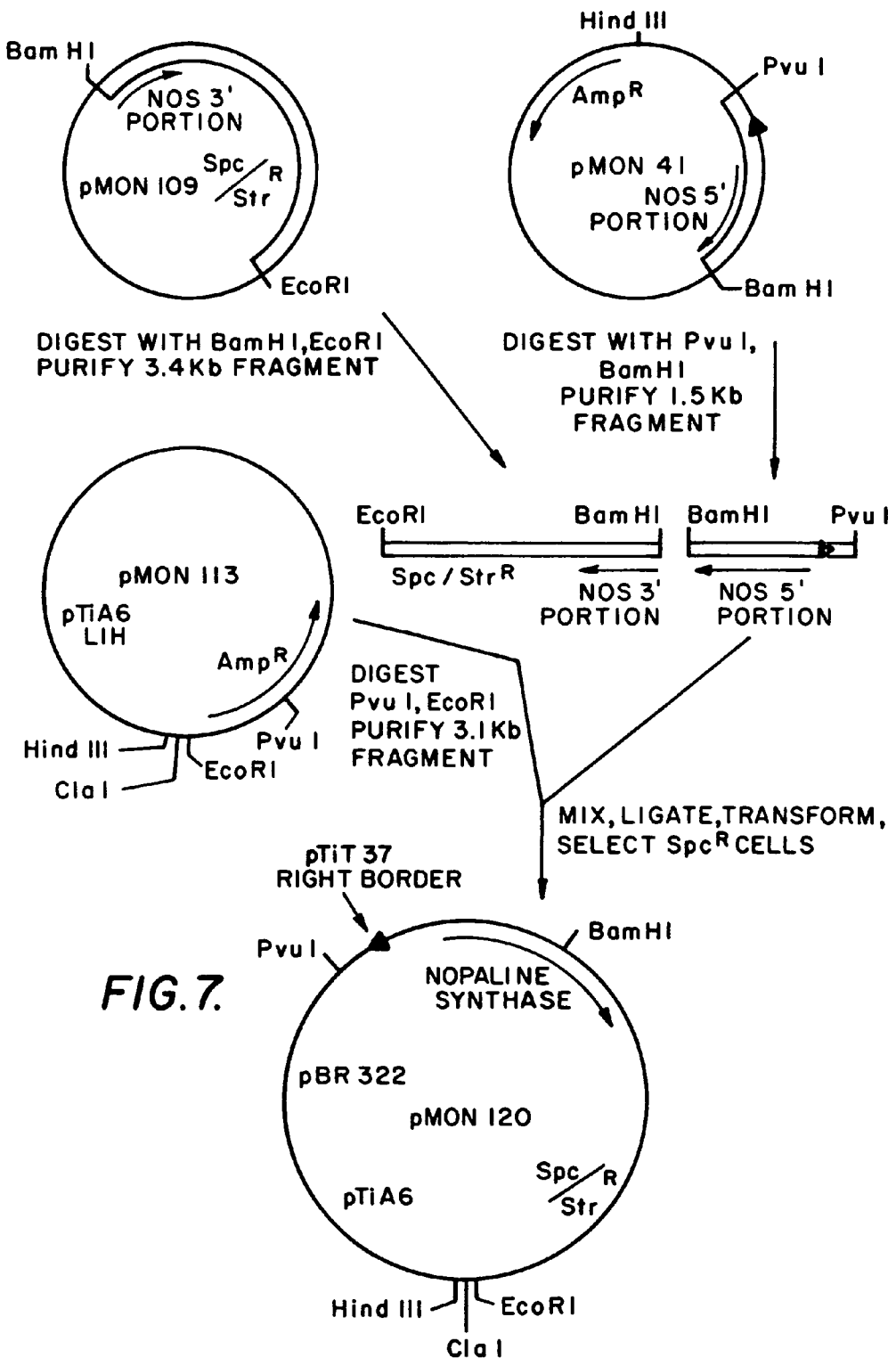
FIG. 7 represents the creation of plasmid pMON120, an intermediate vector with three restriction endonuclease cleavage sites which are suitable for the insertion of a desired gene.

After these plasmids were assembled, each plasmid was digested by appropriate endonucleases to obtain a desired fragment. Three fragments (one from each of the three plasmids) were assembled in a triple ligation to obtain the intermediate vector, plasmid pMON120, as shown in FIG. 7.

Plasmid pMON120 plays a key role in the embodiment of this invention that is described in detail below. This plasmid has the following characteristics:

1. pMON120 has at least three unique restriction endonuclease cleavage sites (EcoRI, ClaI, and HindIII) which allow for the convenient insertion of any desired gene.

2. pMON120 will replicate within normal *E. coli* cells. However, it will not replicate within normal *Agrobacterium* cells unless it co-integrates with another plasmid, such as a Ti plasmid, which will replicate in *Agrobacterium* cells.

3. pMON120 carries a marker gene which codes for an enzyme which confers resistance to two antibiotics, spectinomycin (spc) and streptomycin (str). This gene, referred to as the spc/str gene, is expressed in *E. coli* and in *A. tumefaciens*, but not in plant cells. pMON120 does not carry genes which code for resistance to ampicillin or tetracycline.

4. pMON120 carries a sequence which is homologous to a sequence within the T-DNA portion of an octopine-type Ti plasmid of *A. tumefaciens*. This sequence is referred to as the "left inside homology" (LIH) region. This region of homology promotes a crossover event whereby pMON120, or a derivative of pMON120 such as pMON128, forms a co-integrate with the Ti plasmid if the two plasmids exist inside the same *A. tumefaciens* cell. By definition, the "co-integrate" plasmid is formed by a single crossover event. It contains all DNA sequences that previously existed in either the Ti plasmid or the pMON120-derived plasmid.

5. pMON120 carries a nopaline-type T-DNA "right border," i.e., a sequence which is capable of acting as one end (designated by convention as the right border) of a T-DNA sequence which is transferred from a Ti plasmid and inserted into the chromosome of a plant cell during transformation of the cell by *A. tumefaciens*.

6. pMON120 carries a gene (including a promoter) which codes for the expression of an enzyme, nopaline synthase (NOS). Once introduced into a plant cell, the NOS enzyme catalyzes the production of nopaline, a type of opine. In most types of plants, opines are non-detrimental compounds which accumulate at low levels; the presence of nopaline can be readily detected in plant tissue (Otten and Schilperoort, 1978). Opine genes may serve as useful marker genes to confirm transformation, since opines do not normally exist in untransformed plant cells. If desired, the NOS gene in pMON120 may be rendered non-functional by a variety of techniques known to those skilled in the art. For example, a BamHI cleavage site exists within the coding portion of the NOS gene; a stop codon or other appropriate oligonucleotide sequence could be inserted into this site to prevent the translation of NOS.

7. The relative location of the various genes, cleavage sites, and other sequences in pMON120 is very important to the performance of this invention. The entire pMON120 plasmid, or its derivative plasmid such as pMON128, will be contained in the co-integrate Ti plasmid.

However, only part of the co-integrate Ti plasmid (the modified T-DNA region) will be inserted into the plant genome. Therefore, only a part of the pMON120-derived plasmid will be inserted into the plant genome. This portion begins at the T-DNA border, and stretches in one direction only to the region of homology. In pMON120, the NOS scorable marker, the spc/str selectable marker, and the three insertion sites are within the portion of pMON120 that would be transferred into the plant genome. However, the pBR322-derived region next to the LIH, and the PvuI cleavage site, probably would not be transferred into the plant genome. Importantly, this arrangement of pMON120 and its derivatives prevents the transfer of more than one region of homology into the plant genome, as discussed below.

8. pMON120 is about 8 kilobases long. This is sufficiently small to allow it to accomplish all of the objectives of this invention. However, if desired, it may be made somewhat smaller by the deletion of one or more nucleotide sequences which are not essential, using methods which are known to those skilled in the art. Such a reduction in size might improve the efficiency or other characteristics of the plasmid when used for this invention or for other purposes, as may be determined by those skilled in the art.

It is recognized that a wide variety of intermediate vectors which differ from pMON120 in one or more respects may be prepared and utilized by those skilled in the art. For example, the NOS marker used for scoring transformed plant cells might be deleted, or replaced or supplemented by a different scorable or selectable marker. One such marker gene might comprise an antibiotic-resistance gene such as the NOS-NPT II-NOS chimeric gene described below. As another example, the spc/str marker gene used for selecting *A. tumefaciens* cells with co-integrate plasmids might be deleted, or replaced or supplemented by a different scorable or selectable marker that is expressed in *Agrobacteria*. As another example, a variety of T-DNA borders (such as a nopaline-type "left" border, or an octopine-type left or right border) might be utilized. Similarly, more than one border (such as two or more nopaline right borders, or one nopaline right border and one octopine right border) might be inserted into the intermediate vector, in the desired orientation; this may increase the frequency of insertion of the T-DNA into the plant genome, as may be determined by those skilled in the art. It is also possible to insert both left and right borders (of any type) into an intermediate vector. It is also possible to increase the length of the region of homology; this is likely to increase the frequency of the desired single crossover event (Leemans et al, 1981). It is also possible to select an appropriate region of homology from any type of desired plasmid, such as a nopaline or agropine Ti plasmid or an Ri plasmid; such regions will allow the intermediate vector to form a co-integrate with any desired plasmid.

Method of Creating pMON120

Plasmid pMON120 was constructed from fragments derived from 3 other plasmids. These three plasmids were designated as pMON41, pMON109, and pMON113. The construction of each of these three plasmids is summarized below; additional information is provided in the examples.

Plasmid pMON41 contributed a nopaline-type T-DNA right border and the 5' portion of a nopaline synthase (NOS) gene to pMON120. It was created by the following method.

Figure 2:
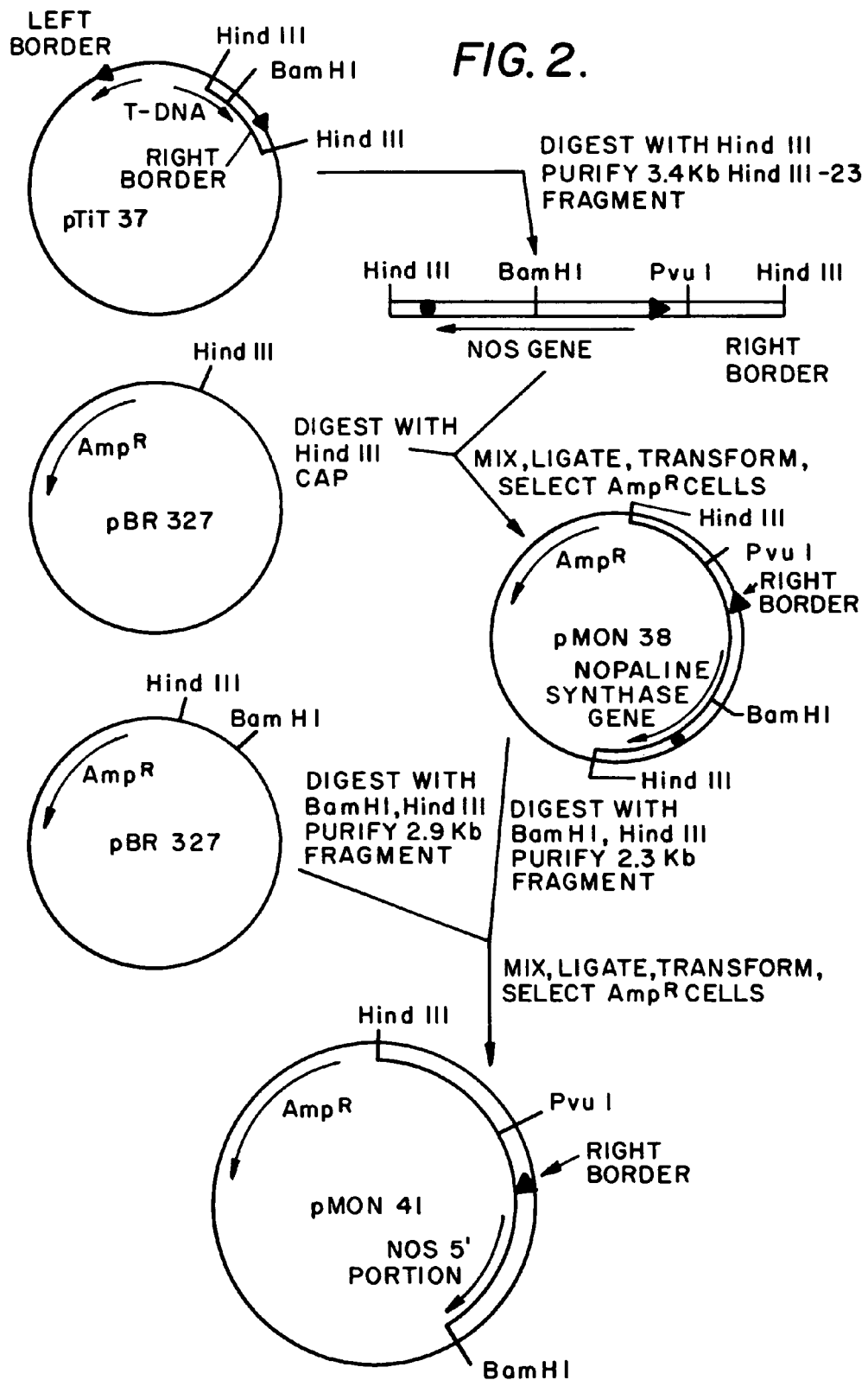
FIG. 2 represents the creation of pMON41, a plasmid used to construct pMON120.

A nopaline-type Ti plasmid, designated as the pTiT37 plasmid, may be digested with the HindIII endonuclease to produce a variety of fragments, including a 3.4 kb fragment which is designated as the HindIII-23 fragment. This fragment contains the entire NOS gene and the T-DNA right border. The Applicants inserted a HindIII-23 fragment into a plasmid, pBR327 (Soberon et al, 1980), which had been digested with HindIII. The resulting plasmid, designated as pMON38, was digested with both HindIII and BamHI. This produced a 2.3 kb fragment which contains the nopaline-type right border and the portion of a NOS gene (including the promoter region, the 5' non-translated region, and part of the structural sequence). This 2.3 kb fragment was inserted into a pBR327 plasmid which had been digested with HindIII and BamHI. The resulting plasmid was designated as pMON41, as shown in FIG. 2.

A variety of strains of *A. tumefaciens* are publicly available from the American Type Culture Collection (Rockville, Mb): accession numbers are listed in any ATCC catalog. Each strain contains a Ti plasmid which is likely to be suitable for use in this invention, as may be determined through routine experimentation by those skilled in the art.

Plasmid pMON109 contributed a spc/str selectable marker gene and the 3' portion of a NOS gene to pMON120. It was created by the following method.

Plasmid pMON38 (described above and shown on FIG. 2) was digested with RsaI, which creates blunt ends as shown:

5'-GTAC

CATG

Figure 3:
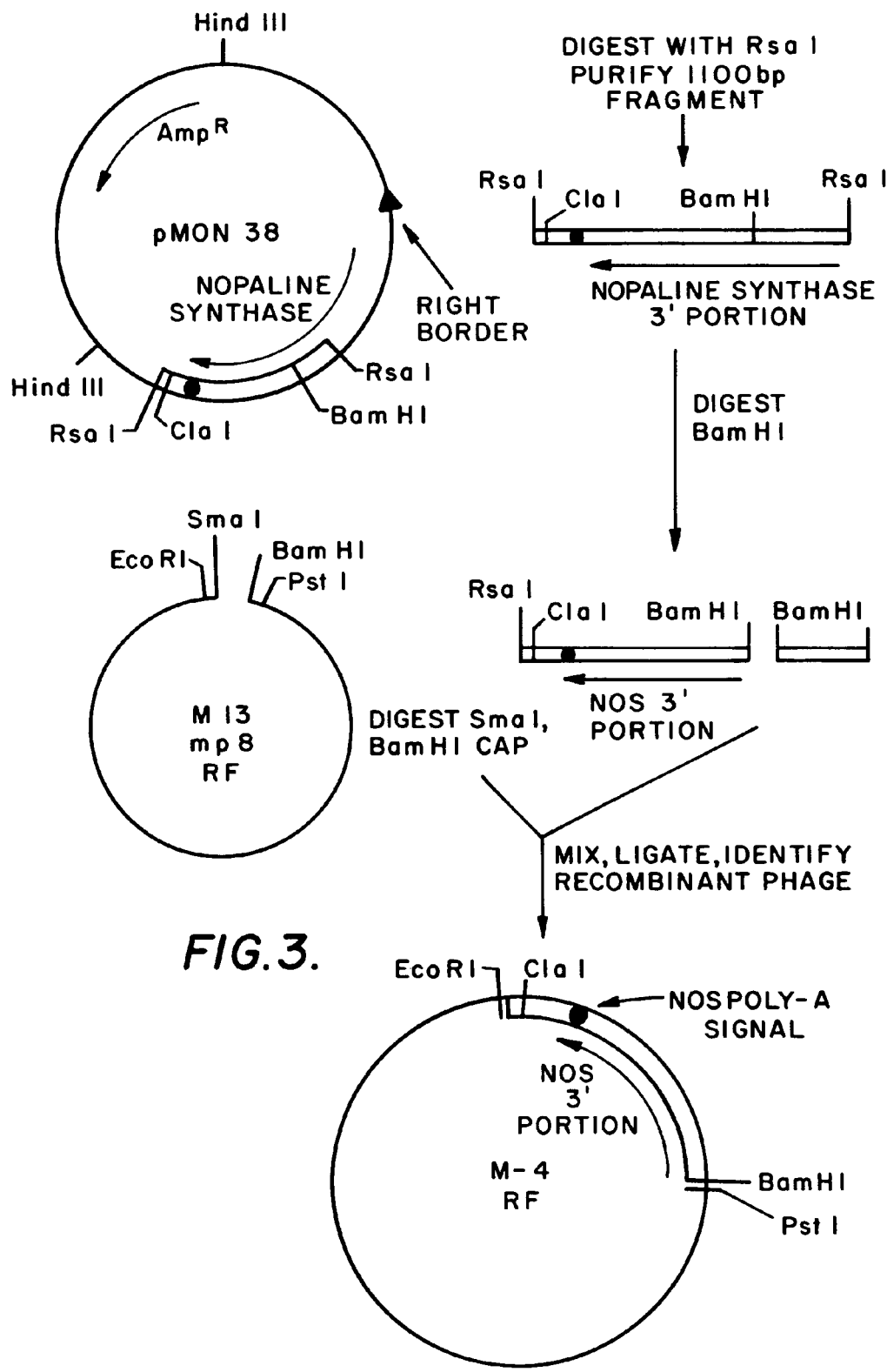
FIG. 3 represents the creation of M-4, an M13-derived DNA used to construct pMON109.

A 1.1 kb fragment was isolated, and digested with BamHI to obtain fragments of 720 bp and 400 bp, each of which had one blunt Rsa end and a cohesive BamHI end. These fragments were added to double stranded DNA from a phage M13 mp 8 (Messing and Vieira, 1982) which had been digested with SmaI (which creates blunt ends) and BamHI. The mixture was ligated, transformed into cells and plated for recombinant phage. Recombinant phage DNA's which contained the inserted 720 bp fragment were identified by the size of the BamHI-SmaI insert. One of those phage DNA's was designated as M-4, as shown in FIG. 3. The 720 bp insert contained the 3' non-translated region (including the poly-adenylation signal indicated in the figures by a heavy dot) of the NOS gene, as well as the 3' portion of the structural sequence of the NOS gene. The 720 bp insert is surrounded in M-4 by EcoRI and PstI cleavage sites, which were present in the M13 mp 8 DNA.

A bacterial transposon, designated as Tn7, is known to contain the spc/str gene, mentioned previously. The Tn7 transposon also contains a gene which causes the host cell to be resistant to the antibiotic trimethoprim. The exact location and orientation of the spc/str gene and the trimethoprim-resistance gene in Tn7, are not known. The Tn7 transposon may be obtained from a variety of cell strains which are publicly available. A strain of *A. tumefaciens* was isolated in which the Tn7 transposon had been inserted into the Hind 111-23 region of a pTiT37 plasmid. The modified pTiT37 plasmid was designated as pGV3106 (Hernalsteens et al, 1980).

Plasmid pGV3106 was digested with HindIII, and the fragments were shotgun-cloned into pBR327 plasmids which had been digested with HindIII. These plasmids were inserted into *E. coli* cells, and cells which were ampicillin-resistant (due to a pBR327 gene) and trimethoprim-resistant (due to a Tn7 gene) were selected. The plasmid obtained from one colony was designated as pMON31. This plasmid contained a 6 kb HindIII insert. The insert contained the spc/str-resistance gene and trimethoprim-resistance gene from Tn7, and the 3' portion of a NOS gene (which came from the pTiT37 plasmid).

Plasmid pMON31 was reduced in size twice. The first reduction was performed by digesting the plasmid with EcoRI, diluting the mixture to remove an 850 bp fragment, and religating the large fragment. The resulting plasmid, designated as pMON53, was obtained from transformed cells selected by their resistance to ampicillin and streptomycin. Resistance to trimethoprim was not determined.

Figure 4:
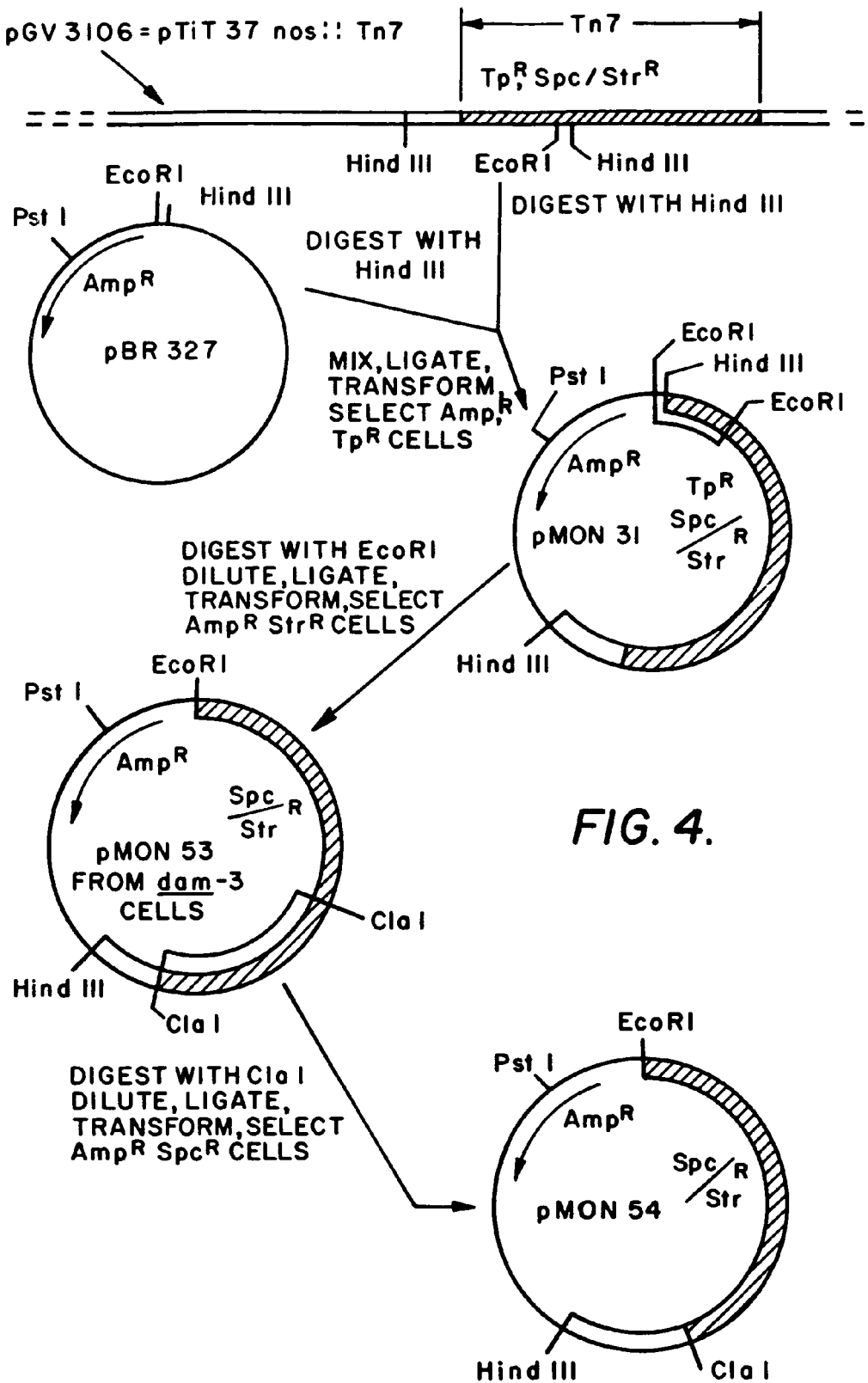
FIG. 4 represents the creation of pMON54, a plasmid used to construct pMON109.

Plasmid pMON53 was further reduced in size by digesting the plasmid with ClaI, diluting the mixture to remove a 2 kb fragment, and religating the large fragment. The resulting 5.2 kb plasmid was designated as pMON54, as shown in FIG. 4. This plasmid contains the spc/str gene.

Figure 5:
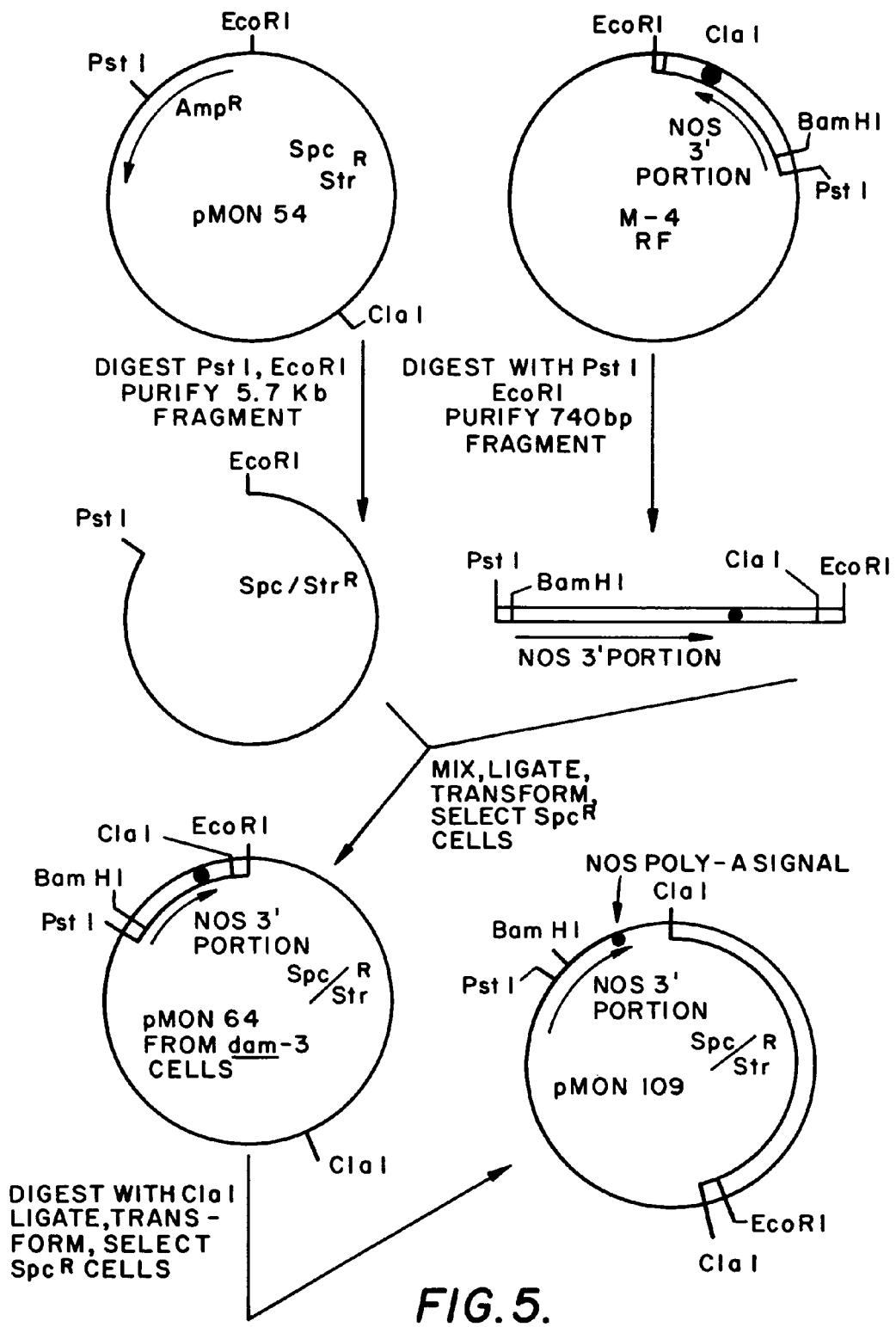
FIG. 5 represents the creation of pMON109, a plasmid, used to construct pMON120.

Plasmid pMON54 was digested with EcoRI and PstI, and a 4.8 kb fragment containing the spc/str gene was isolated. M-4 DNA was digested with EcoRI and PstI, and a 740 bp fragment containing the NOS 3' non-translated region was isolated. These fragments were ligated together to form pMON64. In order to be able to obtain the NOS 3' portion and the spc/str gene on a single EcoRI-BamHI fragment, the orientation of the spc/str gene was reversed by digesting pMON64 with ClaI and religating the mixture. Plasmids having the desired orientation were identified by cleavage using EcoRI and BamHI. These plasmids were designated as pMON109, as shown in FIG. 5.

Plasmid pMON113 contributed a region of homology to pMON120 which allows pMON120 to form a co-integrate plasmid when present in *A. tumefaciens* along with a Ti plasmid. The region of homology was taken from an octopine-type Ti plasmid. In the Ti plasmid, it is located near the left T-DNA border, within the T-DNA portion of the Ti plasmid. This region of homology is designated as the "left inside homology" (L1H) region.

A region of homology may be derived from any type of plasmid capable of transforming plant cells, such as any Ti plasmid or any Ri plasmid. An intermediate vector can be designed which can form a co-integrate plasmid with whatever type of plasmid the region of homology was derived from.

In addition, it might not be necessary for the region of homology to be located within the T-DNA. For example, it may be possible for a region of homology to be derived from a segment of a Ti plasmid which contains a T-DNA border and a sequences of bases outside of the T-DNA region. Indeed, if the intermediate vector contains two appropriate T-DNA borders, it might be possible for the region of homology to be located entirely outside of the T-DNA region.

Figure 6:
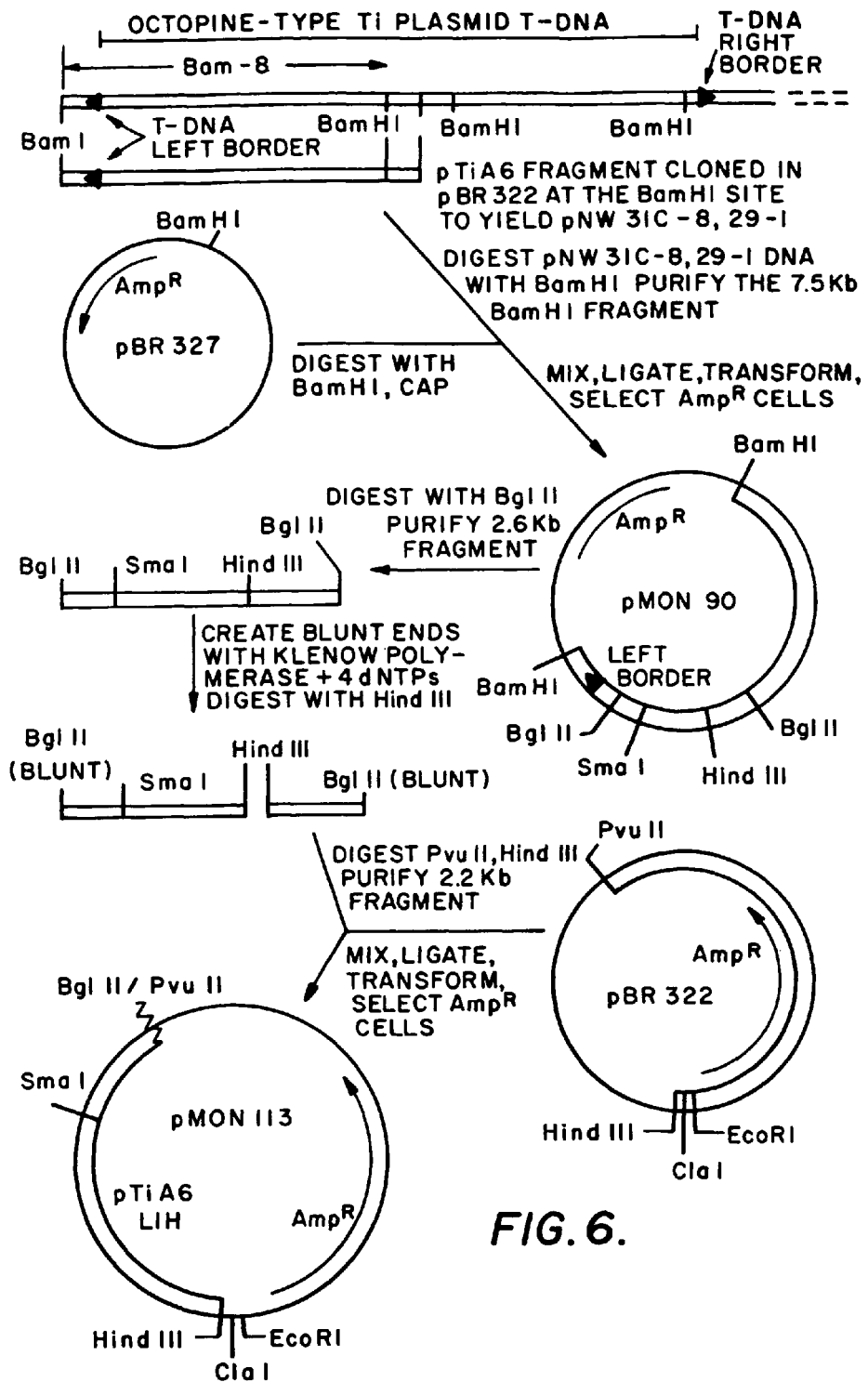
FIG. 6 represents the creation of pMON113, a plasmid used to construct pMON120.

The Applicants obtained an *E. coli* culture with a pBR-derived plasmid containing the Bam-8 fragment of an octopine-type Ti plasmid. The Bam-8 fragment, which is about 7.5 kb, contains the left border and the L1H region of the Ti plasmid (Willmitzer et al, 1982; DeGreve et al, 1981). The Bam-8 fragment was inserted into the plasmid pBR327, which had been digested with BamHI. The resulting plasmid was designated as pMON90, as shown in FIG. 6.

Plasmid pMON90 was digested with BglII, and a 2.6 kb fragment which contains the L1H region but not the left border was purified. The 2.6 kb fragment was treated with Klenow polymerase to convert the cohesive ends into blunt ends, and the fragment was digested with HindIII to obtain a 1.6 kb fragment (the desired fragment) and a 1 kb fragment. Both fragments were mixed with a pBR322 plasmid which had been digested with PvuII and HindIII. The mixture was ligated, and inserted into E. coli cells. The cells were selected for ampicillin resistance, and scored for the presence of a SmaI site which exists on the 1.6 kb fragment but not the 1 kb fragment. A colony having the desired plasmid was identified, and the plasmid froth this colony was designated as pMON113, as indicated by FIG. 6.

To assemble pMON120, three fragments had to be isolated. Plasmid pMON41 was digested with PvuI and BamI, and a 1.5 kb fragment containing a nopaline-type right border and the 5' portion of a NOS gene was isolated. Plasmid pMON109 was digested with BamHI and EcoRI, and a 3.4 kb fragment containing a spc/str gene and the 3' part of a NOS gene was isolated. Plasmid pMON113 was digested with PvuI and EcoRI, and a 3.1 kb fragment containing the LIH region was isolated.

The three fragments were mixed together and ligated to form pMON120, as shown on FIG. 7. A culture of E. coli containing pMON120 has been deposited with the American Type Culture Center. This culture has been assigned accession number 39263.

It is recognized that a variety of different methods could be used to create pMON120, or any similar intermediate vector. For example, instead of the triple ligation, it would have been possible to assemble two of the desired fragments in a plasmid, and insert the third fragment into the plasmid.

Method of Using pMON120

As mentioned previously, pMON120 has three unique cleavage sites (EcoRI, ClaI, and HindIII) which are suitable for the insertion of any desired gene. These cleavage sites are located in the portion of pMON120 that will be inserted into a plant genome, so the inserted gene also will be inserted into the plant genome.

A variety of chimeric genes which are capable of expressing bacterial and mammalian polypeptides in plant cells have been created by the Applicants. These chimeric genes are described in detail in a separate, simultaneously-filed application entitled "Chimeric Genes Suitable for Expression in Plant Cells," Ser. No. 458,414. The contents of that application are hereby incorporated by reference. Those chimeric genes are suitable for use in this invention. They may be inserted into pMON120 to create a derivative plasmid, which may be utilized as described below.

The chimeric gene comprises a promoter region which is capable of causing RNA polymerase in a plant cell to create messenger RNA corresponding to the DNA. One such promoter region comprises a nopaline synthase (NOS) promoter region, which normally exists in certain types of Ti plasmids in bacteria, A. tumefaciens. The NOS gene normally is inactive while contained in A. tumefaciens cells, and it becomes active after the Ti plasmid enters a plant cell. Other suitable promoter regions may be derived from genes which exist naturally in plant cells.

The chimeric gene also contains a sequence of bases which codes for a 5' non-translated region of mRNA which is capable of enabling or increasing the expression in a plant cell of a structural sequence of the mRNA. For example, a suitable 5' non-translated region may be taken from the NOS gene mentioned above, or from a gene which exists naturally in plant cells.

The chimeric gene also contains a desired structural sequence, i.e., a sequence which is transcribed into mRNA which is capable of being translated into a desired polypeptide. The structural sequence is heterologous with respect to the promoter region, and it may code for any desired polypeptide, such as a bacterial or mammalian protein. The structural sequence includes a start codon and a stop codon. The structural sequence may contain introns which are removed from the mRNA prior to translation.

If desired, the chimeric gene may also contain a DNA sequence which codes for a 3' non-translated region (including a poly-adenylation signal) of mRNA. This region may be derived from a gene which is naturally expressed in plant cells, to help ensure proper expression of the structural sequence. Such genes include the NOS gene mentioned above, as well as genes which exist naturally in plant cells.

If properly assembled and inserted into a plant genome, a chimeric gene of this invention will be expressed in the plant cell to create a desired polypeptide, such as a mammalian hormone, or a bacterial enzyme which confers antibiotic or herbicide resistance upon the plant.

In one preferred embodiment of this invention, a chimeric gene was created which comprises the following DNA sequences:

1. a promoter region and a 5' non-translated region derived from a nopaline synthase (NOS) gene;
2. a structural sequence derived from a neomycin phosphotransferase II (NPT II) gene; and
3. a 3' non-translated region derived from a NOS gene.

Figure 8:
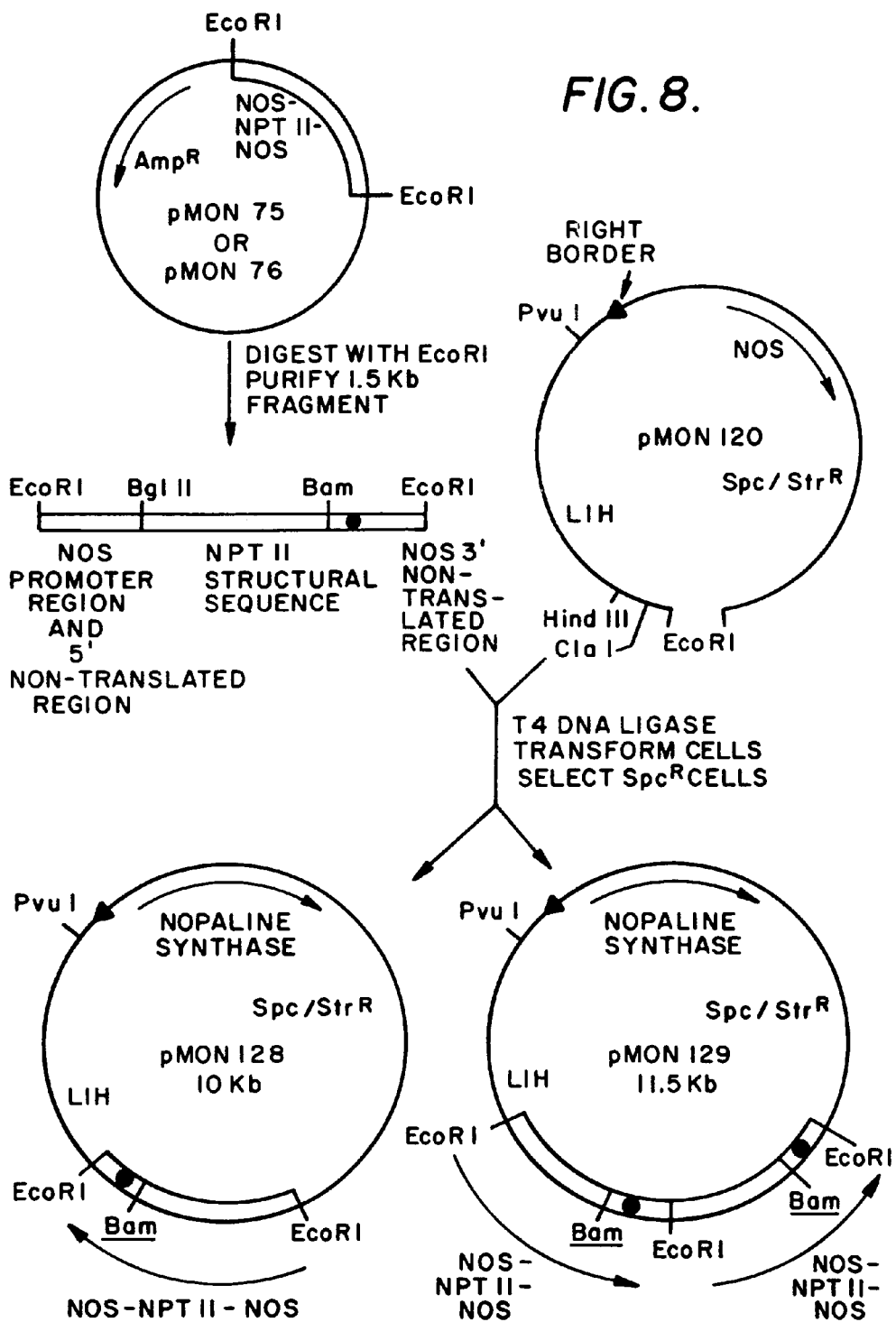
FIG. 8 represents the creation of pMON128, an intermediate vector which was obtained by inserting a chimeric NOS-NPT II kanamycin-resistance gene into pMON120.

This chimeric NOS-NPT II-NOS gene was isolated on a DNA fragment having EcoRI ends. This fragment was inserted into the EcoRI cleavage site of pMON120, and the resulting plasmids (having chimeric gene inserts with opposite orientations) were designated as pMON128 and pMON129, as shown in FIG. 8. Plasmid pMON129 has two copies of the chimeric gene; this may be a useful feature in certain types of work. Either plasmid may be utilized to transform plant cells, in the following manner. A culture of E. coli containing pMON128 has been deposited with the American Type Culture Collection. This culture has been assigned accession number 39264.

Figure 13:
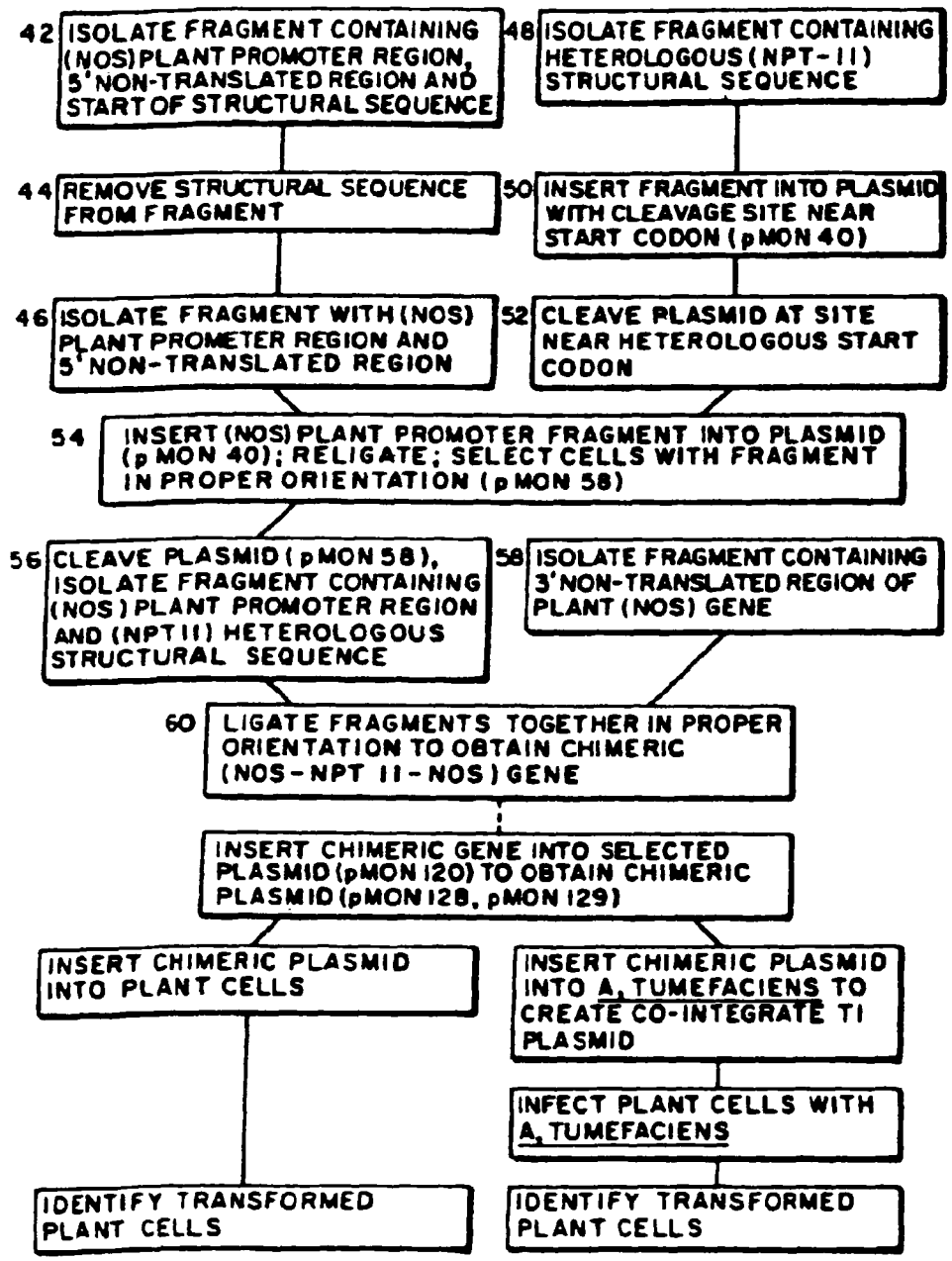
FIG. 13 is a flow chart representing steps of this invention, correlated with an example chimeric NOS-NPTII-NOS gene

The method used to assemble this chimeric gene is summarized in the flow chart of FIG. 13, and described in detail below and in the examples. To assist the reader in understanding the steps of this method, various plasmids and fragments involved in the NOS-NPTII-NOS chimeric gene are cited in parentheses in FIG. 13. However, the method of FIG. 13 is applicable to a wide variety of other plasmids and fragments. To further assist the reader, the steps shown in FIG. 13 have been assigned callout numbers 42 et seq. These callout numbers are cited in the following description. The techniques and DNA sequences of this invention are likely to be useful in the transformation of a wide variety of plants, including any plant which may be infected by one or more strains of A. tumefaciens or A. rhizogenes.

The NOS Promoter Region and 5' Non-Translated Region

The Applicants decided to obtain and utilize a nopaline synthase (NOS) promoter region to control the expression of the heterologous gene. The NOS is normally carried in certain types of Ti plasmids, such as pTiT37. Sciaky et al, 1978. The NOS promoter is normally inactive while in an A. tumefaciens cell. The entire NOS gene, including the promoter and the protein coding sequence, is within the T-DNA portion of a Ti plasmid that is inserted into the chromosomes of plant cells when a plant becomes infected and forms a crown gall tumor. Once inside the plant cell, the NOS promoter region directs RNA polymerase within a plant cell to transcribe the NOS protein coding sequence into mRNA, which is subsequently translated into the NOS enzyme.

Figure 12:
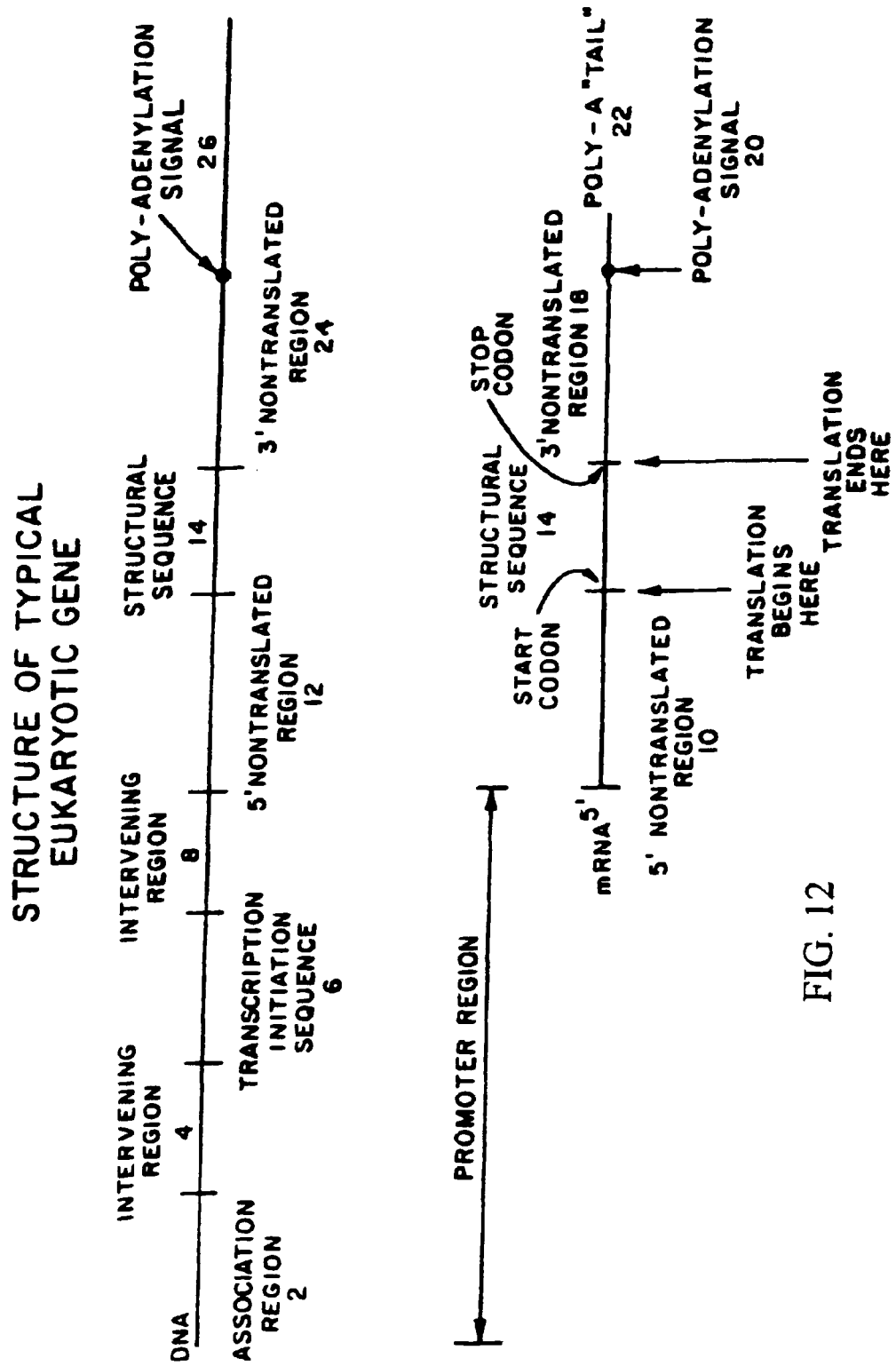
FIG. 12 represents the structure of a typical eukaryotic gene.

The boundaries between the different parts of a promoter region (shown in FIG. 12 as association region 2, intervening region 4, transcription initiation sequence 6, and intervening region 8), and the boundary between the promoter region and the 5' non-translated region, are not fully understood. The Applicants decided to utilize the entire promoter region and 5' non-translated region from the NOS gene, which is known to be expressed in plant cells. However, it is entirely possible that one or more of these sequences might be modified in various ways, such as alteration in length or replacement by other sequences. Such modifications in promoter regions and 5' non-translated regions have been studied in bacterial cells (see, e.g., Roberts et al 1979) and mammalian cells (see, e.g., McKnight, 1982). By utilizing the methodology taught by this invention, it is now possible to study the effects of modifications to promoter regions and 5' non-translated regions on the expression of genes in plant cells. It may be possible to increase the expression of a gene in a plant cell by means of such modifications. Such modifications, if performed upon chimeric genes of this invention, are within the scope of this invention.

Figure 14:
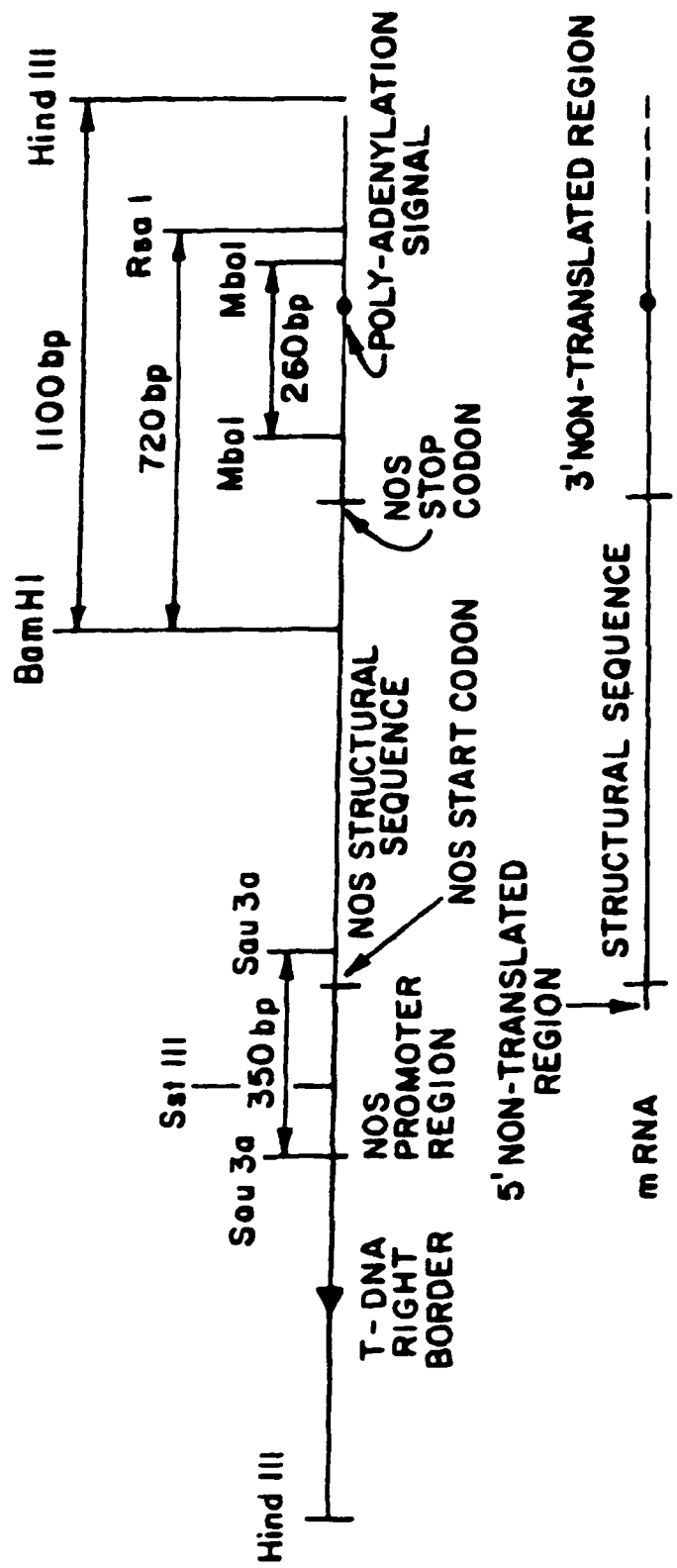
FIG. 14 represents fragment HindIII-23, obtained by digesting a Ti plasmid with HindIII.

A nopaline-type tumor-inducing plasmid, designated as pTiT37, was isolated from a strain of *A. tumefaciens* using standard procedures (Currier and Nester, 1976). It was digested with the endonuclease HindIII which produced numerous fragments. These fragments were separated by size on a gel, and one of the fragments was isolated and removed from the gel. This fragment was designated as the HindIII-23 fragment, because it was approximately the 23rd largest fragment from the Ti plasmid; it is approximately 3400 base pairs (bp) in size, also referred to as 3.4 kilobases (kb). From work by others (see, e.g., Hernalsteens et al, 1980), it was known that the HindIII-23 fragment contained the entire NOS gene, including the promoter region, a 5' non-translated region, a structural sequence with a start codon and a stop codon, and a 3' non-translated region. The HindIII-23 fragment is shown in FIG. 14.

By means of various cleavage and sequencing experiments, it was determined that the HindIII-23 fragment could be digested by another endonuclease, Sau3a, to yield a fragment, about 350 bp in size, which contains the entire NOS promoter region, the 5' non-translated region, and the first few codons of the NOS structural sequence. This fragment was sequenced, and the base sequence is represented in FIG. 15. The start codon (ATG) of the NOS structural sequence begins at base pair 301 within the 350 bp fragment. The Applicants decided to cleave the fragment between base pairs 300 and 301; this would provide them with a fragment about 300 base pairs long containing a NOS promoter region and the entire 5' non-translated region but with no translated bases. To cleave the 350 bp fragment at precisely the right location, the Applicants obtained an M13 clone designated as S1A, and utilized the procedure described below.

To create the S1A clone, Dr. Michael Bevan of Washington University converted the 350 bp Sau3a fragment into a single strand of DNA. This was done by utilizing a virus vector, designated as the M13 mp 2 phage, which goes through both double-stranded (ds) and single-stranded (ss) stages in its life cycle (Messing et al, 1981). The ds 350 bp fragment was inserted into the double-stranded replicative form DNA of the M13 mp 2, which had been cleaved with BamHI. The two fragments were ligated, and used to infect *E. coli* cells. The ds DNA containing the 350 bp inserted fragment subsequently replicated, and one strand (the viral strand) was encapsulated by the M13 viral capsid proteins. In one clone, designated the S1A, the orientation of the 350 bp fragment was such that the anti-sense strand (containing the same sequence as the mRNA) of the NOS gene was carried in the viral strand. Viral particles released from infected cells were isolated, and provided to the Applicants.

Single stranded S1A DNA, containing the anti-sense 350 bp fragment with the NOS promoter region, was isolated from the viral particles and sequenced. A 14-mer oligonucleotide primer was synthesized, using published procedures (Beaucage and Carruthers, 1981, as modified by Adams et al, 1982). This 14-mer was designed to be complementary to bases 287 through 300 of the 350 bp fragment, as shown on FIG. 15.

Figure 16:
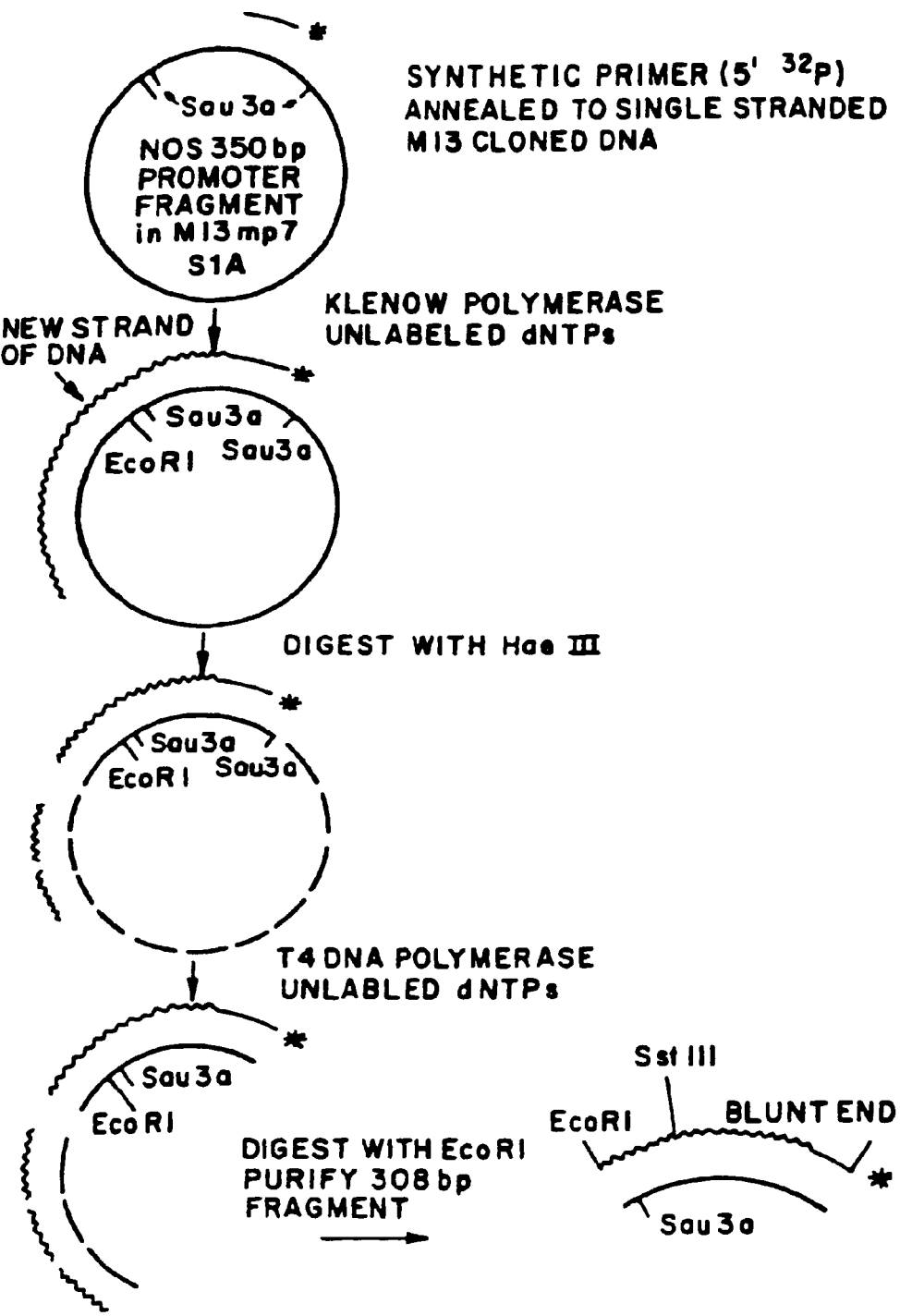
FIG. 16 represents the cleavage of a DNA sequence at a precise location, to obtain a DNA fragment which contains a NOS promoter region and complete 5' non-translated region.

The 5' end of the synthetic primer was radioactively labelled with $^{32}P$; this is represented in the figures by an asterisk Copies of the primer were mixed with copies of the single-stranded S1A DNA containing the anti-sense strand of the 350 bp fragment. The primer annealed to the desired region of the S1A DNA, as shown at the top of FIG. 5. After this occurred, Klenow DNA polymerase and a controlled quantity of unlabelled deoxy-nucleoside triphosphates (dNTP's), A, T, C, and G, were added. Klenow polymerase added nucleotides to the 3' (unlabelled) end of the primer, but not to the 5' (labelled) end. The result, as shown in FIG. 16, was a circular loop of single-stranded DNA, part of which was matched by a second strand of DNA. The 5' end of the second strand was located opposite base #300 of the Sau3a insert The partially double-stranded DNA was then digested by a third endonuclease, HaeIII, which can cleave both single-stranded and double-stranded DNA. HaeIII cleavage sites were known to exist in several locations outside the 350 bp insert, but none existed inside the 350 bp insert. This created a fragment having one blunt end, and one 3' overhang which started at base #301 of the Sau3a insert.

The HaeIII fragment mixture was treated with T4 DNA polymerase and unlabelled dNTP's. This caused the single stranded portion of the DNA, which extended from base #301 of the Sau3a insert to the closest HaeIII cleavage site, to be removed from the fragment. In this manner, the ATG start codon was removed from base pair #300, leaving a blunt end double-stranded fragment which was approximately 550 bp long.

The mixture was then digested by a fourth endonuclease EcoRI, which cleaved the 550 bp fragment at a single site outside the NOS promoter region. The fragments were then separated by size on a gel, and the radioactively-labelled fragment was isolated. This fragment contained the entire NOS promoter region and 5' non-translated region. It had one blunt end with a sequence of

5'... CTGCA

... GACGT and one cohesive end (at the EcoRI site) with a sequence of The shorter strand was about 308 bp long.

The foregoing steps are represented in FIG. 2 as steps 42, 44, and 46.

This fragment was inserted into pMON40 (which is described below) to obtain pMON58, as shown on FIG. 13.

Creation of Plasmid with NPTII Gene (pMON40)

Figure 17:
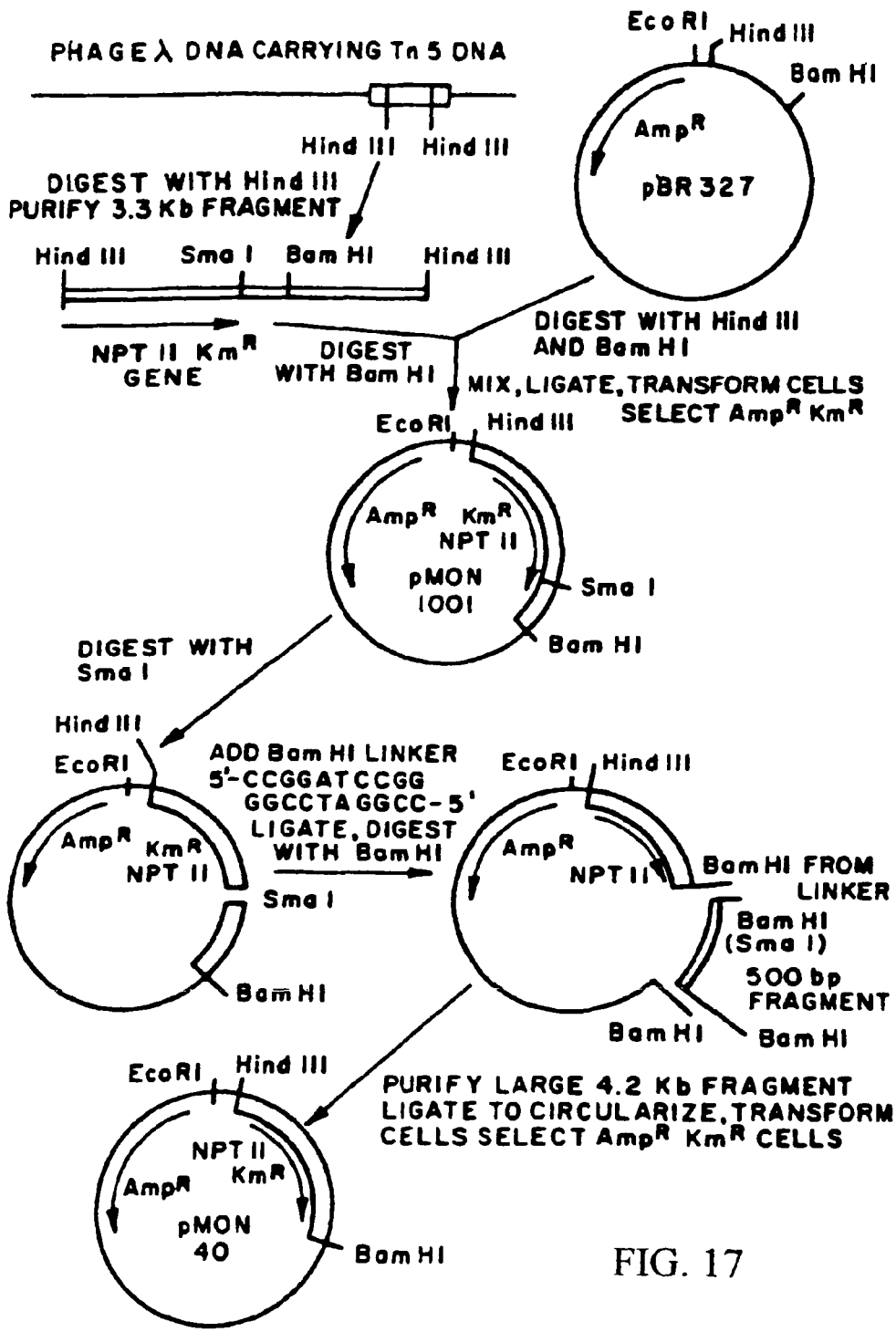
FIG. 17 represents the creation of plasmids pMON1001 and pMON40, which contain an NPTII structural sequence.

A bacterial transposon, designated as Tn5, is known to contain a complete NPTII gene, including promoter region, structural sequence, and 3' non-translated region. The NPTII enzyme inactivates certain aminoglycoside antibiotics, such as kanamycin, neomycin, and G418; see Jimenez and Davies, 1980. This gene is contained within a 1.8 kb fragment, which can be obtained by digesting phage lambda bbkan-1 DNA (D. Berg et al, 1975) with two endonucleases, HindIII and BamHI. This fragment was inserted into a common laboratory plasmid, pBR327, which had been digested by HindIII and BamHI. As shown in FIG. 17, the resulting plasmid was designated as pMON1001, which was about 4.7 kb.

To reduce the size of the DNA fragment which carried the NPTII structural sequence, the Applicants eliminated about 500 bp from the pMON1001 plasmid, in the following manner. First, they digested pMON1001 at a unique SmaI restriction site which was outside of the NPTII gene. Next, they inserted a 10-mer synthetic oligonucleotide linker,

```
5'CCGGATCCGG,

GGCCTAGGCC
``` into the SmaI cleavage site. This eliminated the SmaI cleavage site and replaced it with a BamHI cleavage site. A second BamHI cleavage site already existed, about 500 bp from the new BamHI site. The Applicants digested the plasmid with BamHI, separated the 500 bp fragment from the 4.2 kb fragment, and circularized the 4.2 kb fragment. The resulting plasmids were inserted into *E. coli*, which were then selected for resistance to ampicillin and kanamycin. A clonal colony of *E. coli* was selected; these cells contained a plasmid which was designated as pMON40, as shown in FIG. 17.

The foregoing steps are represented in FIG. 13 as steps 48 and 50.

Insertion of NOS Promoter into Plasmid pMON40

The Applicants deleted the NPTII promoter from pMON40, and replaced it with the NOS promoter fragment described previously, by the following method, shown on FIG. 18.

Previous cleavage and sequencing experiments (Rao and Rogers, 1979; Auerswald et al, 1980) indicated that a BglII cleavage site existed in the NPTII gene between the promoter region and the structural sequence. Plasmid pMON40 was digested with BglII. The cohesive ends were then filled in by mixing the cleaved plasmid with Klenow polymerase and the four dNTP's, to obtain the following blunt ends:

```
5'      - AGATC      GATCT-
        - TCTAG      CTAGA-5'
```

The polymerase and dNTP's were removed, and the cleaved plasmid was then digested with EcoRI. The smaller fragment which contained the NPTII promoter region was removed, leaving a large fragment with one EcoRI end and one blunt end. This large fragment was mixed with the 308 bp fragment which contained the NOS promoter, described previously and shown on FIG. 5. The fragments were ligated, and inserted into *E. coli*. *E. coli* clones were selected for ampicillin resistance. Replacement of the NPTII promoter region (a bacterial promoter) with the NOS promoter region (which is believed to be active only in plant cells) caused the NPTII structural sequence to become inactive in *E. coli*. Plasmids from 36 kanamycin-sensitive clones were obtained; the plasmid from one clone, designated as pMON58, was utilized in subsequent work.

The foregoing steps are represented in FIG. 13 as steps 52 and 54.

Plasmid pMON58 may be digested to obtain a 1.3 kb EcoRI-BamHI fragment which contains the NOS promoter region, the NOS 5' non-translated region, and the NPTII structural sequence. This step is represented in FIG. 13 as step 56.

Insertion of NOS 3' Sequence into NPTII Gene

As mentioned above in "Background Art", the functions of 3' non-translated regions in eukaryotic genes are not fully understood. However, they are believed to contain at least one important sequence, a poly-adenylation signal.

It was suspected by the Applicants that a gene having a bacterial 3' non-translated region might not be expressed as effectively in a plant cell as the same gene having a 3' non-translated region from a gene, such as NOS, which is known to be expressed in plants.

Therefore, the Applicants decided to add a NOS 3' non-translated region to the chimeric gene, in addition to the NPTII 3' non-translated region already present. Whether a different type of 3' non-translated region (such as a 3' region from an octopine-type or agropine-type Ti plasmid, or a 3' region from a gene that normally exists in a plant cell) would be suitable or preferable for use in any particular type of chimeric gene, for use in any specific type of plant cell, may be determined by those skilled in the art through routine experimentation using the method of this invention. Alternately, it is possible, using the methods described herein, to delete the NPTII or other existing 3' non-translated region and replace it with a desired 3' non-translated region that is known to be expressed in plant cells.

Those skilled in the art may also determine through routine experimentation whether the 3' non-translated region that naturally follows a structural sequence that is to be inserted into a plant cell will enhance the efficient expression of that structural sequence in that type of plant cell. If so, then the steps required to insert a different 3' non-translated region into the chimeric gene might not be required in order to perform the method of this invention.

In order to obtain a DNA fragment containing a NOS 3' non-translated region appropriate for joining to the NPTII structural sequence from pMON58 (described previously), the Applicants utilized a 3.4 kb HindIII-23 fragment from a Ti plasmid, shown on FIG. 14. This 3.4 kb fragment was isolated and digested with BamHI to obtain a 1.1 kb BamHI-HindIII fragment containing a 3' portion of the NOS structural sequence (including the stop codon), and the 3' non-translated region of the NOS gene (including the poly-adenylation signal). This 1.1 kb fragment was inserted into a pBR327 plasmid which had been digested with HindIII and BamHI. The resulting plasmid was designated as pMON42, as shown on FIG. 19.

Plasmid pMON42 was digested with BamHI and RsaI, and a 720 bp fragment containing the desired NOS 3' non-translated region was purified on a gel. The 720 bp fragment was digested with another endonuclease, MboI, and treated with the large fragment of *E. coli* DNA polymerase I. This resulted in a 260 bp fragment with MboI blunt ends, containing a large part of the NOS 3' non-translated region including the poly-A signal.

The foregoing procedure is represented in FIG. 13 by step 58. However, it is recognized that alternate means could have been utilized; for example, it might have been possible to digest the HindIII-23 fragment directly with MboI to obtain the desired 260 bp fragment with the NOS 3' non-translated region.

Assembly of Chimeric Gene

To complete the assembly of the chimeric gene, it was necessary to ligate the 260 bp MboI fragment (which contained the NOS 3' non-translated region) to the 1.3 kb EcoRI-BamHI fragment from pMON58 (which contained the NOS promoter region and 5' non-translated region and the NPTII structural sequence). In order to facilitate this ligation and control the orientation of the fragments, the Applicants decided to convert the MboI ends of the 260 bp fragment into a BamHI end (at the 5' end of the fragment) and an EcoRI end (at the 3' end of the fragment). In order to perform this step, the Applicants used the following method.

Figure 19:
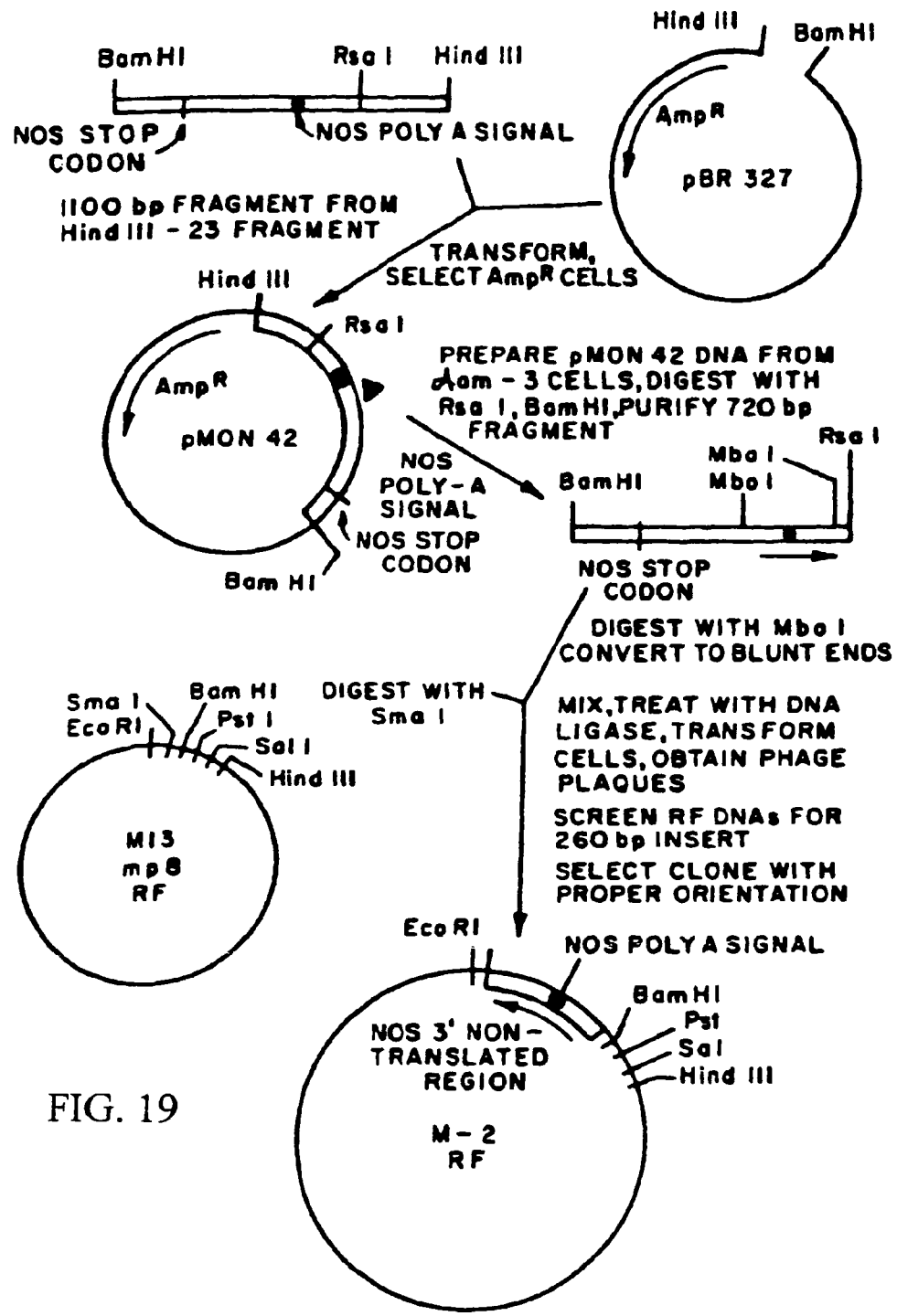
FIG. 19 represents the creation of an M13 derivative designated as M-2, which contains a NOS 3' non-translated region and poly-A signal.

The 260 bp MboI fragment, the termini of which had been converted to blunt ends by Klenow polymerase, was inserted into M13 mp 8 DNA at a SmaI cleavage site. The SmaI site is surrounded by a variety of other cleavage sites present in the M13 mp 8 DNA, as shown in FIG. 19. The MboI fragment could be inserted into the blunt SmaI ends in either orientation. The orientation of the MboI fragments in different clones were tested, using HinfI cleavage sites located assymetrically within the MboI fragment. A clone was selected in which the 3' end of the NOS 3' non-translated region was located near the EcoRI cleavage site in the M13 mp 8 DNA. This clone was designated as the M-2 clone, as shown in FIG. 19.

Figure 20:
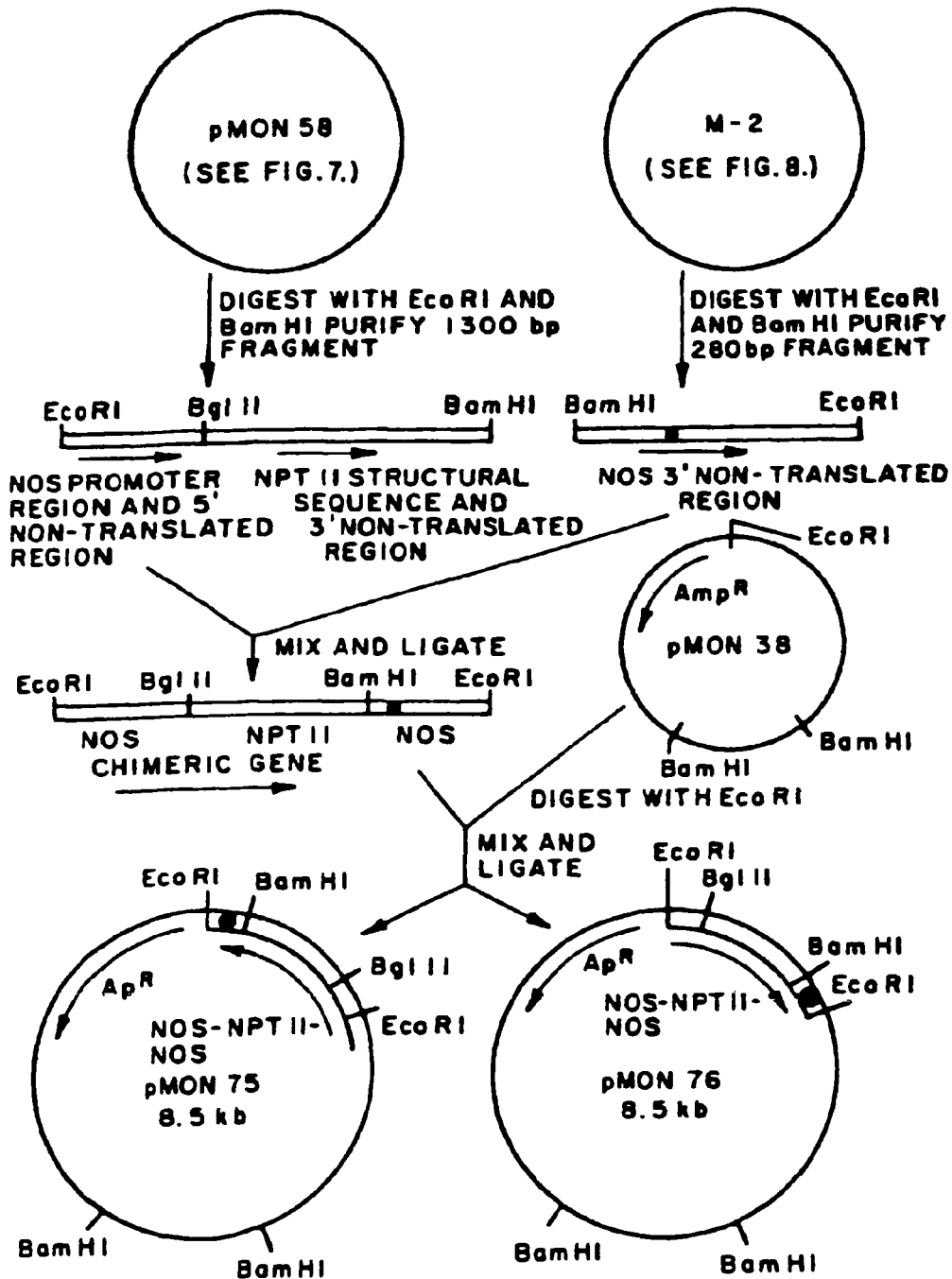
FIG. 20 represents the assembly of the NOS-NPTII-NOS chimeric gene, and the insertion of the chimeric gene into plasmid pMON38 to obtain plasmids pMON75 and pMON76.

Replicative form (double stranded) DNA from the M-2 clone was digested by EcoRI and BamHI and a 280 bp fragment was isolated. Separately, plasmid pMON58 was digested by EcoRI and BamHI, and a 1300 bp fragment was isolated. The two fragments were ligated, as shown in FIG. 20, to complete the assembly of a NOS-NPTII-NOS chimeric gene having EcoRI ends.

There are a variety of ways to control the ligation of the two fragments. For example, the two EcoRI-BamHI fragments could be joined together with DNA ligase and cleaved with EcoRI. After inactivation of EcoRI, a vector molecule having EcoRI ends that were treated with calf alkaline phosphatase (CAP) may be added to the mixture. The fragments in the mixture may be ligated in a variety of orientations. The plasmid mixture is used to transform *E. coli*, and cells having plasmids with the desired orientation are selected or screened, as described below.

A plasmid, designated as pMON38, was created by insertion of the HindIII-23 fragment (from Ti plasmid pTiT37) into the HindIII cleavage site of the plasmid pBR327. Plasmid pMON38 contains a unique EcoRI site, and an ampicillin-resistance gene which is expressed in *E. coli*. Plasmid pMON38 was cleaved with EcoRI and treated with alkaline phosphatase to prevent it from re-ligating to itself. U.S. Pat. No. 4,264,731 (Shine, 1981). The resulting fragment was mixed with the 1300 bp NOS-NPTII fragment from pMON58, and the 280 bp NOS fragment from M-2, which had been ligated and EcoRI-cleaved as described in the previous paragraph. The fragments were ligated, and inserted into *E. coli*. The *E. coli* cells which had acquired intact plasmids with ampicillin-resistance genes were selected on plates containing ampicillin. Several clones were selected, and the orientation of the inserted chimeric genes was evaluated by means of cleavage experiments. Two clones having plasmids carrying NOS-NPTII-NOS inserts with opposite orientations were selected and designated as pMON75 and pMON76, as shown in FIG. 20. The chimeric gene may be isolated by digesting either pMON75 or pMON76 with EcoRI and purifying a 1580 bp fragment.

The foregoing procedure is represented on FIG. 13 by step 60.

This completes the discussion of the NOS-NPTII-NOS chimeric gene. Additional information on the creation of this gene is provided in the Examples. A copy of this chimeric gene is contained in plasmid pMON128; it may be removed from pMON128 by digestion with EcoRI. A culture of *E. coli* containing pMON128 has been deposited with the American Type Culture Collection; this culture has been assigned accession number 39264.

To prove the utility of this chimeric gene, the Applicants inserted it into plant cells. The NPTII structural sequence was expressed in the plant cells, causing them and their descendants to acquire resistance to concentrations of kanamycin which are normally toxic to plant cells.

In an alternate preferred embodiment of this invention, a chimeric gene was created comprising (1) a NOS promoter region and 5' non-translated region, (2) a structural sequence which codes for NPTI, and (3) a NOS 3' non-translated region. NPTI and NPTII are different and distinct enzymes with major differences in their amino acid sequences and substrate specificities. See, e.g., E. Beck et al, 1982. The relative stabilities and activities of these two enzymes in various types of plant cells are not yet fully understood, and NPTI may be preferable to NPTII for use in certain types of experiments and plant transformations.

Figure 21:
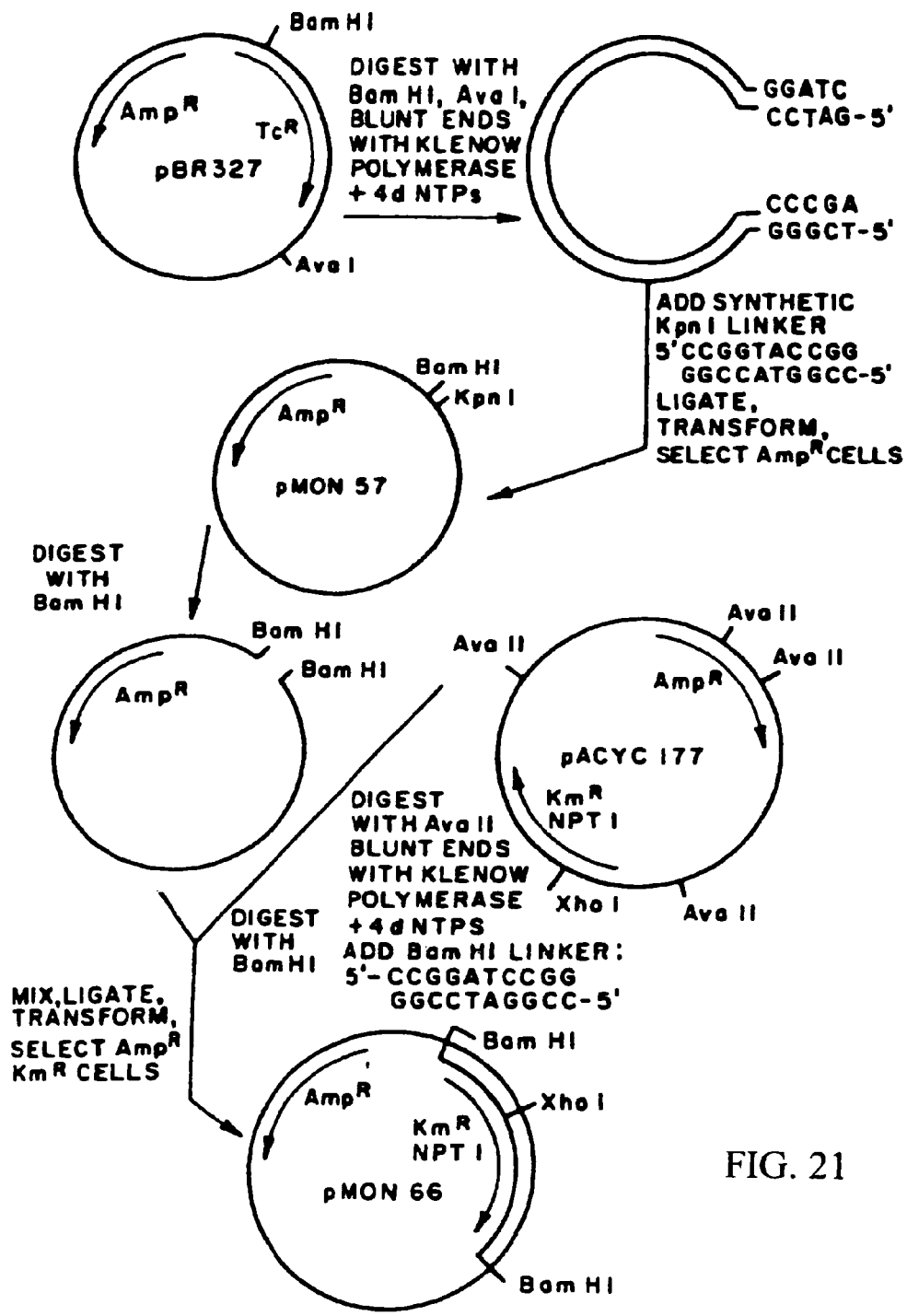
FIG. 21 represents the creation of plasmid pMON66, which contains an NPTI gene.

A 1200 bp fragment containing an entire NPTI gene was obtained by digesting pACYC177 (Chang and Cohen, 1978) with the endonuclease, AvaII. The AvaII termini were converted to blunt ends with Klenow polymerase, and converted to BamHI termini using a synthetic linker. This fragment was inserted into a unique BamHI site in a pBR327-derived plasmid, as shown in FIG. 21. The resulting plasmid was designated as pMON66.

Plasmid pMON57 (a deletion derivative of pBR327, as shown in FIG. 21) was digested with AvaII. The 225 bp fragment of pMON57 was replaced by the analogous 225 bp AvaII fragment taken from plasmid pUC8 (Vieira and Messing, 1982), to obtain a derivative of pMON57 with no PstI cleavage sites. This plasmid was designated as pMON67.

Plasmid pMON58 (described previously and shown in FIG. 18) was digested with EcoRI and BamHI to obtain a 1300 bp fragment carrying the NOS promoter and the NPTII structural sequence.

Figure 22:
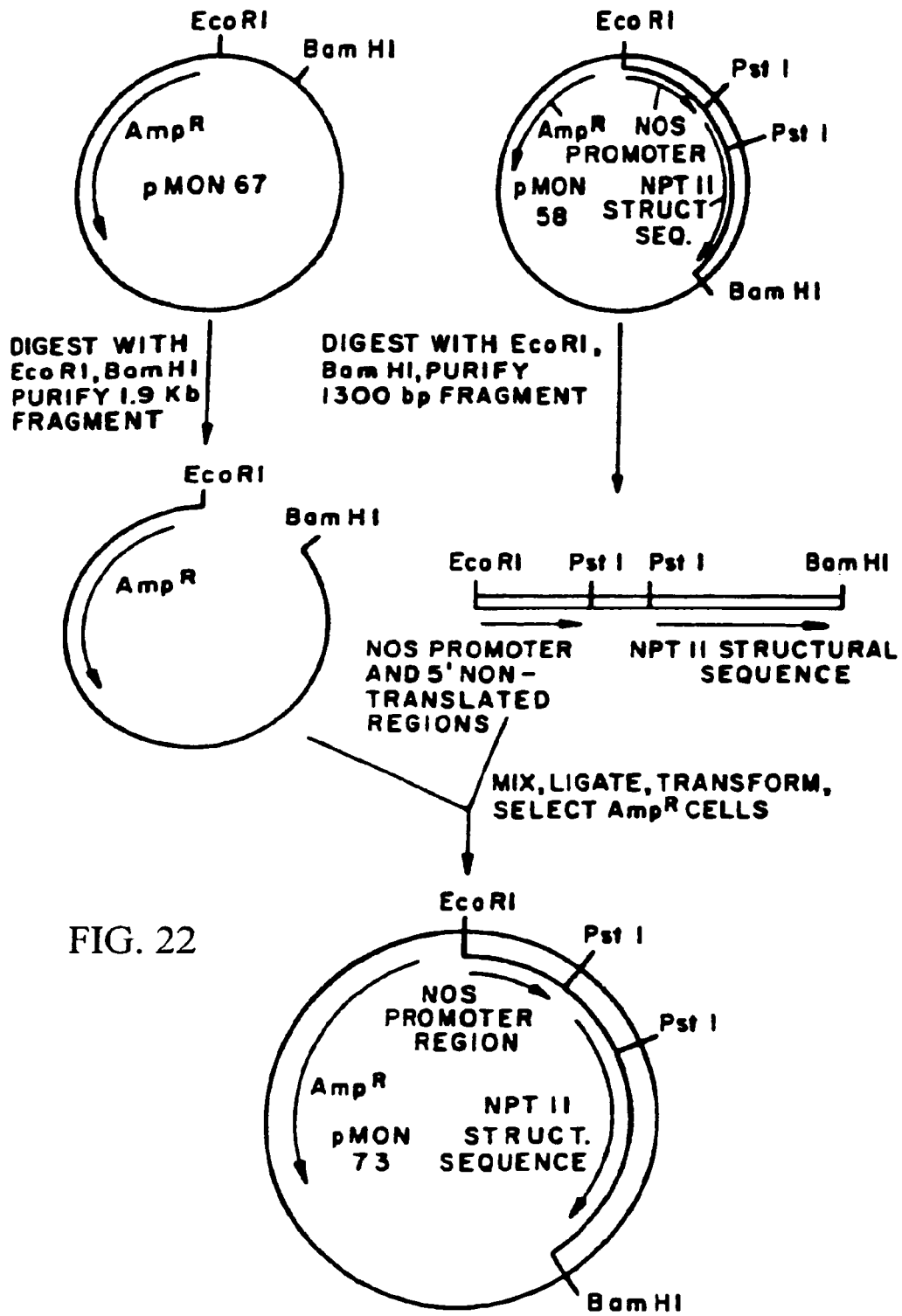
FIG. 22 represents the creation of plasmid pMON73, containing a chimeric NOS-NPTII sequence.
Figure 23:
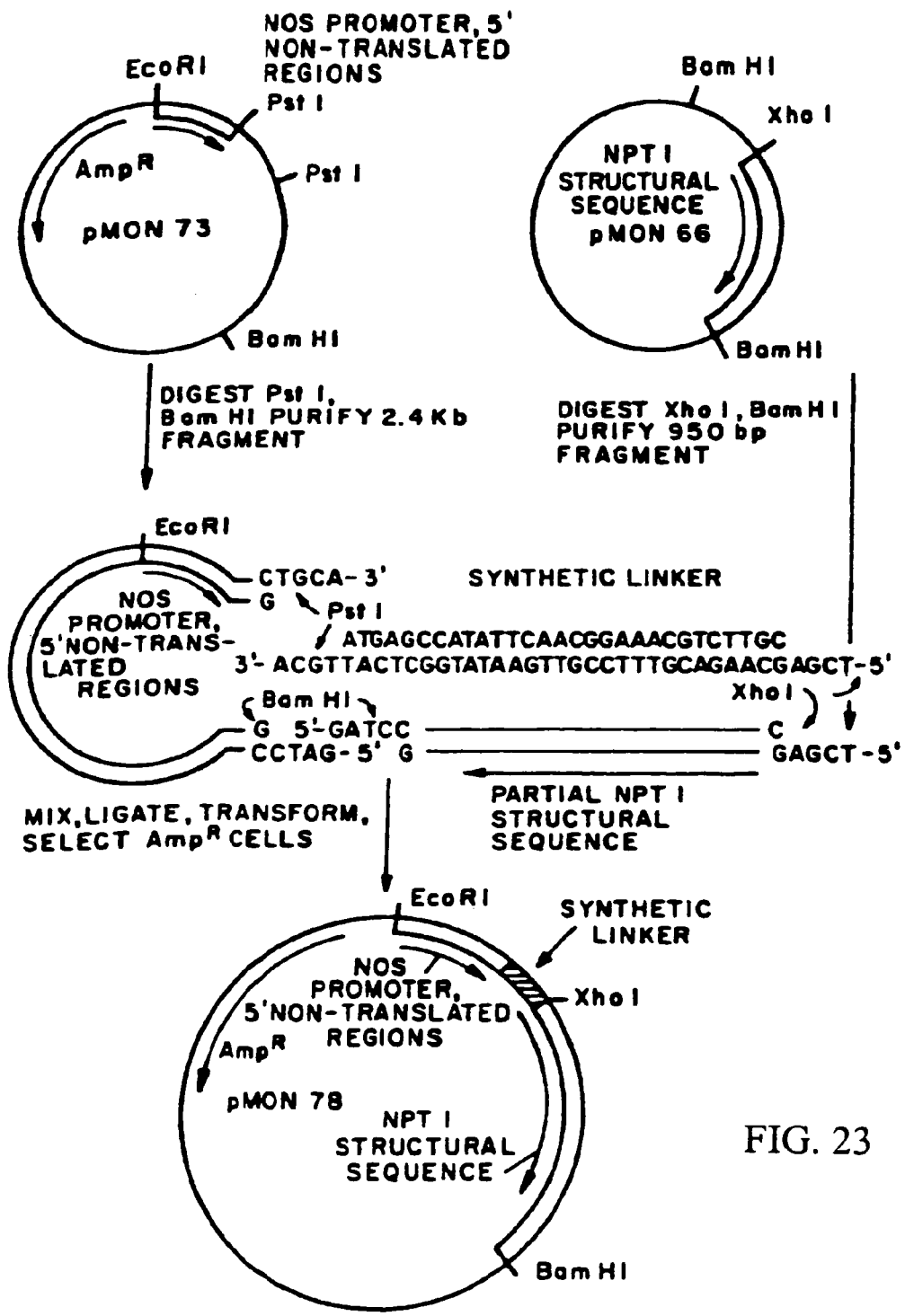
FIG. 23 represents the creation of plasmid pMON78, containing a chimeric NOS-NPTI sequence.

This fragment was inserted into pMON67 which had been digested with EcoRI and BamHI. The resulting plasmid was designated as pMON73, as shown in FIG. 22.

pMON73 was digested with PstI and BamHI, and a 2.4 kb fragment was isolated containing a NOS promoter region and 5' non-translated region. Plasmid pMON66 (shown on FIG. 21) was digested with XhoI and BamHI to yield a 950 bp fragment containing the structural sequence of NPTI. This fragment lacked about 30 nucleotides at the 5' end of the structural sequence. A synthetic linker containing the missing bases, having appropriate PstI and XhoI ends, was created. The pMON73 fragment, the pMON66 fragment, and the synthetic linker were ligated together to obtain plasmid pMON78, as shown in FIG. 13. This plasmid contains the NOS promoter region and 5' non-translated region adjoined to the NPTI structural sequence. The ATG start codon was in the same position that the ATG start codon of the NOS structural sequence had occupied.

Figure 24:
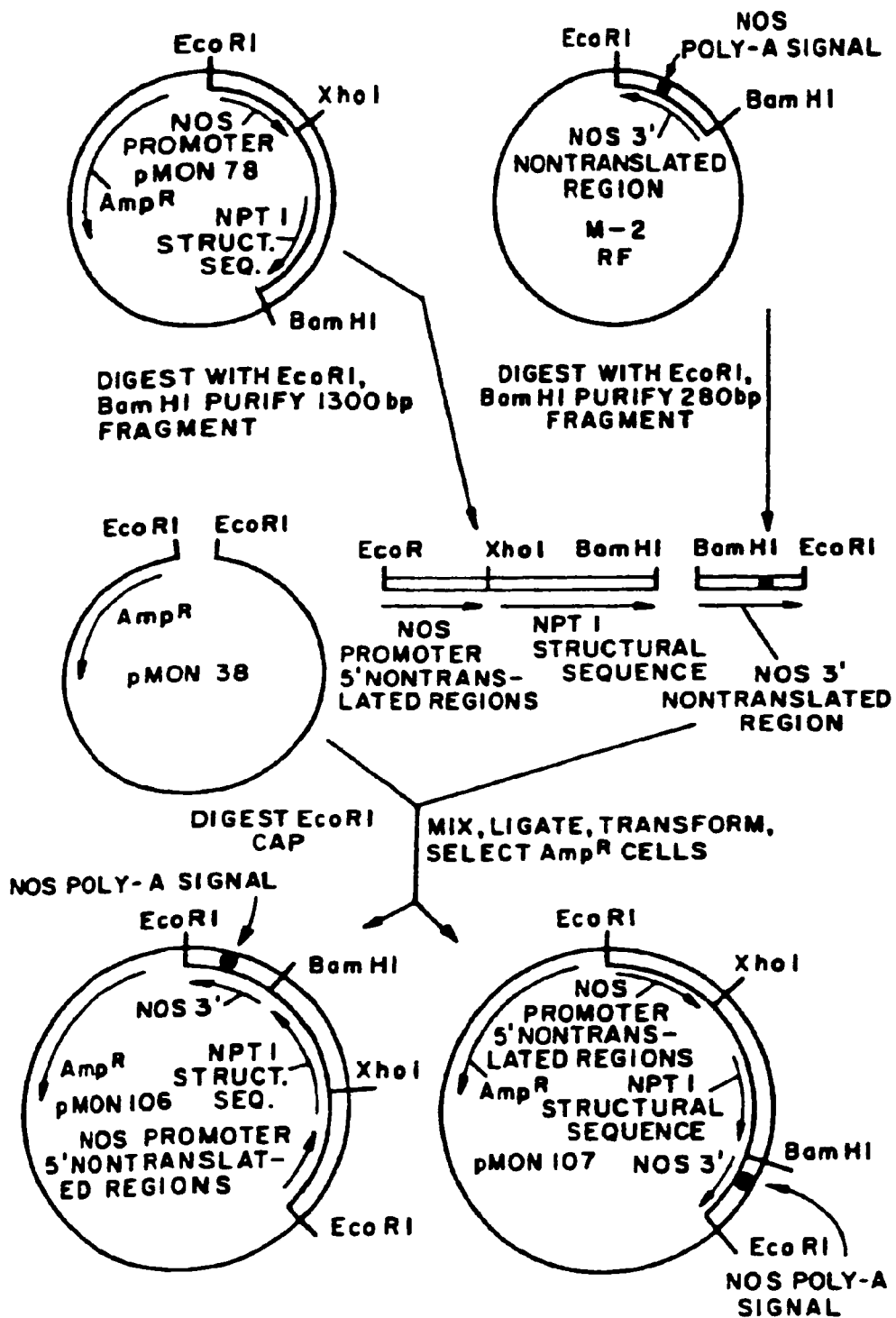
FIG. 24 represents the creation of plasmids pMON106 and pMON107, which contain chimeric NOS-NPTI-NOS genes.

Plasmid pMON78 was digested with EcoRI and BamHI to yield a 1300 bp fragment carrying the chimeric NOS-NPTI regions. Double-stranded DNA from the M-2 clone (described previously and shown on FIG. 20) was digested with EcoRI and BamHI, to yield a 280 bp fragment carrying a NOS 3' non-translated region with a poly-adenylation signal. The two fragments described above were ligated together to create the NOS-NPTI-NOS chimeric gene, which was inserted into plasmid pMON38 (described above) which had been digested with EcoRI. The two resulting plasmids, having chimeric gene inserts with opposite orientations, were designated as pMON106 and pMON107, as shown in FIG. 24.

Figure 25:
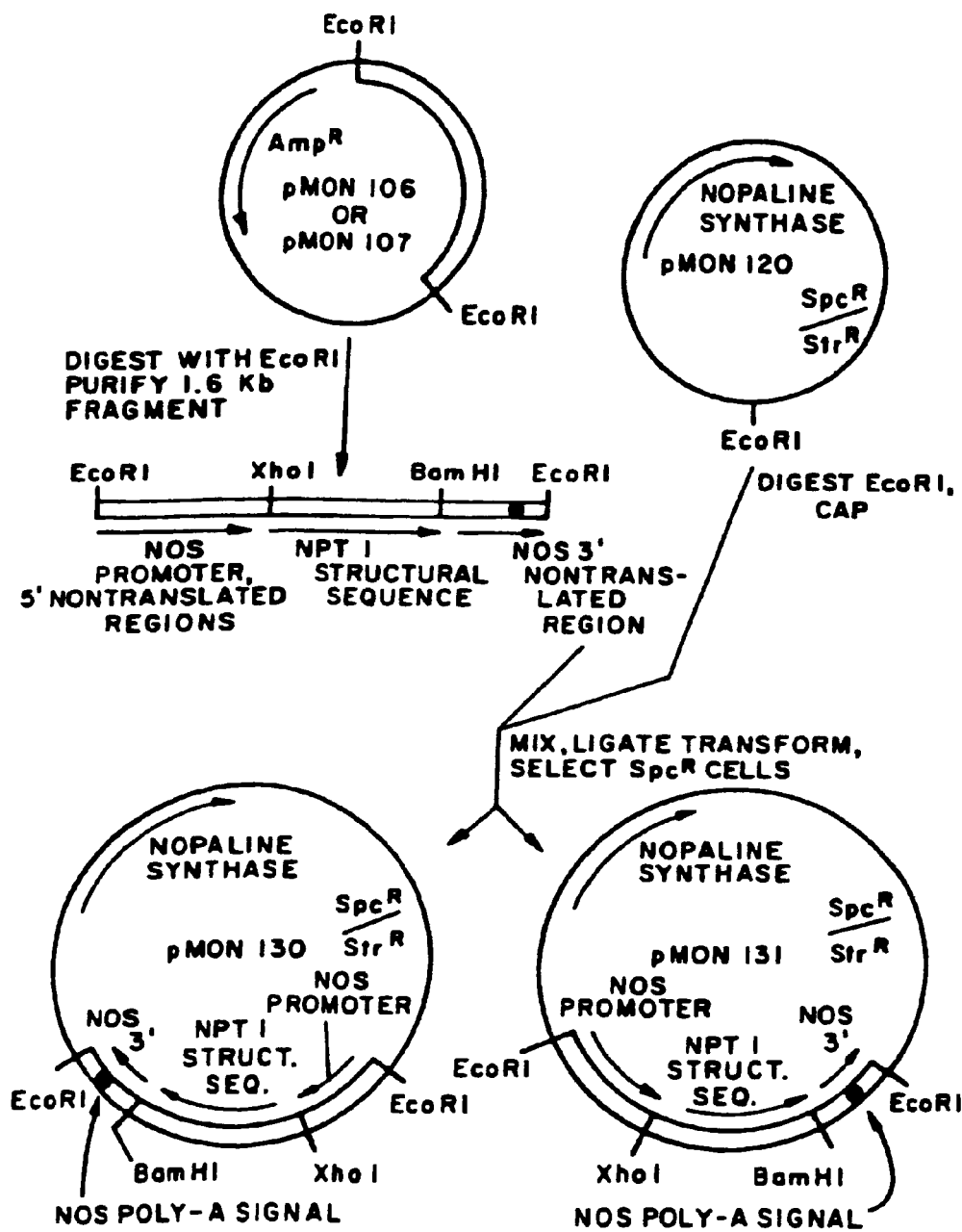
FIG. 25 represents the insertion of a chimeric NOS-NPTI-NOS gene into pMON120 to obtain plasmids pMON130 and pMON131.

Either of plasmids pMON106 or pMON107 may be digested with EcoRI to yield a 1.6 kb fragment containing the chimeric NOS-NPTI-NOS gene. This fragment was inserted into plasmid pMON120 which had been digested with EcoRI and treated with alkaline phosphatase. The resulting plasmids, having inserts with opposite orientations, were designated as pMON130 and pMON131, as shown on FIG. 25.

The NOS-NPTI-NOS chimeric gene was inserted into plant cells, which acquired resistance to kanamycin. This demonstrates expression of the chimeric gene in plant cells.

Creation of Chimeric Gene with Soybean Promoter

In an alternate preferred embodiment of this invention, a chimeric gene was created comprising (1) a promoter region and 5' non-translated region taken from a gene which naturally exists in soybean; this gene codes for the small subunit of ribulose-1,5-bis-phosphate carboxylase (sbss for soybean small subunit); (2) a structural sequence which codes for NPTII, and (3) a NOS 3' non-translated region.

The sbss gene codes for a protein in soybean leaves which is involved in photosynthetic carbon fixation. The sbss protein is the most abundant protein in soybean leaves (accounting for about 10% of the total leaf protein), so it is likely that the sbss promoter region causes prolific transcription.

Figure 26:
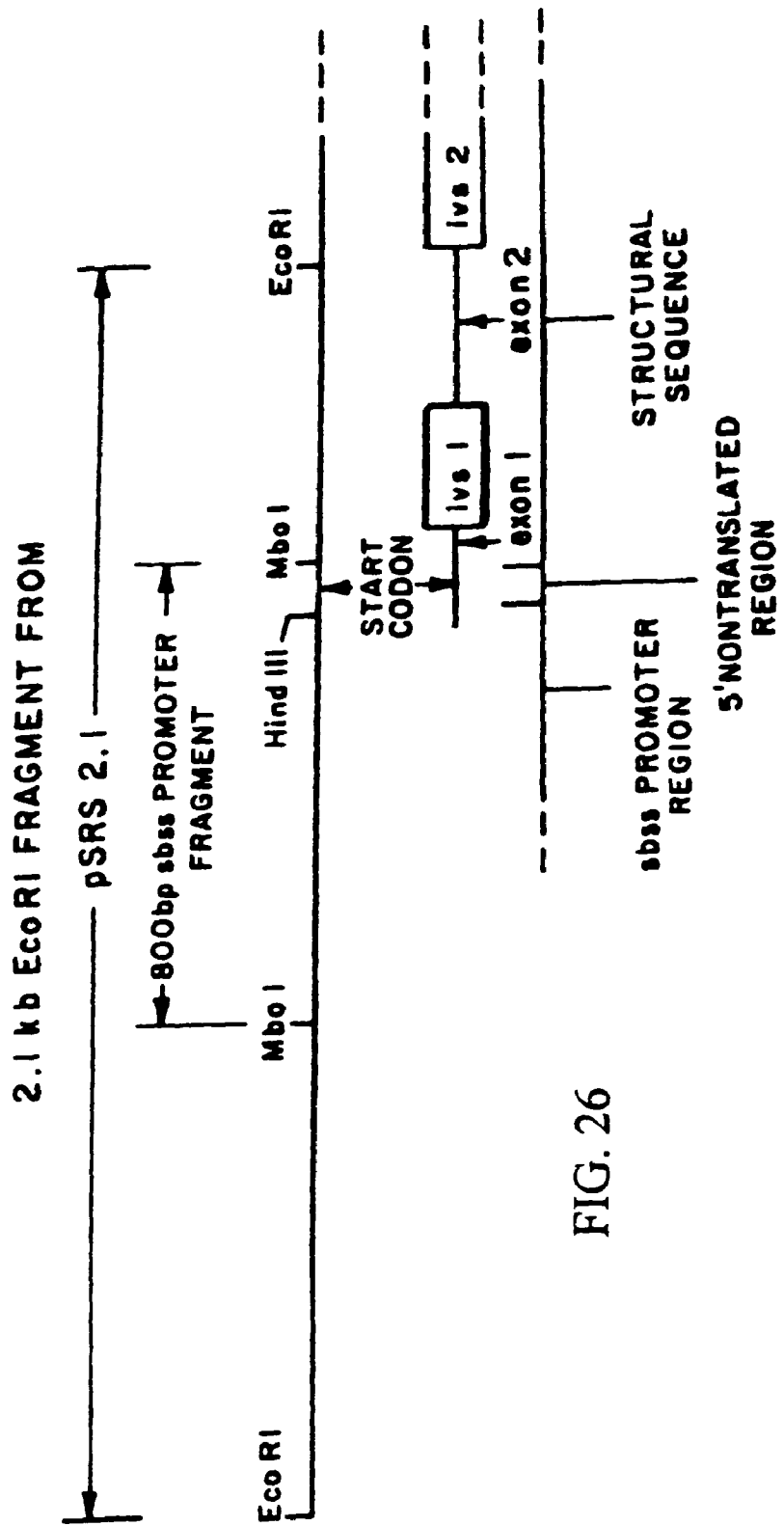
FIG. 26 represents the structure of a DNA fragment containing a soybean protein (sbss) promoter.

There are believed to be approximately six genes encoding the ss RuBPCase protein in the soybean genome. One of the members of the ss RuBPCase gene family, SRS1, which is highly transcribed in soybean leaves, has been cloned and characterized. The promoter region, 5' nontranslated region, and a portion of the structural sequence are contained on a 2.1 kb EcoRI fragment that was subcloned into the EcoRI site of plasmid pBR325 (Bolivar, 1978). The resultant plasmid, pSRS2.1, was a gift to Monsanto Company from Dr. R. B. Meagher, University of Georgia, Athens, Ga. The 2.1 kb EcoRI fragment from pSRS2.1 is shown on FIG. 26.

Figure 27:
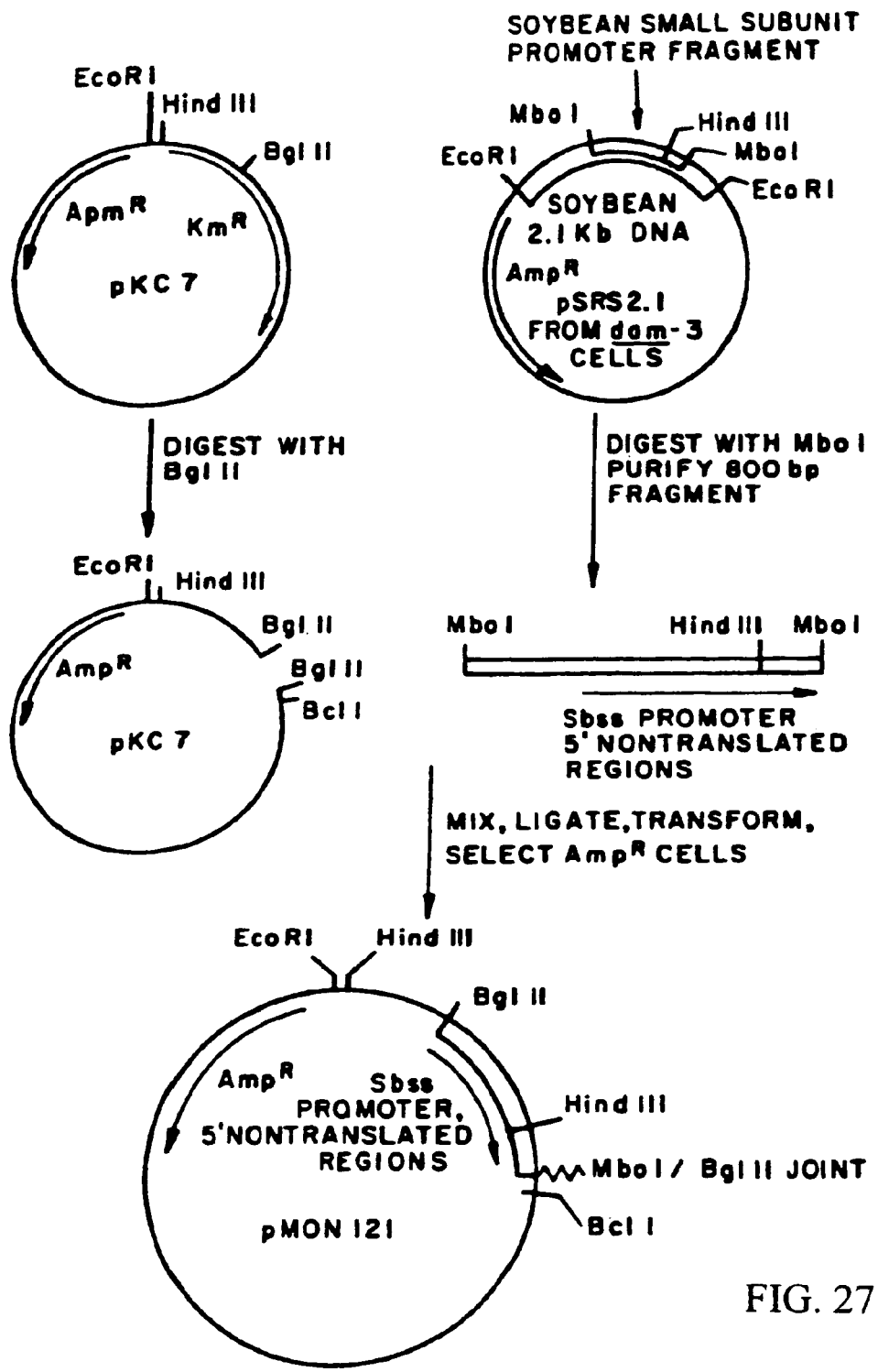
FIG. 27 represents the creation of plasmid pMON121, containing the sbss promoter.

Plasmid pSRS2.1 was prepared from dam—*E. coli* cells, and cleaved with MboI to obtain an 800 bp fragment. This fragment was inserted into plasmid pKC7 (Rao and Rogers, 1979) which had been cleaved with BglII. The resulting plasmid was designated as pMON121, as shown on FIG. 27.

Figure 28:
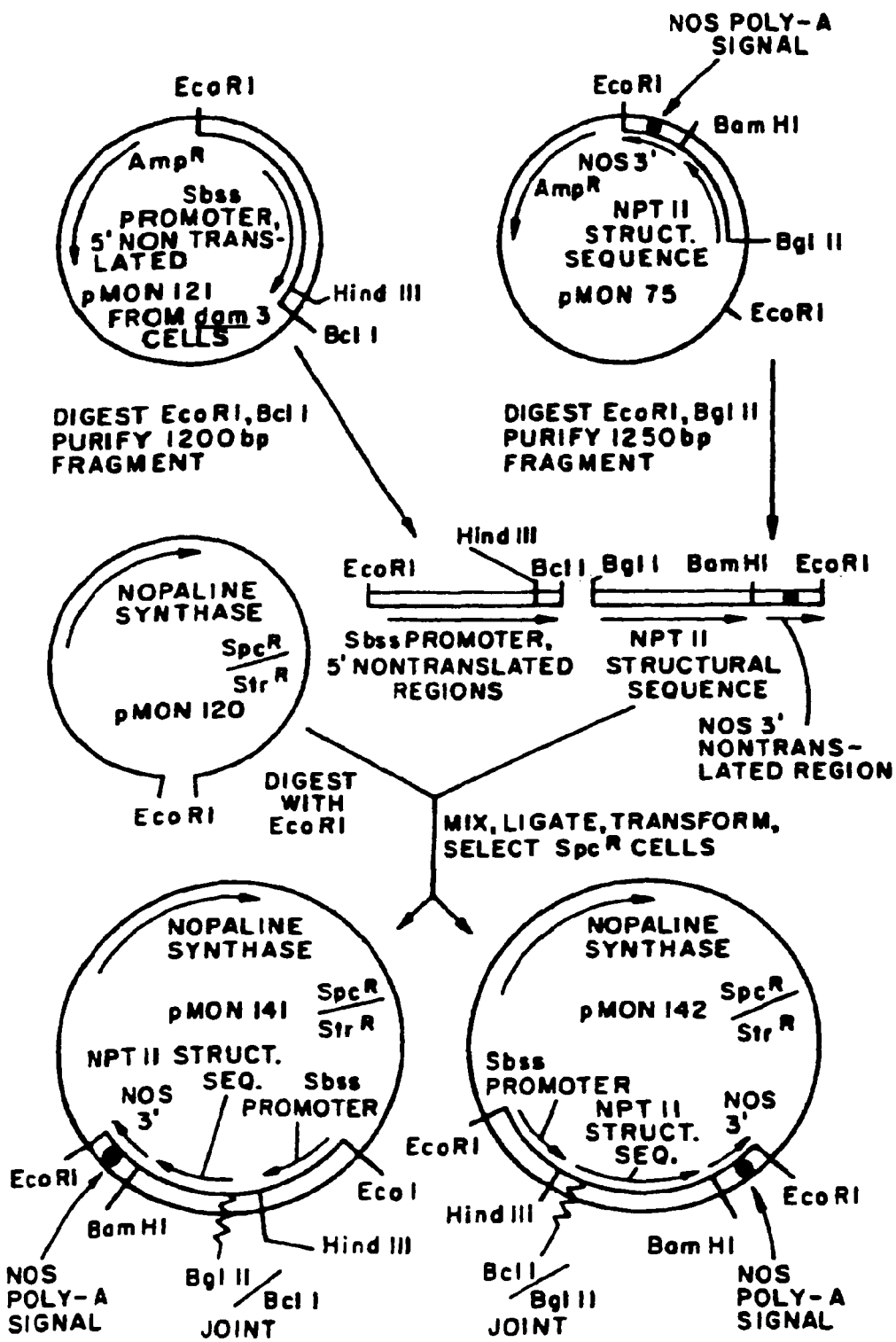
FIG. 28 represents the insertion of a chimeric sbss-NPTII-NOS gene into pMON120 to create plasmids pMON141 and pMON142.

Plasmid pMON121 was digested with EcoRI and Bcl1, and a 1200 bp fragment containing the sbss promoter region was isolated. Separately, plasmid pMON75 (described previously and shown on FIG. 20) was digested with EcoRI and BglII, and a 1250 bp fragment was isolated, containing a NPTII structural sequence and a NOS 3' non-translated region. The two fragments were ligated at the compatible Bcl1/BglII overhangs, to create a 2450 bp fragment containing sbss-NPTII-NOS chimeric gene. This fragment was inserted into pMON120 which had been cleaved with EcoRI, to create two plasmids having chimeric gene inserts with opposite orientations, as shown in FIG. 28. The plasmids were designated as pMON141 and pMON142.

The sbss-NPTII-NOS chimeric genes were inserted into several types of plant cells, causing the plant cells to acquire resistance to kanamycin.

This successful transformation proved that a promoter region from one type of plant can cause the expression of a gene within plant cells from an entirely different genus, family, and order of plants.

The chimeric sbss-NPTII-NOS gene also had another significant feature. Sequencing experiments indicated that the 800 bp MboI fragment contained the ATG start codon of the sbss structural sequence. Rather than remove this start codon, the Applicants decided to insert a stop codon behind it in the same reading frame.

This created a dicistronic mRNA sequence, which coded for a truncated amino portion of the sbss polypeptide and a complete NPTII polypeptide. Expression of the NPTII polypeptide was the first proof that a dicistronic mRNA can be translated within plant cells.

The sbss promoter is contained in plasmid pMON154, described below. A culture of *E. coli* containing this plasmid has been deposited with the American Type Culture Center. This culture has been assigned accession number 39265.

Creation of BGH Chimeric Genes

In an alternate preferred embodiment of this invention, a chimeric gene was created comprising (1) a sbss promoter region and 5' non-translated region, (2) a structural sequence which codes for bovine growth hormone (BGH) and (3) a NOS 3' non-translated region. This chimeric gene was created as follows.

Figure 29:
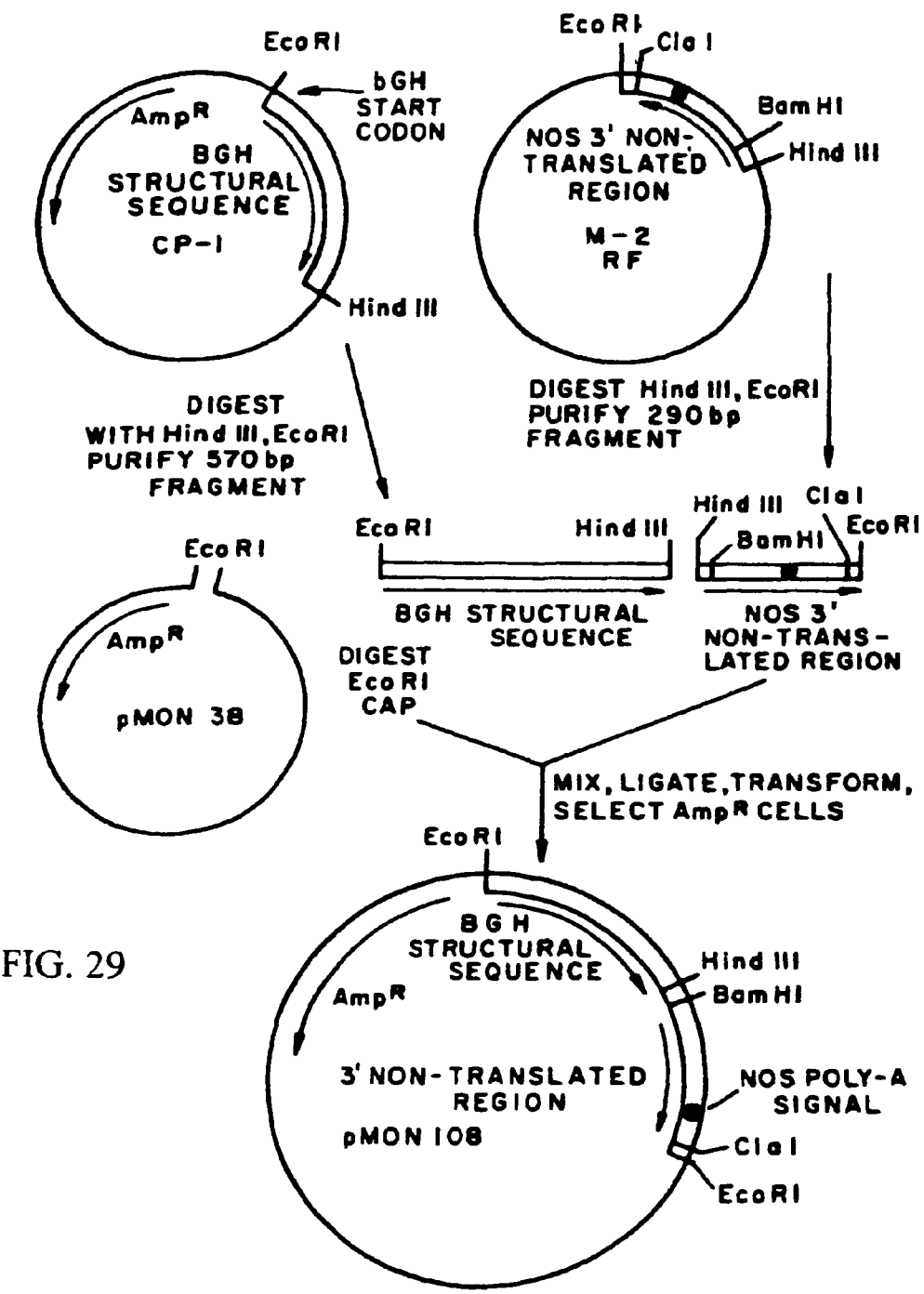
FIG. 29 represents the creation of plasmid pMON108, containing a bovine growth hormone structural sequence and a NOS 3' region.

A structural sequence which codes for the polypeptide, bovine growth hormone, (see, e.g., Woychik et al, 1982) was inserted into a pBR322-derived plasmid. The resulting plasmid was designated as plasmid CP-1. This plasmid was digested with EcoRI and HindIII to yield a 570 bp fragment containing the structural sequence. Double stranded M-2 RF DNA (described previously and shown in FIG. 19) was cleaved with EcoRI and HindIII to yield a 290 bp fragment which contained the NOS 3' non-translated region with a poly-adenylation signal. The two fragments were ligated together and digested with EcoRI to create an 860 base pair fragment with EcoRI ends, which contained a BGH-coding structural sequence joined to the NOS 3' non-translated region. This fragment was introduced into plasmid pMON38, which had been digested with EcoRI and treated with alkaline phosphatase, to create a new plasmid, designated as pMON108, as shown in FIG. 29.

Figure 30:
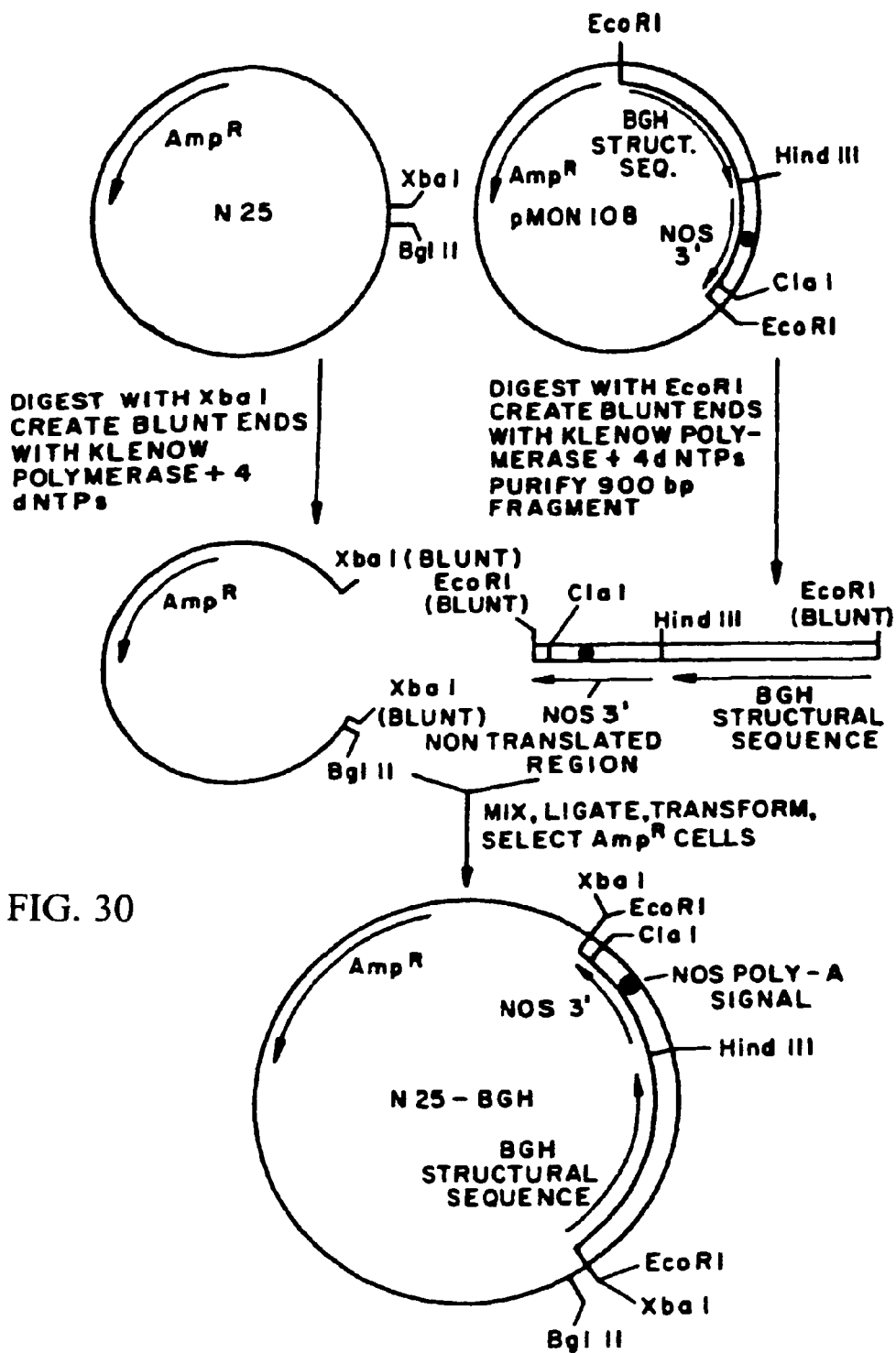
FIG. 30 represents the creation of plasmid N25-BGH, which contains the BGH-NOS sequence surrounded by selected cleavage sites.

A unique BglII restriction site was introduced at the 5' end of the BGH structural sequence by digesting pMON 108 with EcoRI to obtain the 860 bp fragment, and using Klenow polymerase to create blunt ends on the resulting EcoRI fragment. This fragment was ligated into plasmid N25 (a derivative of pBR327 containing a synthetic linker carrying BglII and XbaI cleavage sites inserted at the BamHI site), which had been cleaved with XbaI and treated with Klenow polymerase to obtain blunt ends (N25 contains a unique BglII site located 12 bases from the XbaI site). The resulting plasmid, which contained the 860 bp BGH-NOS fragment in the orientation shown in FIG. 30, was designated as plasmid N25-BGH. This plasmid contains a unique BglII cleavage site located about 25 bases from the 5' end of the BGH structural sequence.

Figure 31:
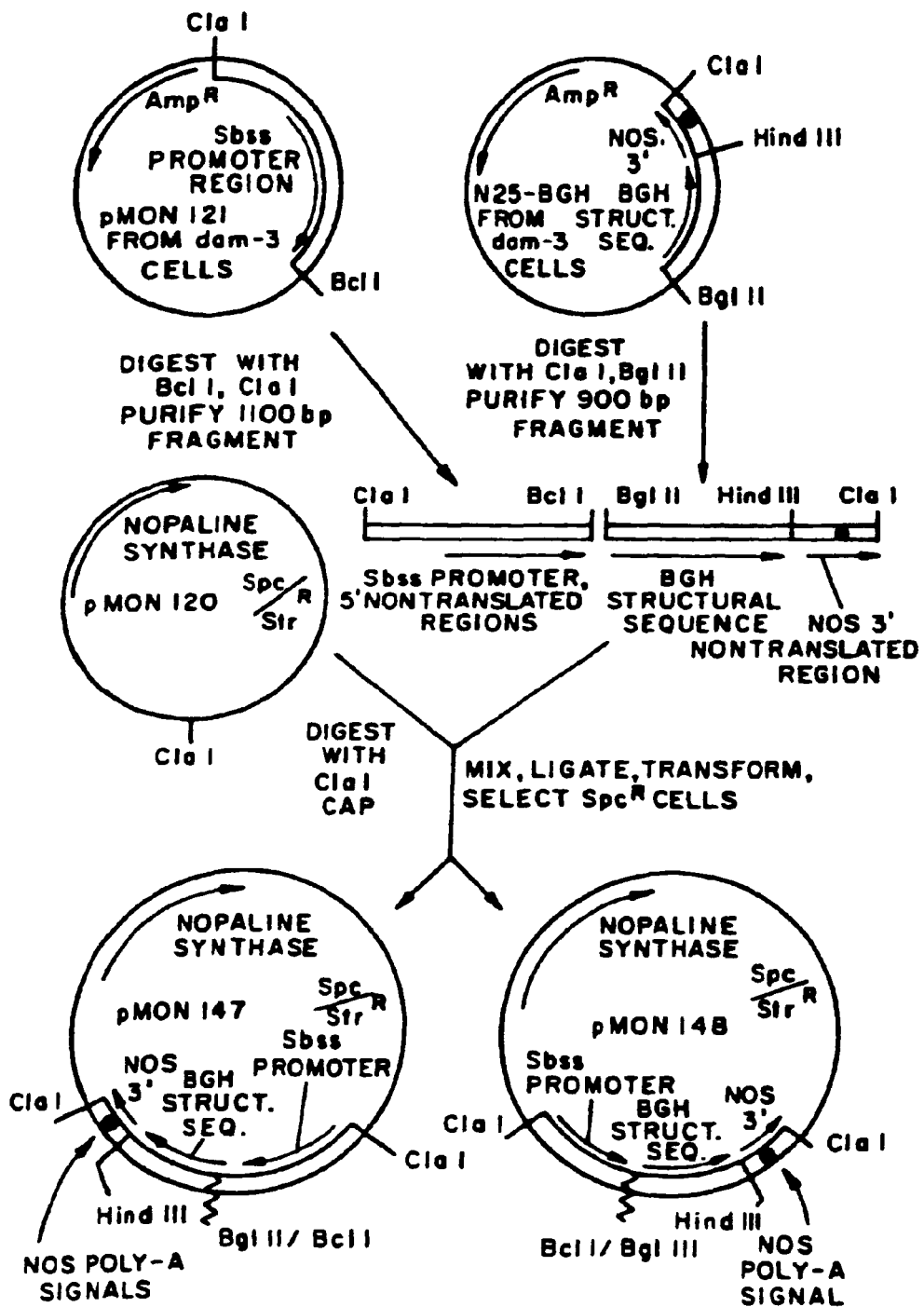
FIG. 31 represents the insertion of a chimeric sbss-BGH-NOS gene into pMON120 to obtain plasmids pMON147 and pMON148.

Plasmid N25-BGH prepared from dam—*E. coli* cells was digested with BglII and ClaI to yield an 860 bp fragment which contained the BGH structural sequence joined to the NOS 3' non-translated region. Separately, plasmid pMON121 (described previously and shown in FIG. 27) was prepared from dam—*E. coli* cells and was digested with ClaI and BclI to create an 1100 bp fragment which contained the sbss promoter region. The fragments were ligated at their compatible BclI/BglII overhangs, and digested with ClaI to yield a ClaI fragment of about 2 kb containing the chimeric sbss-BGH-NOS gene. This fragment was inserted into pMON 120 (described previously and shown in FIG. 8) which had been digested with ClaI. The resulting plasmids, containing the inserted chimeric gene in opposite orientations were designated pMON 147 and pMON 148, as shown in FIG. 31.

Figure 32:
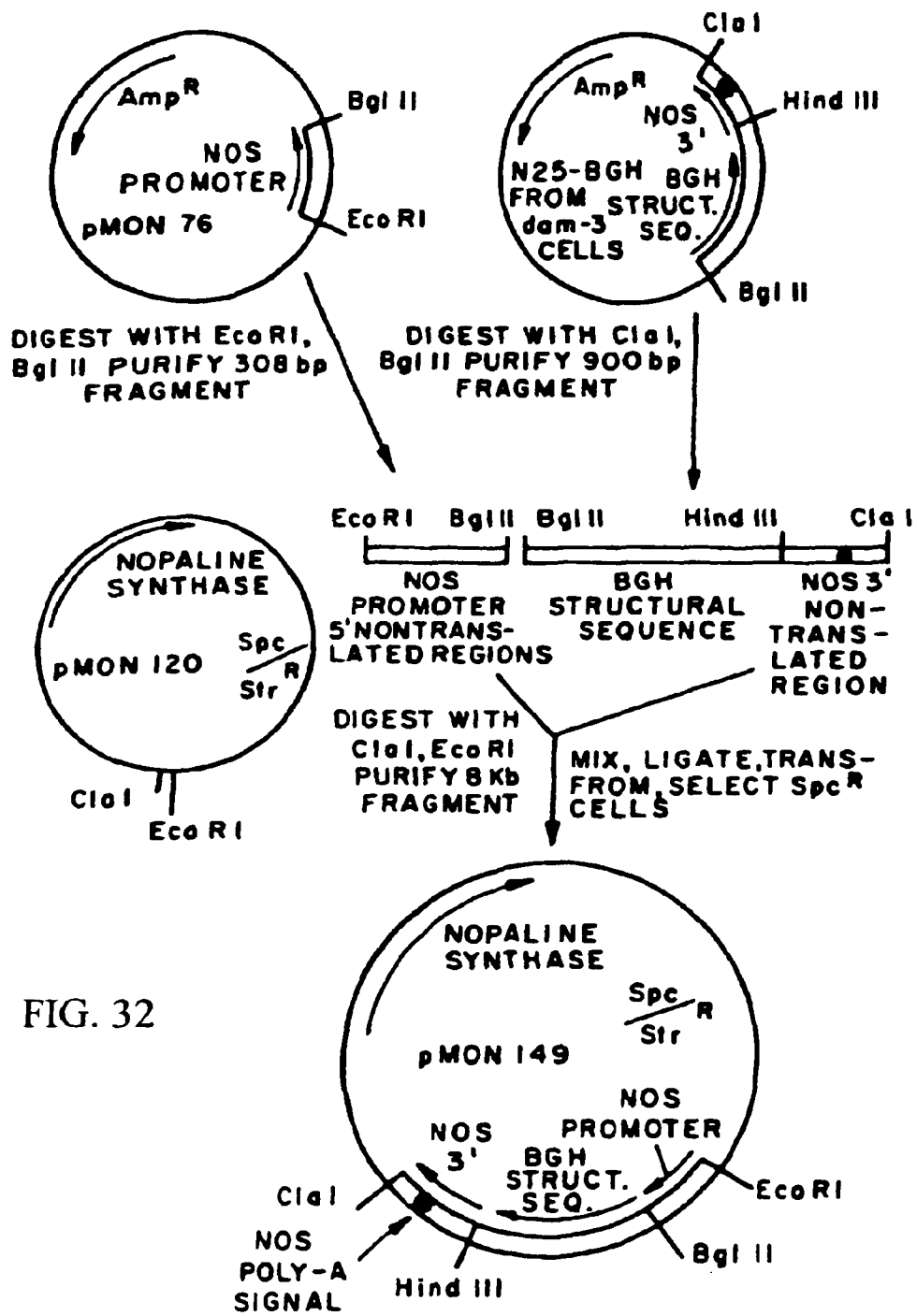
FIG. 32 represents the creation of plasmid pMON149, which contains a chimeric NOS-BGH-NOS gene.

An alternate chimeric BGH gene was created which contained (1) a NOS promoter region and 5' non-translated region, (2) a structural sequence which codes for BGH, and (3) a NOS 3' non-translated region, by the following method, shown in FIG. 32.

Plasmid pMON76 (described above and shown in FIG. 20) was digested with EcoRI and BglII to obtain a 308 bp fragment containing a NOS promoter region and 5' non-translated region. Plasmid N25-BGH prepared from dam—*E. coli* cells (described above and shown in FIG. 30) was digested with BglII and ClaI to obtain a 900 bp fragment containing a BGH structural sequence and a NOS 3' non-translated region. These two fragments were ligated together to obtain a chimeric NOS-BGH-NOS gene in a fragment with EcoRI and ClaI ends. This fragment was ligated with an 8 kb fragment obtained by digesting pMON120 with EcoRI and ClaI. The resulting plasmid, designated as pMON149, is shown in FIG. 32.

Creation of Chimeric NOS-EPSP-NOS Gene

In an alternate preferred embodiment, a chimeric gene was created comprising (1) a NOS promoter region and 5' non-translated region, (2) a structural sequence which codes for the *E. coli* enzyme, 5-enolpyruvylshikimate-3-phosphoric acid synthase (EPSP synthase) and (3) a NOS 3' non-translated region.

EPSP synthase is believed to be the target enzyme for the herbicide, glyphosate, which is marketed by Monsanto Company under the registered trademark, "Roundup." Glyphosate is known to inhibit EPSP synthase activity (Amrhein et al, 1980), and amplification of the EPSP synthase gene in bacteria is known to increase their resistance to glyphosate. Therefore, increasing the level of EPSP synthase activity in plants may confer resistance to glyphosate in transformed plants. Since glyphosate is toxic to most plants, this provides for a useful method of weed control. Seeds of a desired crop plant which has been transformed to increase EPSP synthase activity may be planted in a field. Glyphosate may be applied to the field at concentrations which will kill all non-transformed plants, leaving the non-transformed plants unharmed.

An EPSP synthase gene may be isolated by a variety of means, including the following. A lambda phage library may be created which carries a variety of DNA fragments produced by HindIII cleavage of *E. coli* DNA. See, e.g., Maniatis et al, 1982.

The EPSP synthase gene is one of the genes which are involved in the production of aromatic amino acids. These genes are designated as the "aro" genes; EPSP synthase is designated as aroA. Cells which do not contain functional aro genes are designated as aro-cells. Aro– cells must normally be grown on media supplemented by aromatic amino acids. See Pittard and Wallis, 1966.

Different lambda phages which carry various HindIII fragments may be used to infect mutant *E. coli* cells which do not have EPSP synthase genes. The infected aro– cells may be cultured on media which does not contain the aromatic amino acids, and transformed aro+ clones which are capable of growing on such media may be selected. Such clones are likely to contain the EPSP synthase gene. Phage particles may be isolated from such clones, and DNA may be isolated from these phages. The phage DNA may be cleaved with one or more restriction endonucleases, and by a gradual process of analysis, a fragment which contains the EPSP synthase gene may be isolated.

Figure 33:
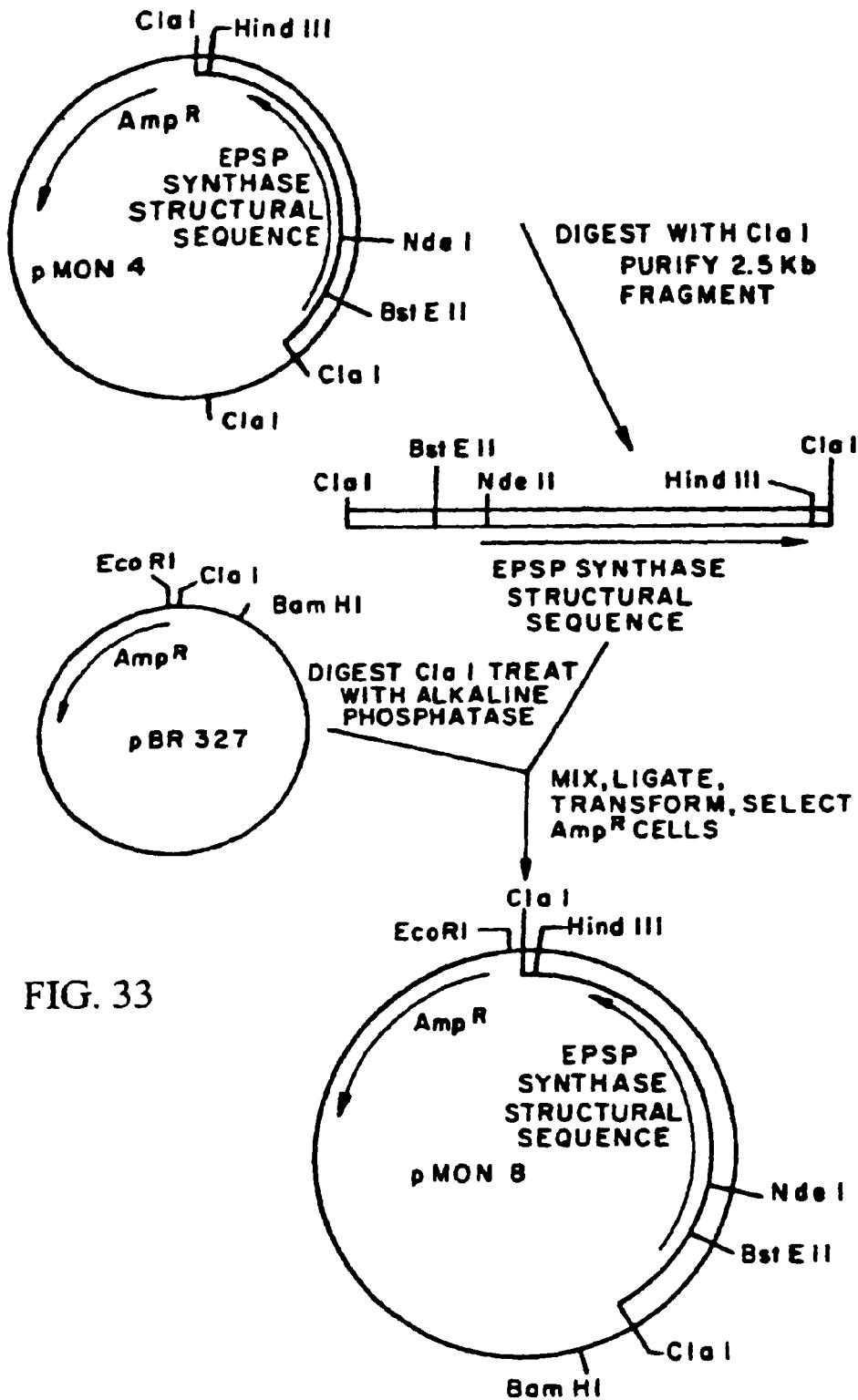
FIG. 33 represents the creation of plasmid pMON8, which contains a structural sequence for EPSP synthase.

Using a procedure similar to the method summarized above, the Applicants isolated an 11 kb HindIII fragment which contained the entire *E. coli* EPSP synthase gene. This fragment was digested with BglII to produce a 3.5 kb HindIII-BglII fragment which contained the entire EPSP synthase gene. This 3.5 kb fragment was inserted into plasmid pKC7 (Rao and Rogers, 1979) to produce plasmid pMON4, which is shown in FIG. 33.

Plasmid pMON4 was digested with ClaI to yield a 2.5 kb fragment which contained the EPSP synthase structural sequence. This fragment was inserted into pBR327 that had been digested with ClaI, to create pMON8, as shown in FIG. 33.

pMON8 was digested with BamHI and NdeI to obtain a 4.9 kb fragment. This fragment lacked about 200 nucleotides encoding the amino terminus of the EPSP synthase structural sequence.

Figure 34:
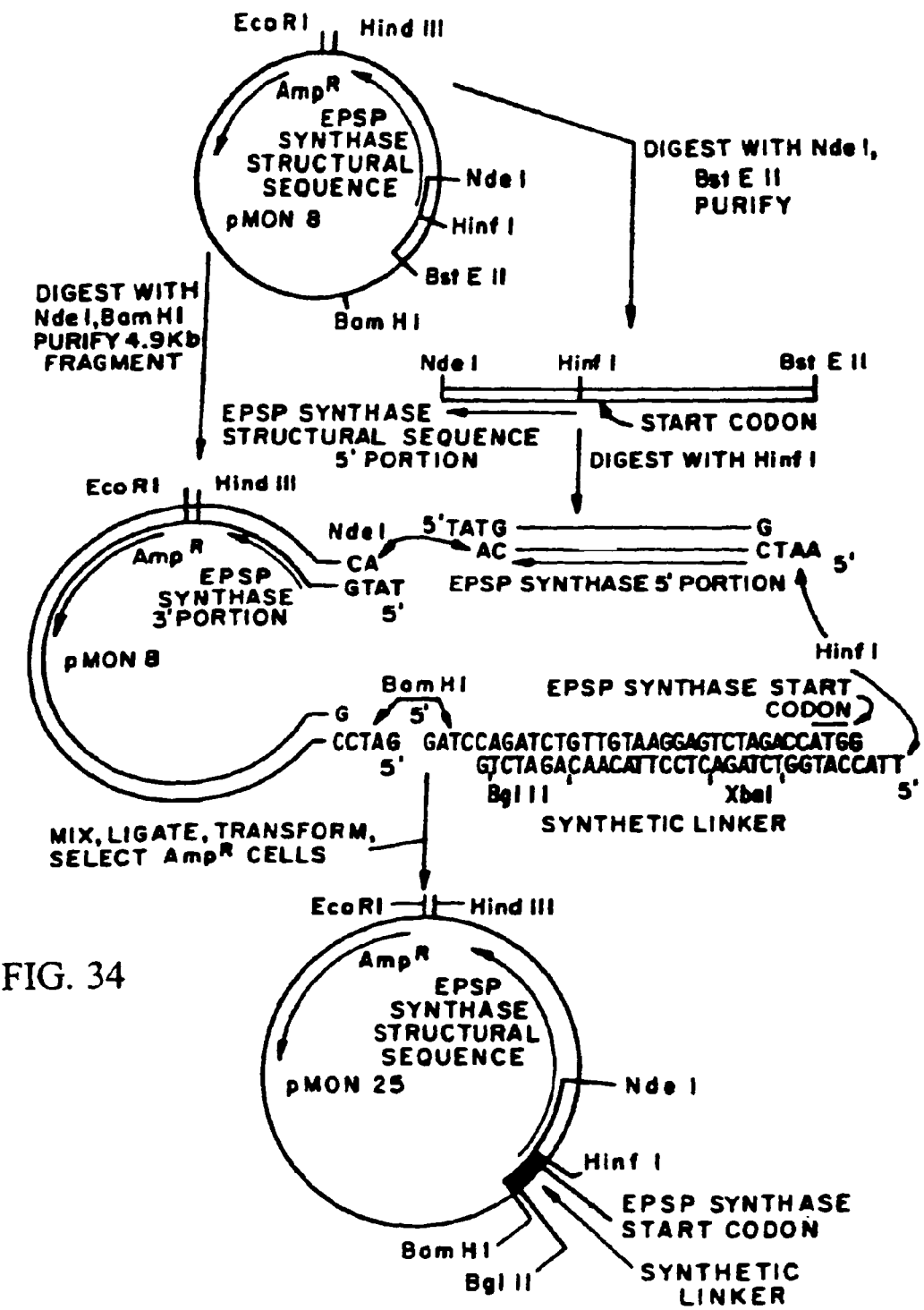
FIG. 34 represents the creation of plasmid pMON25, which contains an EPSP synthase structural sequence with several cleavage site near the start codon.

The missing nucleotides were replaced by ligating a HinfI/NdeI fragment, obtained from pMON8 as shown in FIG. 34, together with a synthetic oligonucleotide sequence containing (1) the EPSP synthase start codon and the first three nucleotides, (2) a unique BglII site, and (3) the appropriate BamHI and HinfI ends. The resulting plasmid, pMON25, contains an intact EPSP synthase structural sequence with unique BamHI and BglII sites positioned near the start codon.

Figure 35:
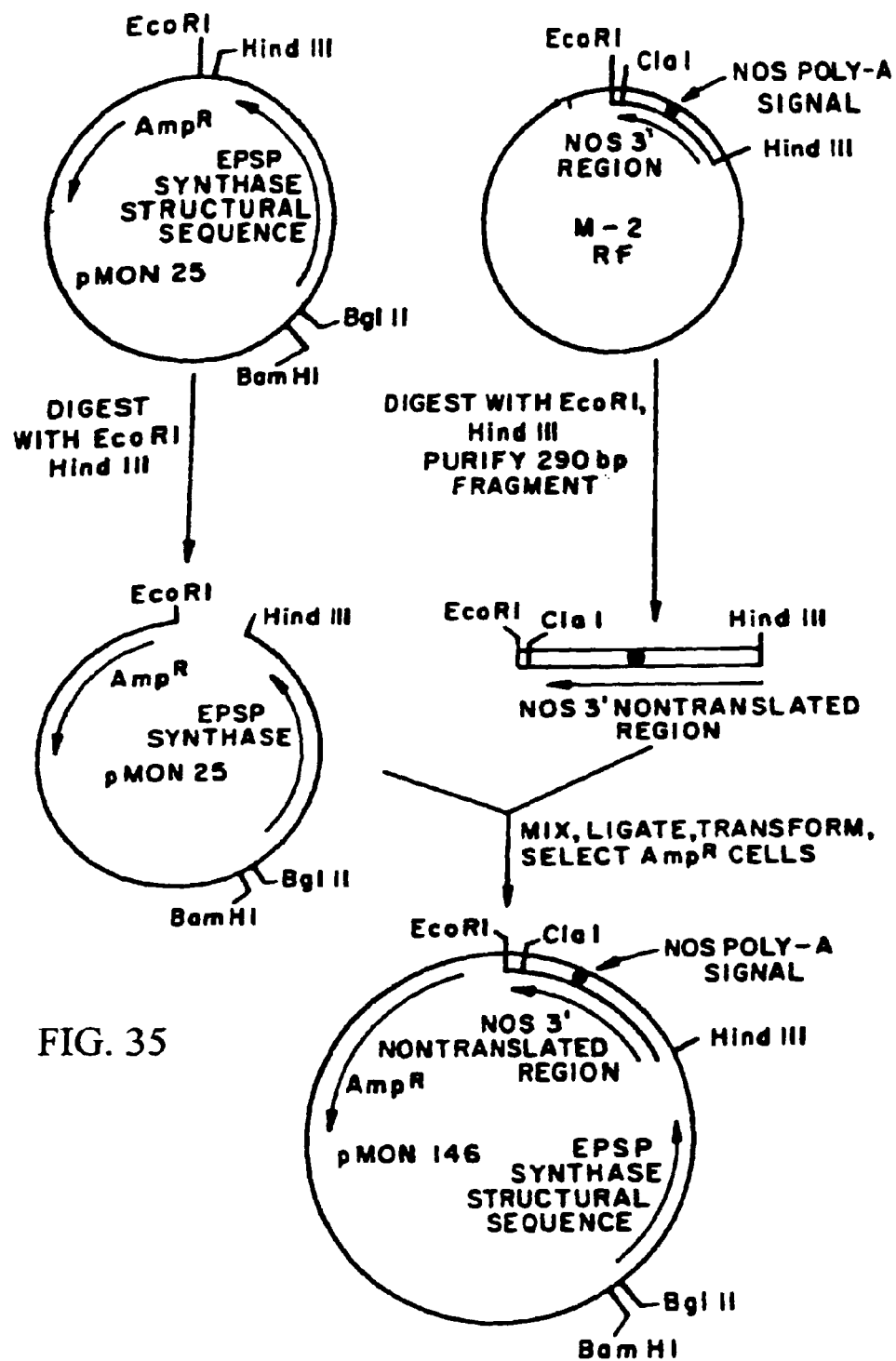
FIG. 35 represents the creation of plasmid pMON146, which contains a chimeric sequence comprising EPSP synthase and a NOS 3' region.
Figure 36:
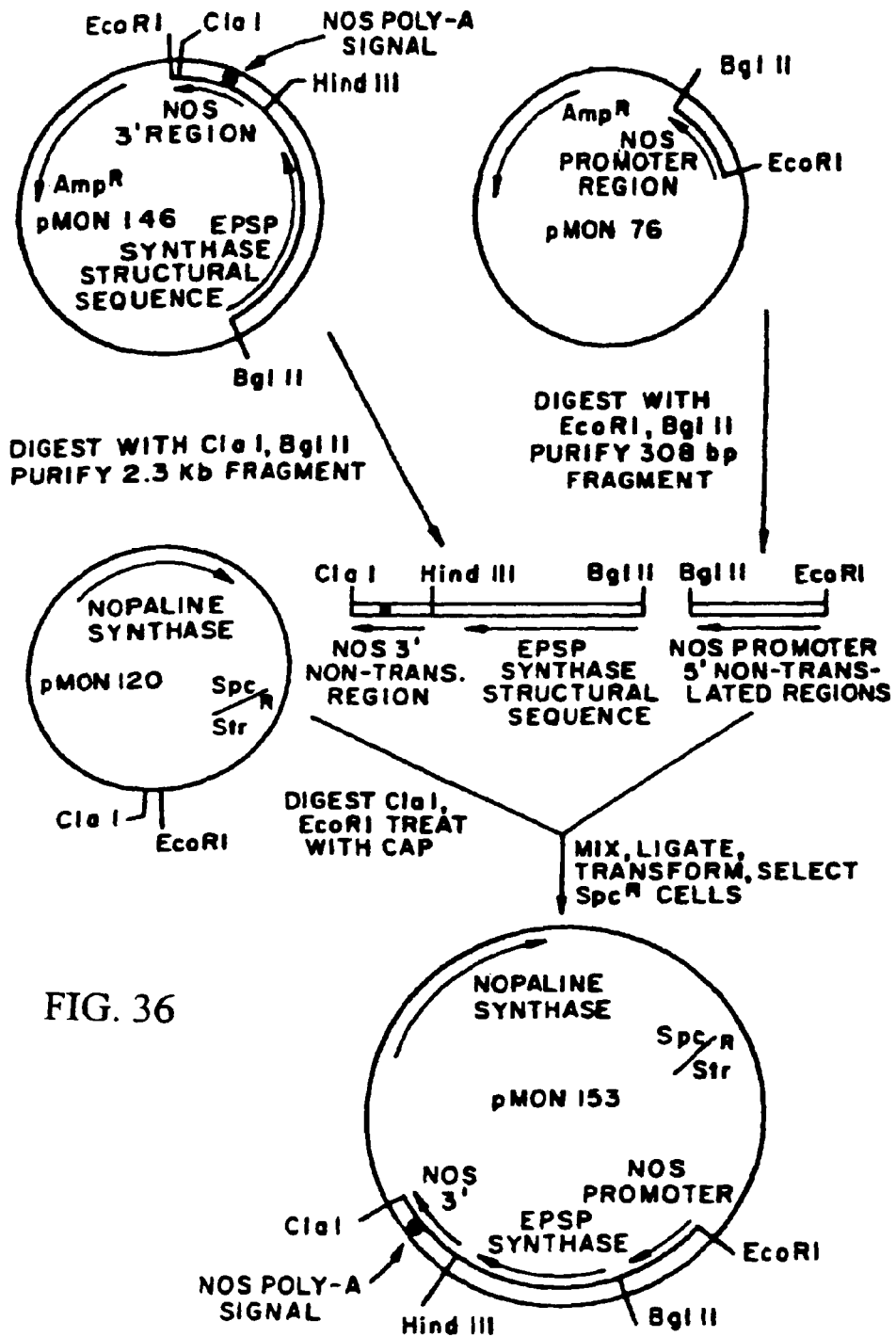
FIG. 36 represents the insertion of a chimeric NOS-EPSP-NOS gene into pMON120 to obtain plasmid pMON153.

Double stranded M-2 DNA (described previously and shown in FIG. 19) was digested with HindIII and EcoRI to yield a 290 bp fragment which contains the NOS 3' non-translated region and poly-adenylation signal. This fragment was introduced into a pMON25 plasmid that had been digested with EcoRI and HindIII to create a plasmid, designated as pMON146 (shown in FIG. 35) which contains the EPSP structural sequence joined to the NOS 3' non-translated region.

pMON146 was cleaved with ClaI and BglII to yield a 2.3 kb fragment carrying the EPSP structural sequence joined to the NOS 3' non-translated region. pMON76 (described previously and shown in FIG. 20) was digested with BglII and EcoRI to create a 310 bp fragment containing the NOS promoter region and 5' non-translated region. The above fragments were mixed with pMON 120 (described previously and shown in FIG. 8) that had been digested with ClaI and EcoRI, and the mixture was ligated. The resulting plasmid, designated pMON153, is shown in FIG. 36. This plasmid contains the chimeric NOS-EPSP-NOS gene.

Figure 37:
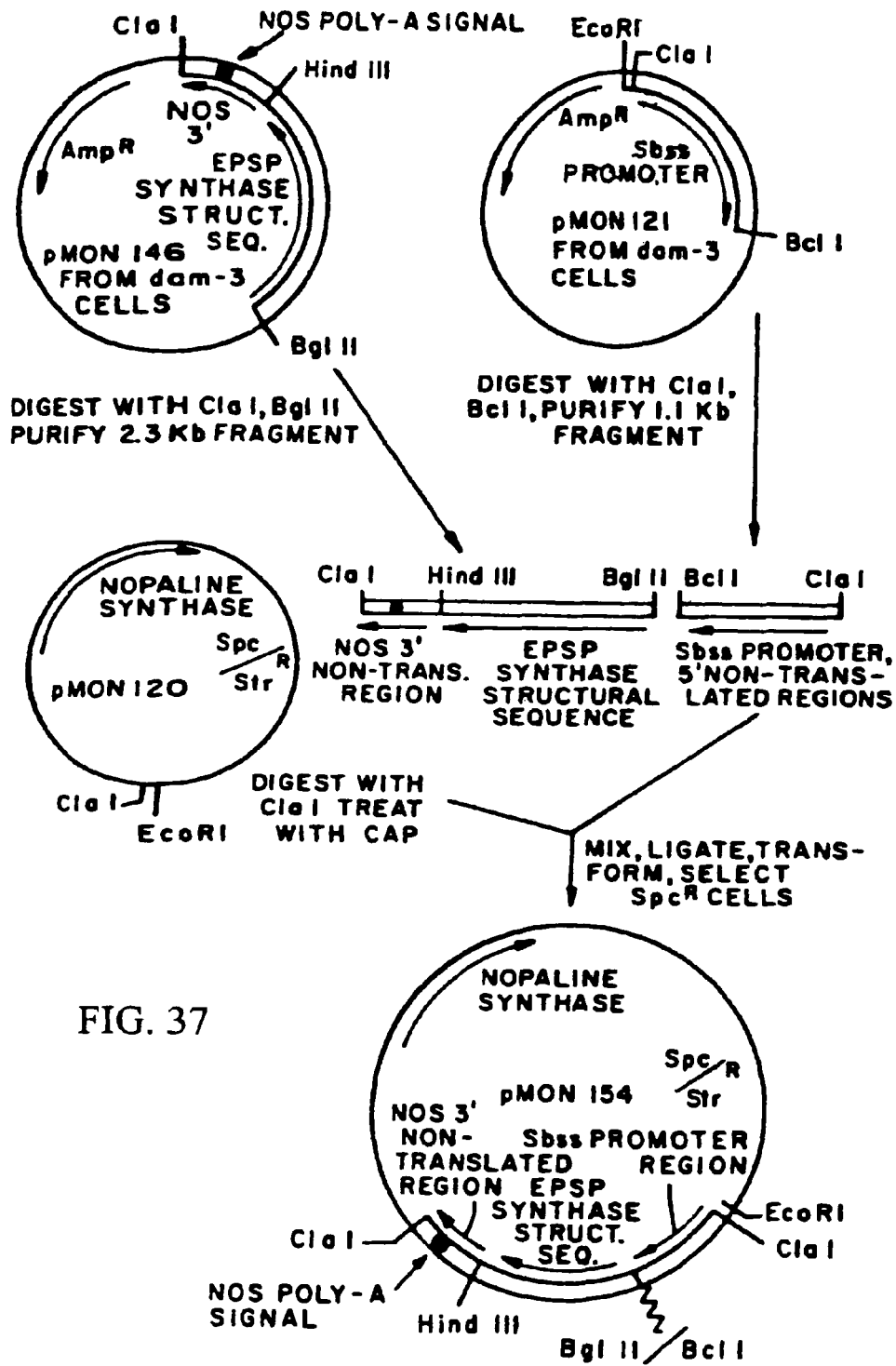
FIG. 37 represents the creation of plasmid pMON154, which contains a chimeric sbss-EPSP-NOS gene.

A plasmid containing a chimeric sbss-EPSP-NOS gene wa prepared in the following manner, shown in FIG. 37. Plasmid pMON146 (described previously and shown in FIG. 35) was digested with ClaI and BglII, and a 2.3 kb fragment was purified. This fragment contained the EPSP synthase structural sequence coupled to a NOS 3' non-translated region with a poly-adenylation signal. Plasmid pMON121 (described above and shown in FIG. 27) was digested with ClaI and BclI and a 1.1 kb fragment was purified. This fragment contains an sbss promoter region and 5' non-translated region. The two fragments were mixed and ligated with T4 DNA ligase and subsequently digested with ClaI. This created a chimeric sbss-EPSP-NOS gene, joined through compatible BglII and BclI termini. This chimeric gene with ClaI termini was inserted into plasmid pMON120 which had been digested with ClaI and treated with calf alkaline phosphatase (CAP). The mixture was ligated with T4 DNA ligase. The resulting mixture of fragments and plasmids was used to transform *E. coli* cells, which were selected for resistance to spectinomycin. A colony of resistant cells was isolated, and the plasmid in this colony was designated as pMON154, as shown in FIG. 37.

A culture of *E. coli* containing pMON154 has been deposited with the American Type Culture Center. This culture has been assigned accession number 39265.

Plasmid pMON128 (or any other plasmid derived by inserting a desired gene into pMON120) is inserted into a microorganism which contains an octopine-type Ti plasmid (or other suitable plasmid). Suitable microorganisms include *A. tumefaciens* and *A. rhizogenes* which carry Ti or Ri plasmids. Other microorganisms which might also be useful for use in this invention include other species of *Agrobacterium*, as well as bacteria in the genus *Rhizobia*. The suitability of these cells, or of any other cells known at present or hereafter discovered or created, for use in this invention may be determined through routine experimentation by those skilled in the art.

The plasmid may be inserted into the microorganism by any desired method, such as transformation (i.e., contacting plasmids with cells that have been treated to increase their uptake of DNA) or conjugation with cells that contain the pMON128 or other plasmids.

The inserted plasmid (such as pMON128) has a region which is homologous to a sequence within the Ti plasmid. This "LIH" region of homology allows a single crossover event whereby pMON128 and an octopine-type Ti plasmid combine with each other to form a co-integrate plasmid. See, e.g., Stryer, supra, at p. 752-754. Normally, this will occur within the *A. tumefaciens* cell after pMON128 has been inserted into the cell. Alternately, the co-integrate plasmid may be created in a different type of cell or in vitro, and then inserted into an *A. tumefaciens* or other type of cell which can transfer the co-integrate plasmid into plant cells.

Figure 9:
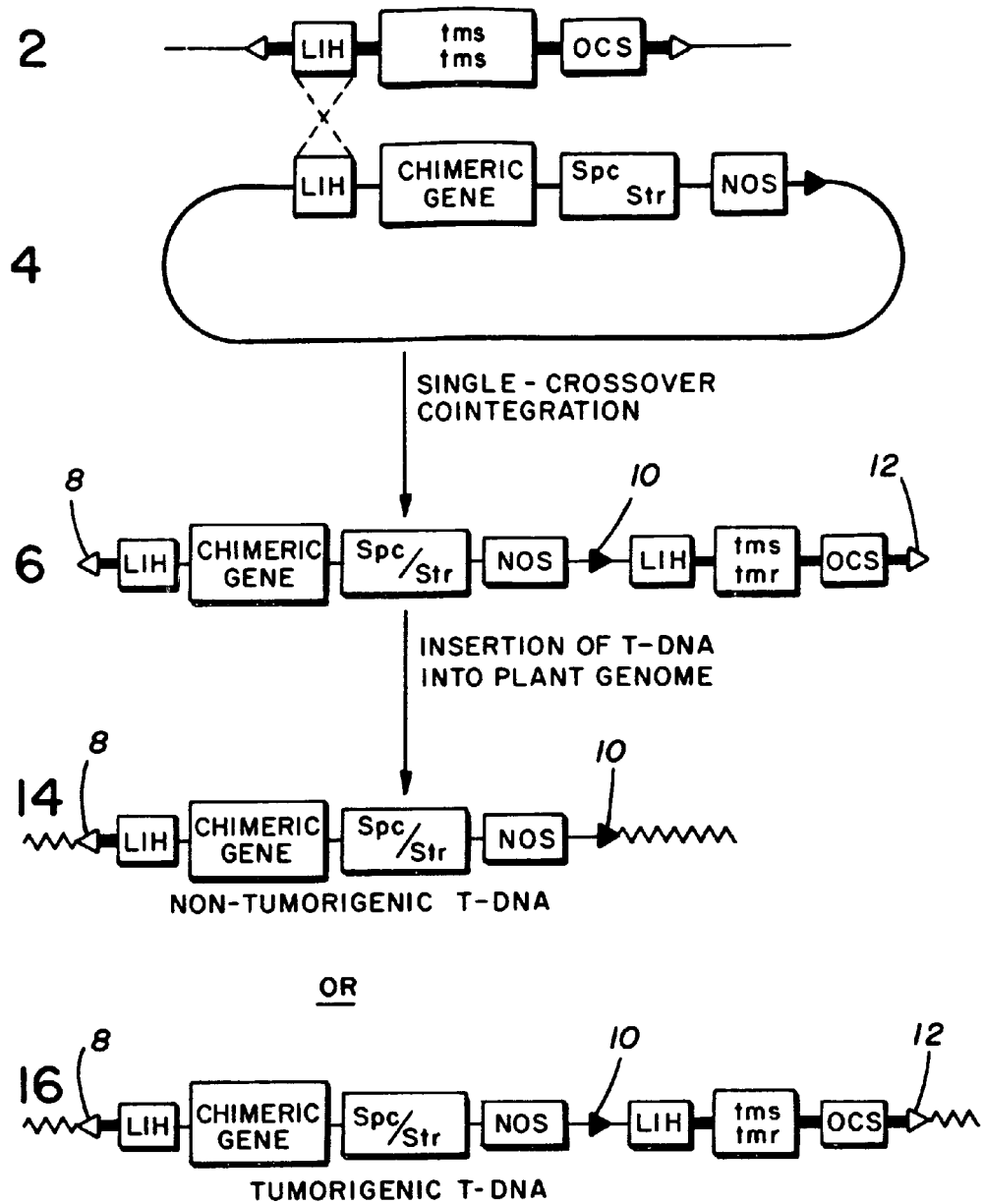
FIG. 9 represents the cointegration of pMON128 with a wild-type Ti plasmid by means of a single crossover event, thereby creating a co-integrate plasmid with multiple borders.
Figure 10:
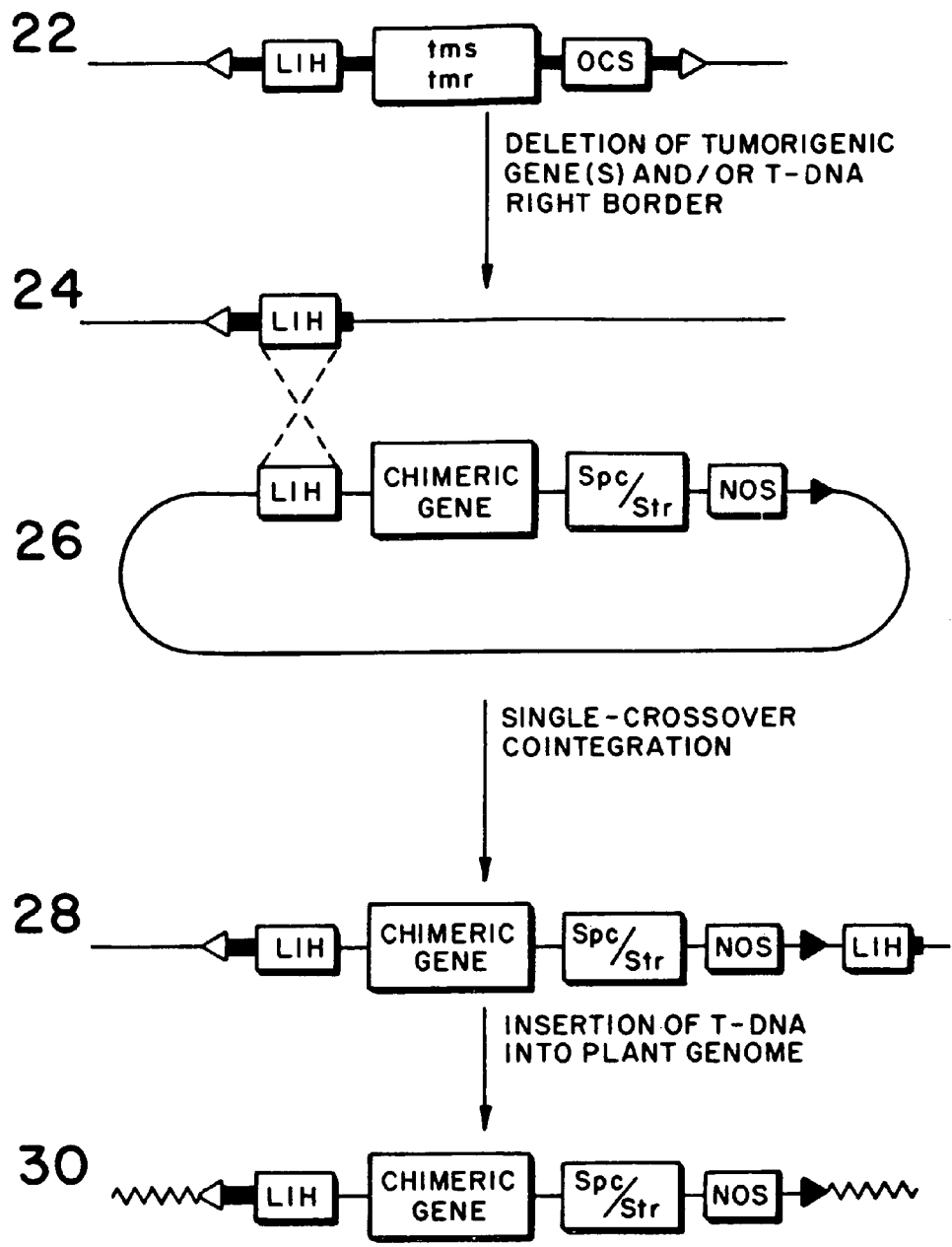
FIG. 10 indicates the co-integration of pMON128 with a disarmed Ti-plasmid, thereby creating a non-tumorigenic cointegrate plasmid.

The inserted plasmid, such as pMON128, combines with the Ti plasmid in the manner represented by FIG. 9 or 10, depending upon what type of Ti plasmid is involved.

In FIG. 9, item 2 represents the T-DNA portion of an octopine-type Ti plasmid. Item 4 represents the inserted plasmid, such as pMON128. When these two plasmids co-exist in the same cell, a crossover event can occur which results in the creation of co-integrate plasmid 6.

Co-integrate plasmid 6 has one left border 8, and two right borders 10 and 12. The two right borders are designated herein as the "proximal" right border 10 (the right border closest to left border 8), and the "distal" right border 12 (the right border that is more distant from left border 8. Proximate right border 10 was carried by plasmid 4; the distal right border was contained on Ti plasmid 2 before co-integration.

A culture of *A. tumefaciens* GV3111 containing a co-integrate plasmid formed by pMON1-28 and wild-type Ti plasmid pTiB653 has been deposited with the American Type Culture Center. This culture has been assigned accession number 39266.

When co-integrate Ti plasmid 6, shown in FIG. 9, is inserted into a plant cell, either of two regions of DNA may enter the plant genome, T-DNA region 14 or T-DNA region 16.

T-DNA region 14 is bounded by left border 8 and proximate right border 10. Region 14 contains the chimeric gene and any other genes contained in plasmid 4, such as the spc/str selectable marker and the NOS scorable marker. However, region 14 does not contain any of the T-DNA genes which would cause crown gall disease or otherwise disrupt the metabolism or regenerative capacity of the plant cell.

T-DNA region 16 contains left border 8 and both right borders 10 and 12. This segment of T-DNA contains the chimeric gene and any other genes contained in plasmid 4. However, T-DNA region 16 also contains the T-DNA genes which are believed to cause crown gall disease.

Either of the foregoing T-DNA segments, Region 14 or Region 16, might be transferred to the plant DNA. This is presumed to occur at a 50-50 probability for any given T-DNA transfer. This is likely to lead to a mixture of transformed cells, some of which are tumorous and some or which are non-tumorous. It is possible to isolate and cultivate non-tumorous cells from the mixture, as described in the examples.

An alternate approach has also been developed which avoids the need for isolating tumorous from non-tumorous cells. Several mutant strains of *A. tumefaciens* have been isolated which are incapable of causing crown gall disease. Such strains are usually referred to as "disarmed" Ti plasmids. A Ti or Ri plasmid may be disarmed by one or more of the following types of mutations:

1. Removal or inactivation of one of the border regions. One such disarmed octopine plasmid, which has a left border but not a right border, is designated as pAL4421; this plasmid is contained in *A. tumefaciens* strain LBA4421 (Ooms et al, 1982; Garfinkel et al, 1981).

2. Removal or inactivation of the one or more of the "tumor morphology" genes, designated as the tmr and tms genes. See, e.g., Leemans et al, 1982.

Various other types of disarmed plant tumor inducing plasmids may be prepared using methods known to those skilled in the art. See Matzke and Chilton, 1981; Leemans et al, 1981; Koekman et al, 1979.

FIG. 10 represents an octopine-type Ti plasmid with a T-DNA region 22 which undergoes mutation to delete the tms and tmr genes and the right border. This results in a disarmed Ti plasmid with partial T-DNA region 24. When plasmid 26 (such as pMON128) is inserted into a cell that carries the disarmed Ti plasmid 24, a crossover event occurs which creates a co-integrate Ti plasmid with disarmed T-DNA region 28. The LIH region of homology is repeated in this Ti plasmid, but the disarmed Ti plasmid does not contain any oncogenic genes. Alternately, if only the right border had been deleted from T-DNA region 22, then the tms and tmr genes and the octopine synthase (OCS) gene would be contained in the co-integrate disarmed Ti plasmid; however, they would have been located outside of the T-DNA borders.

The disarmed co-integrate Ti plasmid is used to infect plant cells, and T-DNA region 28 enters the plant genome, as shown by transformed DNA 30. Plant cells transformed by disarmed T-DNA 28 have normal phytohormone metabolism, and normal capability to be regenerated into differentiated plants.

After pMON128 is inserted into *A. tumefaciens* cells, the desired crossover event will occur in a certain fraction of the cells. Cells which contain co-integrate plasmids (whether virulent or disarmed) may be easily selected from other cells in which the crossover did not occur, in the following manner. Plasmid pMON120 and its derivatives contain a marker gene (spc/str), which is expressed in *A. tumefaciens*. However, these plasmids do not replicate in *A. tumefaciens*. Therefore, the spc/str marker gene will not be replicated or stably inherited by *A. tumefaciens* unless the inserted plasmid combines with another plasmid that can replicate in *A. tumefaciens*. The most probable such combination, due to the region of homology, is the co-integrate formed with the Ti plasmid. *A. tumefaciens* cells which contain this co-integrate plasmid can readily be identified and selected by growth of the cells on medium containing either spc or str, or both.

The Ti plasmid 28, shown in FIG. 10, contains two LIH regions. It is possible that co-integrate Ti plasmids will undergo a subsequent crossover event, wherein the two LIH regions will recombine. This event is undesirable, since it can lead to a deletion of the DNA between the LIH regions, including the chimeric gene. However, this is not likely to lead to serious difficulties, for two reasons. First, this event is likely to occur at a relatively low probability, such as about $10^{-2}$. Second, plasmid pMON120 and its derivatives, have been designed so that the selectable marker gene (spc/str) is located in the region of DNA that would be deleted by the crossover event. Therefore, the selective conditions that are used to identify and culture *Agrobacteria* cells containing co-integrate plasmids will also serve to kill the descendants of cells that undergo a subsequent crossover event which eliminates the chimeric gene from the Ti plasmid.

Only one of the LIH regions in the co-integrate Ti plasmid will be inserted into the plant genome, as shown in FIG. 10. This important feature results from the design of pMON120, and it distinguishes this co-integrate plasmid from undesired co-integrate plasmids formed by the prior art. The LIH region which lies outside of the T-DNA borders will not be inserted into the plant genome. This leads to at least two important advantages. First, the presence of two LIH regions inserted into the plant genome could result in crossover events which would lead to loss of the inserted genes in the transformed plant cells and their progeny. Second, the presence of two regions of DNA homology can significantly complicate efforts to analyze the DNA inserted into the plant genome (Matzke and Chilton, 1981).

After *A. tumefaciens* cells which contain the co-integrate Ti plasmids with the chimeric genes have been identified and isolated, the co-integrate plasmids (or portions thereof) must be inserted into the plant cells. Eventually, methods may be developed to perform this step directly. In the meantime, a method has been developed which may be used conveniently and with good results. This method is described in two separate, simultaneously-filed applications, entitled "Transformation of Plant Cells by Extended Bacterial Co-Cultivation" Ser. No. 458,413 and "Rapid Culture of Plant Protoplasts," Ser. No. 538,412 The contents of both of those applications are hereby incorporated by reference. The method described in those applications may be briefly summarized as follows.

The plant cells to be transformed are contacted with enzymes which remove the cell walls. This converts the plant cells into protoplasts, which are viable cells surrounded by membranes. The enzymes are removed, and the protoplasts begin to regenerate cell wall material. At an appropriate time, the *A. tumefaciens* cells (which contain the co-integrate Ti plasmids with chimeric genes) are mixed with the plant protoplasts. The cells are co-cultivated for a period of time which allows the *A. tumefaciens* to infect the plant cells. After an appropriate co-cultivation period, the *A. tumefaciens* cells are killed, and the plant cells are propagated.

Plant cells which have been transformed (i.e., cells which have received DNA from the co-integrate Ti plasmids) and their descendants may be selected by a variety of methods, depending upon the type of gene(s) that were inserted into the plant genome. For example, certain genes may cause various antibiotics to be inactivated; such genes include the chimeric NOS-NPT II-NOS gene carried by pMON128. Such genes may serve as selectable markers; a group of, cells may be cultured on medium containing the antibiotic which is inactivated by the chimeric gene product, and only those cells containing the selectable marker gene will survive.

A variety of genes may serve as scorable markers in plant cells. For example, pMON120 and its derivative plasmids, such as pMON128, carry a nopaline synthase (NOS) gene which is expressed in plant cells. This gene codes for an enzyme which catalyzes the formation of nopaline. Nopaline is a non-detrimental compound which usually is accumulated at low quantities in most types of plants; it can be easily detected by electrophoretic or chromatographic methods.

If a plant is transformed by a gene which creates a polypeptide that is difficult to detect, then the presence of a selectable marker gene (such as the NOS-NPT II-NOS chimeric gene) or a scorable marker gene (such as the NOS gene) in the transforming vector may assist in the identification and isolation of transformed cells.

Virtually any desired gene may be inserted into pMON120 or other which are designed to form co-integrates with plant tumor inducing or similar plasmids. For example, the Applicants have created a variety of chimeric genes, which are discussed in the previously-cited application, "Chimeric Genes Suitable for Expression in Plant Cells."

The suitability of any gene for use in this invention may be determined through routine experimentation by those skilled in the art. Such usage is not limited to chimeric genes; for example, this invention may be used to insert multiple copies of a natural gene into plant cells.

This invention is suitable for use with a wide variety of plants, as may be determined through routine experimentation by those skilled in the art. For example, this invention is likely to be useful to transform cells from any type of plant which can be infected by bacteria from the genus *Agrobacterium*. It is believed that virtually all dicotyledonous plants, and certain monocots, can be infected by one or more strains of *Agrobacterium*. In addition, microorganisms of the genus *Rhizobia* are likely to be useful for carrying co-integrate plasmids of this invention, as may be determined by those skilled in the art. Such bacteria might be preferred for certain types of transformations or plant types.

Certain types of plant cells can be cultured in vitro and regenerated into differentiated plants using techniques known to those skilled in the art. Such plant types include potatoes, tomatoes, carrots, alfalfa and sunflowers. Research in in vitro plant culture techniques is progressing rapidly, and methods are likely to be developed to permit the regeneration of a much wider range of plants from cells cultured in vitro. Cells from any such plant with regenerative capacity are likely to be transformable by the in vitro co-cultivation method discussed previously, as may be determined through routine experimentation by those skilled in the art. Such transformed plant cells may be regenerated into differentiated plants using the procedures described in the examples.

The in vitro co-cultivation method offers certain advantages in the transformation of plants which are susceptible to in vitro culturing and regeneration. However, this invention is not limited to in vitro cell culture methods. For example, a variety of plant shoots and cuttings (including soybeans, carrots, and sunflowers) have been transformed by contact with *A. tumefaciens* cells carrying the co-integrate plasmids of this invention. It is also possible to regenerate virtually any type of plant from a cutting or shoot. Therefore, it may be possible to develop methods of transforming shoots or cuttings using virulent or preferably disarmed co-integrate plasmids of this invention or mixtures thereof, and subsequently regenerating the transformed shoots or cuttings into differentiated plants which pass the inserted genes to their progeny.

As mentioned previously, it is not essential to this invention that co-cultivation be utilized to transfer the co-integrate plasmids of this invention into plant cells. A variety of other methods are being used to insert DNA into cells. Such methods include encapsulation of DNA in liposomes, complexing the DNA with chemicals such as polycationic substances or calcium phosphate, fusion of bacterial spheroplasts with plant protoplasts, microinjection of DNA into a cell, and induction of DNA uptake by means of electric current. Although such methods have not been used to insert DNA into plant cells with satisfactory efficiency to date, they are being actively researched and they may be useful for inserting foreign genes into plant cells, using the intermediate vectors and co-integrate plasmids of this invention, or plasmids derived therefrom.

This invention may be useful for a wide variety of purposes. For example, certain bacterial enzymes, such as 5-enol pyruvyl shikimate-3-phosphoric acid synthase (EPSP synthase) are inactivated by certain herbicides; other enzymes, such as glutathione-S-transferase (GST), inactivate certain herbicides. It may be possible to insert chimeric genes into plants which will cause expression of such enzymes in the plants, thereby causing the plants to become resistant to one or more herbicides. This would allow for the herbicide, which would normally kill the untransformed plant, to be applied to a field of transformed plants. The herbicide would serve as a weed-killer, leaving the transformed plants undamaged.

Alternately, it may be possible to insert chimeric genes into plants which will cause the plants to create mammalian polypeptides, such as insulin, interferon, growth hormone, etc. At an appropriate time, the plants (or cultured plant tissue) would be harvested. Using a variety of processes which are known to those skilled in the art, the desired protein may be extracted from the harvested plant tissue.

An alternate use of this invention is to create plants with high content of desired substances, such as storage proteins or other proteins. For example, a plant might contain one or more copies of a gene which codes for a desirable protein. Additional copies of this gene may be inserted into the plant by means of this invention. Alternately, the structural sequence of the gene might be inserted into a chimeric gene under the control of a different promoter which causes prolific transcription of the structural sequence.

The methods of this invention may be used to identify, isolate, and study DNA sequences to determine whether they are capable of promoting or otherwise regulating the expression of genes within plant cells. For example, the DNA from any type of cell can be fragmented, using partial endonuclease digestion or other methods. The DNA fragments can be inserted randomly into plasmids similar to pMON128. These plasmids, instead of having a full chimeric gene such as NOS-NPT II-NOS, will have a partial chimeric gene, with a cleavage site for the insertion of DNA fragments, rather than a NOS promoter or other promoter. The plasmids with inserted DNA are then inserted into *A. tumefaciens*, where they can recombine with the Ti plasmids. Cells having co-integrate plasmids are selected by means of the spc/str or other marker gene. The co-integrate plasmids are then inserted into the plant cells, by bacterial co-cultivation or other means. The plant cells will contain a selectable marker structural sequence such as the NPT II structural sequence, but this structural sequence will not be transcribed unless the inserted DNA fragment serves as a promoter for the structural sequence. The plant cells may be selected by growing them on medium containing kanamycin or other appropriate antibiotics.

Using this method, it is possible to evaluate the promoter regions of bacteria, yeast, fungus, algae, other microorganisms, and animal cells to determine whether they function as gene promoters in various types of plant cells. It is also possible to evaluate promoters from one type of plant in other types of plant cells. By using similar methods and varying the cleavage site in the starting plasmid, it is possible to evaluate the performance of any DNA sequence as a 5' non-translated region, a 3' non-translated region, or any other type of regulatory sequence.

As used herein, "a piece of DNA" includes plasmids, phages, DNA fragments, and polynucleotides, whether natural or synthetic.

As used herein, a "chimeric piece of DNA" is limited to a piece of DNA which contains at least two portions (i.e., two nucleotide sequences) that were derived from different and distinct pieces of DNA. For example, a chimeric piece of DNA cannot be created by merely deleting one or more portions of a naturally existing plasmid. A chimeric piece of DNA may be produced by a variety of methods, such as ligating two fragments from different plasmids together, or by synthesizing a polynucleotide wherein the sequence of bases was determined by analysis of the base sequences of two different plasmids.

As used herein, a chimeric piece of DNA is limited to DNA which has been assembled, synthesized, or otherwise produced as a result of man-made efforts, and any piece of DNA which is replicated or otherwise derived therefrom. "Man-made efforts" include enzymatic, cellular, and other biological processes, if such processes occur under conditions which are caused, enhanced, or controlled by human effort or intervention; this excludes plasmids, phages, and polynucleotides which are created solely by natural processes. As used herein, the term "derived from" shall be construed broadly. Whenever used in a claim, the term "chimeric" shall be a material limitation.

As used herein, a "marker gene" is a gene which confers a phenotypically identifiable trait upon the host cell which allows transformed host cells to be distinguished from non-transformed cells. This includes screenable, scorable, and selectable markers.

As used herein, a "region of homology" refers to a sequence of bases in one plasmid which has sufficient correlation with a sequence of bases in a different plasmid to cause recombination of the plasmid to occur at a statistically determinable frequency. Preferably, such recombination should occur at a frequency which allows for the convenient selection of cells having combined plasmids, e.g., greater than 1 per $10^6$ cells. This term is described more fully in a variety of publications, e.g., Leemans et al, 1981.

The term "chimeric gene" refers to a gene that contains at least two portions that were derived from different and distinct genes. As used herein, this term is limited to genes which have been assembled, synthesized, or otherwise produced as a result of man-made efforts, and any genes which are replicated or otherwise derived therefrom. "Man-made efforts" include enzymatic, cellular, and other biological processes, if such processes occur under conditions which are caused, enhanced, or controlled by human effort or intervention; this excludes genes which are created solely by natural processes.

As used herein, a "gene" is limited to a segment of DNA which is normally regarded as a gene by those skilled in the art. For example, a plasmid might contain a plant-derived promoter region and a heterologous structural sequence, but unless those two segments are positioned with respect to each other in the plasmid such that the promoter region causes the transcription of the structural sequence, then those two segments would not be regarded as included in the same gene.

This invention relates to chimeric genes which have structural sequences that are "heterologous" with respect to their promoter regions. This includes at least two types of chimeric genes:

1. DNA of a gene which is foreign to a plant cell. For example, if a structural sequence which codes for mammalian protein or bacterial protein is coupled to a plant promoter region, such a gene would be regarded as heterologous.

2. A plant cell gene which is naturally promoted by a different plant promoter region. For example, if a structural sequence which codes for a plant protein is normally controlled by a low-quantity promoter, the structural sequence may be coupled with a prolific promoter. This might cause a higher quantity of transcription of the structural sequence, thereby leading to plants with higher protein content. Such a structural sequence would be regarded as heterologous with regard to the prolific promoter.

However, it is not essential for this invention that the entire structural sequence be heterologous with respect to the entire promoter region. For example, a chimeric gene of this invention may be created which would be translated into a "fusion protein", i.e., a protein comprising polypeptide portions derived from two separate structural sequences. This may be accomplished by inserting all or part of a heterologous structural sequence into the structural sequence of a plant gene, somewhere after the start codon of the plant structural sequence.

As used herein, the phrase, "a promoter region derived from a specified gene" shall include a promoter region if one or more parts of the promoter region were derived from the specified gene. For example, it might be discovered that one or more portions of a particular plant-derived promoter region (such as intervening region 8, shown on FIG. 12) might be replaced by one or more sequences derived from a different gene, such as the gene that contains the heterologous structural sequence, without reducing the expression of the resulting chimeric gene in a particular type of host cell. Such a chimeric gene would contain a plant-derived association region 2, intervening region 4, and transcription initiation sequence 6, followed by heterologous intervening region 8, 5' non-translated region 10 and structural sequence 14. Such a chimeric gene is within the scope of this invention.

As used herein, the phrase "derived from" shall be construed broadly. For example, a structural sequence may be "derived from" a particular gene by a variety of processes, including the following:

1. The gene may be reproduced by various means such as inserting it into a plasmid and replicating the plasmid by cell culturing, in vitro replication, or other methods, and the desired sequence may be obtained from the DNA copies by various means such as endonuclease digestion;
2. mRNA which was coded for by the gene may be obtained and processed in various ways, such as preparing complementary DNA from the mRNA and then digesting the cDNA with endonucleases;
3. The sequence of bases in the structural sequence may be determined by various methods, such as endonuclease mapping or the Maxam-Gilbert method. A strand of DNA which duplicates or approximates the desired sequence may be created by various methods, such as chemical synthesis or ligation of oligonucleotide fragments.
4. A structural sequence of bases may be deduced by applying the genetic code to the sequence of amino acid residues in a polypeptide.

Usually, a variety of DNA structural sequences may be determined for any polypeptide, because of the redundancy of the genetic code. From this variety, a desired sequence of bases may be selected, and a strand of DNA having the selected sequence may be created.

If desired, any DNA sequence may be modified by substituting certain bases for the existing bases. Such modifications may be performed for a variety of reasons. For example, one or more bases in a sequence may be replaced by other bases in order to create or delete a cleavage site for a particular endonuclease. As another example, one or more bases in a sequence may be replaced in order to reduce the occurrence of "stem and loop" structures in messenger RNA. Such modified sequences are within the scope of this invention.

A structural sequence may contain introns and exons; such a structural sequence may be derived from DNA, or from an mRNA primary transcript. Alternately, a structural sequence may be derived from processed mRNA, from which one or more introns have been deleted.

The Applicants have deposited two cultures of *E. coli* cells containing plasmids pMON128 and pMON154 with the American Type Culture Collection (ATCC). These cells have been assigned ATCC accession numbers 39264 and 39265, respectively.

The Applicants have deposited two cultures of *E. coli* cells containing plasmids pMON120 and pMON128 and a culture of *A. tumefaciens* containing a pMON128::Ti cointegrate plasmid, with the American Type Culture Collection (ATCC). These cells have been assigned ATCC accession numbers 39263, 39264, and 39266, respectively. The Applicants have claimed cultures of microorganisms having the "relevant characteristics" of these cultures. As used herein, the "relevant characteristics" of a cell culture are limited to those characteristics which make the culture suitable for a use which is disclosed, suggested or made possible by the information contained herein. Numerous characteristics of the culture may be modified by techniques known to those skilled in the art; for example, the cells may be made resistant to a particular antibiotic by insertion of a particular plasmid or gene into the cells, or the specified plasmids might be removed from the designated cells and inserted into a different strains of cells. Such variations are within the scope of this invention, even though they may amount to improvements in the culture, which undoubtedly will occur after more researchers gain access to these cell cultures.

Those skilled in the art will recognize, or be able to ascertain using no more than routine experimentation, numerous equivalents to the specific embodiments of the invention discussed herein. Such equivalents are within the scope of this invention.

EXAMPLE 1

Creation of Plasmid pMON41

A culture of *E. coli*, carrying a pBR325 plasmid (Bolivar, 1978) with the HindIII-23 fragment of pTiT37 (Hernalsteens, et al, 1980) inserted at the HindIII site, was obtained from Drs. M. Bevan and M. D. Chilton, Washington University, St. Louis, Mo. Ten micrograms (ug) of the plasmid from this clone was digested with 10 units of HindIII (unless noted, all restriction endonucleases used in these constructions were purchased from New England Biolabs, Beverly, Mass. and used with buffers according to the supplier's instructions) for 1 hour at 37° C. The 3.4 kb HindIII-23 fragment was purified by adsorption on glass beads (Vogelstein and Gillespie, 1979) after separation from the other HindIII fragments by electrophoresis on a 0.8% agarose gel. The purified 3.4 kb HindIII fragment (1.0 ug) was mixed with 1.0 ug of plasmid pBR327 DNA (Soberon, et al, 1980) that had been digested with both HindIII (2 units, 1 hour, 37° C.) and calf alkaline phosphatase (CAP; 0.2 units, 1 hour, 37° C.), de-proteinized with phenol, ethanol precipitated, and resuspended in 10 ul of TE (10 mM Tris HCl, pH8, 1 mM EDTA). One unit of T4 DNA ligase (prepared by the method of Murray et al, 1979) was added to the fragment mixture. One unit is defined as the concentration sufficient to obtain greater than 90% circularization of one microgram of HindIII linearized pBR327 plasmid in 5 minutes at 22° C. The mixed fragments were contained in a total volume of 15 ul of 25 mM Tris-HCl pH8, 10 mM $MgCl_2$, 1 mM dithioheitol, 200 uM spermidine HCl and 0.75 mM ATP (ligase buffer).

The mixture was incubated at 22° for 3 hours and then mixed with *E. coli* C600 recA56 cells that were prepared for transformation by treatment with $CaCl_2$ (Maniatis et al, 1982). Following a period for expression of the ampicillin resistance determinant carried by the pBR327 vector, cells were spread on LB solid medium plates (Miller, 1972) containing ampicillin at 200 ug/ml. After incubation at 37° C. for 16 hours, several hundred clones were obtained. Plasmid mini-preps (Ish-Horowicz and Burke, 1981) were performed on 24 of these colonies and aliquots of the plasmid DNA's obtained (0.1 ug) were digested with HindIII to demonstrate the presence of the 3.4 kb HindIII fragment. One plasmid demonstrated the expected structure and was designated pMON38. pMON38 DNA were prepared by Triton X-100 lysis and CsC1 gradient procedure (Davis et al, 1980).

Fifty ug of pMON38 DNA were digested with HindIII and BamHI (50 units each, 2 hours, 37°) and the 2.3 kb HindIII-BamHI fragment was purified as described above. The purified fragment (1 ug) was mixed with 1 ug of the 2.9 kb HindIII-BamHI fragment of the pBR327 vector purified as described above. Following ligation (T4 DNA ligase, 2 units) and transformation of E. coli cells as described above, fifty ampicillin-resistant colonies were obtained. DNAs from twelve plasmid mini-preps were digested with HindIII and BamHI to ascertain the presence of the 2.3 kb fragment. One plasmid of the correct structure was chosen and designated pMON41, as shown in FIG. 2. A quantity of this DNA was prepared as described above.

EXAMPLE 2

Creation of M13 Clone M-4

Thirty ug of plasmid pMON38 (described in Example 1) were digested with RsaI (30 units, 2 hours, 37° C.) and the 1100 bp RsaI fragment was purified after separation by agarose gel electrophoresis using the glass bead method described in the previous example. The purified 1100 bp RsaI-RsaI fragment (1 ug) was digested with 2 units of BamHI and the BamHI was inactivated by heating. This DNA was mixed with 0.2 ug of phage M13 mp8RF DNA which had been previously digested with SmaI and BamHI (2 units each, 1 hour, 37°) and 0.2 units of calf alkaline phosphotase (CAP). Following ligation with 100 units of T4 DNA ligase, transformation of E. coli JM101 cells as described in the previous example, the transformed cells were mixed with soft agar and plated under conditions that allow the identification of recombinant phage (Messing and Vieira, 1982). Twelve recombinant phage producing cells were picked and RF plasmid mini-preps were obtained as described in the previous example. The RF DNAs were digested with BamHI and SmaI to prove the presence of the 720 bp RsaI-BamHI fragment. One of the recombinant RF DNAs carrying the correct fragment was designated M13 mp8 M-4. This procedure is represented in FIG. 3. M-4 RF DNA was prepared using the procedures of Ish-Horowicz and Burke, 1981 and Colman et al, 1978.

EXAMPLE 3

Construction of pMON109

Twenty ug of plasmid pGV3106 (Hernalsteens et al 1980, prepared by the method of Currier and Nester 1976) was digested with HindIII (20 units, 2 hours, 37°) and mixed with 2 ug of HindIII-digested pBR327. Following ligation (T4 DNA ligase, 2 units) and transformation of E. coli cells as described above, one colony resistant to trimethoprim (100 ug/ml) and ampicillin was obtained. Digestion of plasmid DNA from this cell demonstrated the presence of a 6 kb HindIII fragment. This plasmid was designated pMON31.

Plasmid pMON31 from a mini-prep (0.5 ug) was digested with EcoRI (1 unit, 1 hour, 37° C.) and the endonuclease was inactivated by heating (10 min, 70° C.). The 8.5 kb plasmid fragment was re-circularized in a ligation reaction of 100 ul (T4 DNA ligase, 1 unit) and used to transform E. coli cells with selection for ampicillin and streptomycin (25 ug/ml) resistant colonies. Plasmid mini-prep DNA's from six clones were digested with EcoRI to ascertain loss of the 850 by fragment. One plasmid lacking the 850 bp EcoRI fragment was designated pMON53. This plasmid was introduced into E. coli GM42 dam⁻ cells (Bale et al, 1979) by transformation as described.

Plasmid pMON53 (0.5 ug) from a mini-prep prepared from dam cells was digested with ClaI, and recircularized in dilute solution as described above. Following transformation of E. coli GM42 cells and selection for ampicillin and spectinomycin (50 ug/ml) resistant clones, fifty colonies were obtained. Digestion of plasmid mini-prep DNA's from six colonies showed that all lacked the 2 kb ClaI fragment. One of these plasmids was designated pMON54, as represented in FIG. 4. Plasmid DNA was prepared as described in Example 1.

Plasmid pMON54 DNA (20 ug) was digested with EcoRI and PstI (20 units of each, 2 hours, 37° C.) and the 5.7 kb fragment was purified from agarose gels using NA-45 membrane (Schleicher and Schuell, Keene, N. H.).

The purified 5.7 kb fragment (0.5 ug) was mixed with 0.3 ug of a 740 bp EcoRI-PstI fragment obtained from M13 mp8 M-4 RF DNA (described in Example 2) which was purified using NA-45 membrane. Following ligation (T4 DNA ligase, 2 units), transformation of E. coli GM42 dam⁻ cells, and selection for spectinomycin resistant cells, twenty colonies were obtained. Plasmid mini-prep DNA's prepared from twelve of these clones were digested with PstI and EcoRI to demonstrate the presence of the 740 bp fragment. One plasmid carrying this fragment was designated pMON64. quantity of this plasmid DNA was prepared as described in Example 1.

DNA (0.5 ug) of pMON64 was digested with ClaI (1 unit, 1 hour, 37° C.), the ClaI was heat inactivated, and the fragments rejoined with T4 DNA ligase (1 unit). Following transformation and selection for spectinomycin resistant cells, plasmid mini-preps from twelve colonies were made. The DNA's were digested with BamHI and EcoRI to determine the orientation of the 2 kb ClaI fragment. Half of the clones contained the ClaI fragment in the inverse orientation of that in pMON64. One of these plasmids was designated pMON109, as represented in FIG. 5. DNA was prepared as described in Example 1.

EXAMPLE 4

Creation of Plasmid pMON113

Plasmid pNW31C-8,29C (Thomashow et al, 1980) was obtained from Dr. S. Gelvin of Purdue University, West Lafayette, I N. This plasmid carries the pTiA6 7.5 kb Bam-8 fragment. The Bam-8 fragment was purified from 50 ug of BamHI-digested pNW31C-8,29C using NA-45 membrane as described in previous examples. The purified 7.5 kb Bam-8 fragment (1.0 ug) was mixed with 0.5 ug of pBR327 vector DNA which had been previously digested with both BamHI (2 units) and 0.2 units of calf alkaline phosphatase (CAP) for 1 hour at 37°; the mixture was deproteinized and resuspended as described in previous examples. The mixed fragments were treated with T4 ligase (2 units), used to transform E. coli C600 recA cells and ampicillin-resistant colonies were selected as described previously. Mini-preps to obtain plasmid DNA were performed on twelve of these clones. The DNA was digested with BamHI to demonstrate the presence of the pBR327 vector and 7.5 kb Bam-8 fragments. One plasmid demonstrating both fragments was designated pMON90. DNA was prepared as described in Example 1.

Twenty-five ug of pMON90 DNA were digested with BglII (25 units, 2 hours, 37°) and the 2.6 kb BglII fragment was purified using NA-45 membrane. To create blunt ends, the fragment (2 ug) was resuspended in 10 ul of 50 mM NaCl, 6.6 mM Tris-HCl pH8, 6.6 mM $MgCl_2$ and 0.5 mM dithiothreitol (Klenow Buffer). The 4 deoxy-nucleoside triphosphates (dATP, dTTP, dCTP, and dGTP) were added to a final concentration of 1 mM and one unit of E. coli large Klenow fragment of DNA polymerase I (New England Biolabs, Beverly, Mass.) was added. After incubation for 20 minutes at 22° C., the Klenow polymerase was heat inactivated and 10 units of HindIII was added. The HindIII digestion was carried out for 1 hour at 37° and then the enzyme was heat inactivated. The HindIII-BglII (blunt) fragments (1 ug) were added to 0.25 ug of the 2.2 kb HindIII-PvuII fragment of pBR322 (Bolivar, et al, 1977) which had been generated by HindIII and PvuII digestion then treating with calf alkaline phosphatase as described in previous examples. After ligation using 100 units of T4 DNA ligase, transformation of E. coli LE392 cells and selection of ampicillin-resistant colonies as described in previous examples, nineteen colonies were obtained. Plasmid mini-preps were prepared from twelve colonies and digested with HindIII to determine the size of the recombinant plasmid and with Sinai to determine that the correct fragment had been inserted. One plasmid with the correct structure was designated pMON113, as shown in FIG. 6. Plasmid DNA was prepared as described in Example 1.

EXAMPLE 5

Creation of Plasmid pMON120

Twenty ug of plasmid pMON109 (described in Example 3) were digested with EcoRI and BamHI (20 units each, 2 hours, 37° C.) and the 3.4 kb BamHI-EcoRI fragment was purified using NA-45 membrane as described in previous examples. Twenty ug of plasmid pMON41 (described in Example 1) were digested with BamHI and PvuI (20 units each, 2 hours, 37° C.) and the 1.5 kb BamHI-PvuI fragment purified using NA-45 membrane as described in previous examples.

Twenty ug of pMON113 DNA (described in Example 4) were digested with PvuI and EcoRI (2 units each, 2 hr, 37° C.) and the 3.1 kb PvuI-EcoRI fragment was purified using NA-45 membrane as above. To assemble plasmid pMON120, the 3.1 kb EcoRI-PvuI pMON113 fragment (1.5 ug) was mixed with 1.5 ug of the 3.4 kb EcoRI-BamHI fragment from pMON109. After treatment with T4 ligase (3 units) for 16 hours at 10° C., the ligase was inactivated by heating (10 minutes, 70° C.), and 5 units of BamHI was added. Digestion continued for 30 minutes at 37° at which time the BamHI endonuclease was inactivated by heating as above. Next, 0.75 ug of the 1.5 kb PvuI-BamHI fragment from pMON41 was added along with T4 DNA ligase (2 units) and fresh ATP to 0.75 mM final concentration. The final ligase reaction was carried out for 4 hours at 22° C. at which time the mixture was used to transform E. coli LE 392 cells with subsequent selection for spectinomycin resistant cells as described previously. Plasmid mini-preps from twelve out of several thousand colonies were screened for plasmids of approximately 8 kb in size containing single sites for BamHI and EcoRI. One plasmid showing the correct structure was designated pMON120, which is shown in FIG. 7 with an alternate method of construction. pMON120 DNA was prepared as described in Example 1.

A culture of E. coli containing pMON120 has been deposited with the American Type Culture Collection. This culture has been assigned accession number 39263.

EXAMPLE 6

Creation of Plasmids pMON128 and pMON129

Plasmid pMON75 (described in detail in a separate application entitled "Chimeric Genes Suitable for Expression in Plant Cells," previously cited and incorporated contains a chimeric NOS-NPT II-NOS gene. This plasmid (and pMON128, described below) may be digested by EcoRI and a 1.5 kb fragment may be purified which contains the NOS-NPT II-NOS gene.

Plasmid pMON120 was digested with EcoRI and treated with calf alkaline phosphatase. After phenol deproteinization and ethanol precipitation, the EcoRI-cleaved pMON120 linear DNA was mixed with 0.5 ug of the 1.5 kb EcoRI chimeric gene fragment from pMON75 or 76. The mixture was treated with 2 units of T4 DNA ligase for 1 hour at 22°. After transformation of E. coli cells and selection of colonies resistant to spectinomycin (50 ug/ml), several thousand colonies appeared. Six of these were picked, grown, and plasmid mini-preps made. The plasmid DNA's were digested with EcoRI to check for the 1.5 kb chimeric gene insert and with BamHI to determine the orientation of the insert. BamHI digestion showed that in pMON128 the chimeric gene was transcribed in the same direction as the intact nopaline synthase gene of pMON120. A culture of E. coli containing pMON128 has been deposited with the American Type Culture Collection. This culture has been assigned accession number 39264. The orientation of the insert in pMON129 was opposite that in pMON128; the appearance of an additional 1.5 kb BamHI fragment in digests of pMON129 showed that plasmid pMON129 carried a tandem duplication of the chimeric NOS-NPT II-NOS gene, as shown in FIG. 8.

EXAMPLE 7

Creation of Co-integrate Plasmid pMON128::pTiB6S3Tra$^C$

Plasmid pMON128 (described in Example 6) was transferred to a chloramphenicol resistant Agrobacterium tumefaciens strain GV3111=C58C1 carrying Ti plasmid pTiB6S3tra$^C$ (Leemans, et al, 1982) using a tri-parental plate mating procedure, as follows. 0.2 ml of a culture of E. coli carrying pMON128 was mixed with 0.2 ml of a culture of E. coli strain HB101 carrying a pRK2013 plasmid (Ditta, et al, 1980) and 0.2 ml of GV3111 cells. The mixture of cells was cultured in Luria Broth (LB), spread on an LB plate, and incubated for 16 to 24 hours at 30° C. to allow plasmid transfer and generation of co-integrate plasmids. The cells were resuspended in 3 ml of 10 mM $MgSO_4$ and 0.2 ml aliquot was then spread on an LB plate containing 25 ug/ml chloramphenicol and 100 ug/ml each of spectinomycin and streptomycin. After incubation for 48 hr at 30°, approximately 10 colonies were obtained. One colony was chosen and grow at 30° C. in LB medium containing chloramphenicol, spectinomycin, and streptomycin at the concentrations given above.

A separate type of co-integrate plasmid for use in control experiments was prepared by inserting pMON120 into A. tumefaciens cells, and selecting for cells with co-integrate plasmids using spectinomycin and streptomycin, as described above. Like pMON120, these plasmids do not contain the chimeric NOS-NPT II-NOS gene.

EXAMPLE 8

Solutions Used in Plant Cell Cultures

The following solutions were used by the Applicants:

|  |  | per liter |
|---|---|---|
| Enzyme mix: | Cellulysin | 5 g |
|  | Macerozyme | 0.7 g |
|  | Ampicillin | 0.4 g |
|  | $KH_2PO_4$ | 27.2 mg |
|  | $KNO_3$ | 101 mg |
|  | $CaCl_2$ | 1.48 g |
|  | $MgSO_4 \cdot 7H_2O$ | 246 mg |
|  | KI | 0.16 mg |
|  | $CuSO_4 \cdot 5H_2O$ | 0.025 mg |
|  | Mannitol | 110 g |
| MS9: | MS salts(see below) | 4.3 g |
|  | Sucrose | 30.0 g |
|  | B5 vitamins (see below) | 1 ml |
|  | Mannitol | 90.0 g |
|  | Phytohormones: |  |
|  | Benzyladenine (BA) | 0.5 mg |
|  | 2,4-D | 1 mg |
| MS-ES | MS salts | 4.3 g |
|  | Sucrose | 30 g |
|  | B5 Vitamins | 1 ml |
|  | Mannitol | 30 g |
|  | Carbenicillin | 10 mg |
|  | Phytohormones: |  |
|  | Indole acetic acid | 0.1 mg |
| MSO: | MS salts | 4.3 g |
|  | Sucrose | 30.0 g |
|  | B5 vitamins | 1 ml |
| Feeder plate | MS salts | 4.3 g |
| medium: | Sucrose | 30.0 g |
|  | B5 vitamins | 1 ml |
|  | Mannitol | 30.0 g |
|  | Phytohormones: |  |
|  | BA | 0.5 mg |
| Ms2C | MS salts | 4.3 g |
|  | Sucrose | 30 g |
|  | B5 vitamins | 1 ml |
|  | Phytohormones: |  |
|  | chlorophenoxyacetic acid | 2 mg |
| MS104: | MS salts | 4.3 g |
|  | Sucrose | 30.0 g |
|  | B5 vitamins | 1 ml |
|  | Phytohormones: |  |
|  | BA | 0.1 mg |
|  | NAA | 1 mg |
| MS11: | MS salts | 4.3 g |
|  | Sucrose | 30.0 g |
|  | B5 vitamins | 1 ml |
|  | Phytohormones: |  |
|  | Zeatin | 1 mg |
| B5 Vitamin | myo-inositol | 100 g |
| stock: | thiamine HCl | 10 g |
|  | nicotinic acid | 1 g |
|  | pyrodoxine HCl | 1 g |
| Float rinse: | MS salts | 0.43 g |
|  | Sucrose | 171.2 g |
|  | PVP-40 | 40.0 g |

MS salts are purchased pre-mixed as a dry powder from Gibco Laboratories, Grand Island, N.Y.

EXAMPLE 9

Preparation of Protoplasts

Mitchell petunia plants were grown in growth chambers with two or three banks of fluorescent lamps and two banks of incandescent bulbs (about 5,000 lux). The temperature was maintained at a constant 21° C. and the lights were on for 12 hours per day. Plants were grown in a 50/50 mix of Vermiculite and Pro-mix BX (Premier Brands Inc., Canada). Plants were watered once a day with Hoagland's nutrient solution. Tissue was taken from dark green plants with compact, bushy growth. Leaves were sterilized in a solution of 10% commercial bleach and a small amount of detergent or Tween 20 for 20 minutes with occasional agitation. Leaves were rinsed two or three times with sterile distilled water, Thin strips (about 1 mm) were cut from the leaves, perpendicular to the main rib. The strips were placed in the enzyme mix at a ratio of about 1 g tissue to 10 ml enzymes. The dishes were sealed with parafilm, and incubated in the dark or under low, indirect light while gently agitating continuously (e.g., 40 rpm on gyrotary shaker). Enzymic incubations generally were run overnight, about 16-20 hours.

The digestion mixture was sieved through a 68, 74, or 88 um screen to remove large debris and leaf material. The filtrate was spun at 70-100 g for five minutes to pellet the protoplasts. The supernatant was decanted and the pellet was gently resuspended in float rinse solution. This suspension was poured into babcock bottles. The bottles were filled to 2 or 3 cm above the base of the neck. 1 ml of growth medium MS9 was carefully layered on top of the float rinse.

The Babcock bottles were balanced and centrifuged at 500 to 1000 rpm for 10 to 20 minutes. The protoplasts formed a compact band in the neck at the interface. The band was removed with a pipette, taking care not to pick up any excess float rinse. The protoplasts were diluted into MS9. At this point, the protoplasts were washed with MS9 or diluted for plating without washing.

Protoplasts were suspended in MS9 medium at $5 \times 10^4$ per ml, and plated into T-75 flasks, at 6 ml per flask. Flasks were incubated on a level surface with dim, indirect light or in the dark at 26-28° C. On the third day following the removal of the enzymes from the leaf tissue, MSO (medium which does not contain mannitol) was added to each flask, using an amount equal to one-half the original volume. The same amount of MSO is added again on day 4. This reduces the mannitol concentration to about 0.33 M after the first dilution, and about 0.25 M after the second dilution.

EXAMPLE 10

Co-Cultivation with Bacteria

On day 5 following protoplast isolation, five to seven day old tobacco suspension cultures (TXD cells) were diluted (if necessary) with MS2C medium to the point where 1 ml would spread easily over the surface of agar medium in a 100×15 mm petri plate [this is a 10 to 15% suspension (w/v)]. The agar medium was obtained by mixing 0.8% agar with MS-ES medium, autoclaving the mixture, and cooling the mixture until it solidifies in the plate. One ml of the TXD suspension was spread over 25 ml of feeder plate medium. An 8.5 cm disc of Whatman #1 filter paper was laid over the TXD feeder cells and smoothed out. A 7 cm disc of the same paper was placed in the center of the larger one.

Separately, aliquots of a culture of *A. tumefaciens* cells (grown in yeast extract peptone medium) were added to the flasks which contained the plant cells. One set of aliquots contained cells with the pMON128::Ti co-integrate plasmids having chimeric NOS-NPT II-NOS genes. The other set of aliquots contained cells with the pMON120::Ti co-integrate plasmids, which do not have chimeric NOS-NPT II-NOS genes.

The bacteria were added to the flasks to a density of $10^8$ cells/ml. 0.5 ml of the cell mixture was spread in a thin layer on the surface of the 7 cm filter paper disc. The plates were wrapped in parafilm or plastic bags and incubated under direct fluorescent lighting, no more than five plates in a stack.

Within seven days, colonies were discernable. Within 14 days, the 7 cm discs, with colonies adhering to them, were transferred to new MSO agar medium (without feeder cells) _containing 500 ug/ml carbenicillin, as well as 50 ug/ml of kanamycin sulfate (Sigma, St. Louis, Mo.). Within two weeks, vigorously growing green colonies could be observed on the plates which contained plant cells that had been co-cultured with *A. tumefaciens* strains containing the pMON128 co-integrate NOS-NPT II plasmid. No transformed colonies were detected on plates which contained plant cells that had been co-cultured with *A. tumefaciens* strains containing the pMON120 co-integrate plasmid. The kanamycin resistant transformants are capable of sustained growth in culture medium containing kanamycin. Southern blotting experiments (as described in E. Southern, *J. Mol. Biol.* 98: 503 (1975) confirmed that these cells contain the chimeric NOS-NPT II gene.

Figure 11:
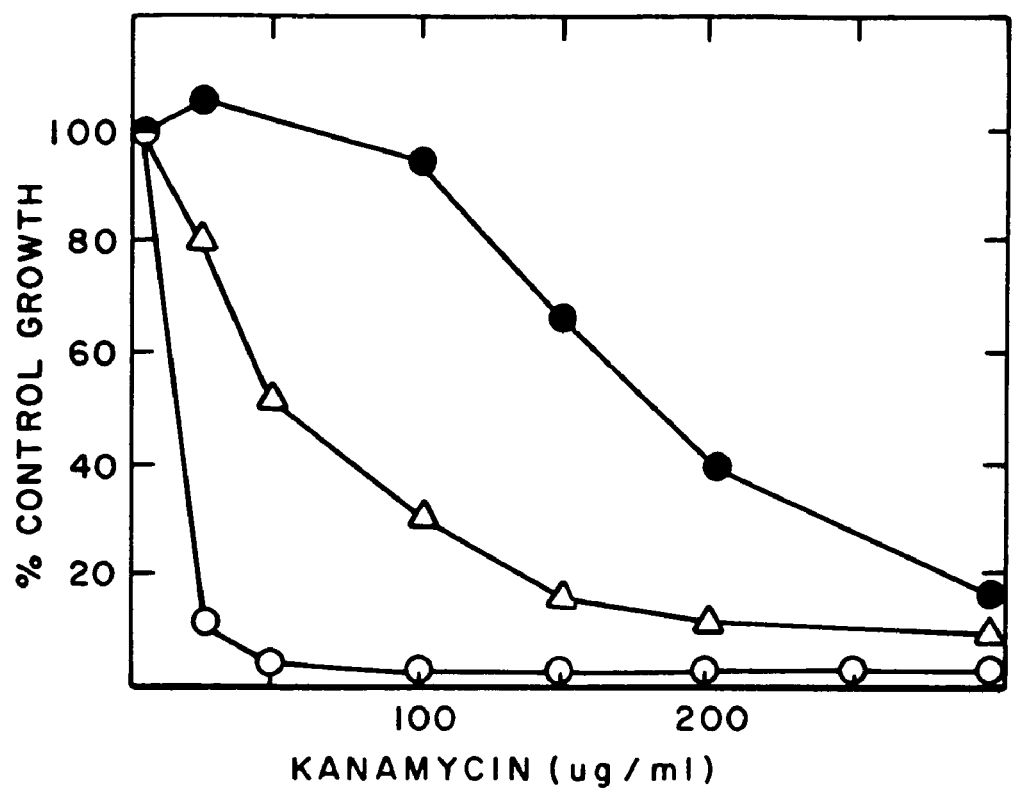
FIG. 11 is a graph comparing growth of transformed cells and non-transformed cells on kanamycin-containing medium.

Both sets of transformed cells (and a third set of cells which had been transformed in the same manner by a chimeric gene coding for the enzyme NPT type I) were assayed for resistance to kanamycin. The results are indicated in FIG. 11.

EXAMPLE 11

Regeneration of Transformed Plants

The transformed kanamycin-resistant colonies described in Example 10 contained both tumorous and non-tumorous cells, as described in FIG. 9 and the related text. The following procedure was used to isolate non-tumorous transformed cells from tumorous transformed cells, and to regenerate differentiated plant tissue from the non-tumorous cells.

Colonies were grown on MS104 agar medium containing 30 ug/ml kanamycin sulfate and 500 ug/ml carbenicillin until they reached about 1 cm in diameter. Predominantly tumorous colonies appear a somewhat paler shade of green and are more loosely organized than predominantly non-tumorous colonies. Predominantly non-tumorous colonies were removed from the MS104 medium and placed upon MS11 medium containing 30 ug/ml kanamycin and 500 ug/ml carbenicillin. As the colonies continued to grow, colonies that appeared pale green and loosely organized were removed and discarded.

MS11 medium contains zeatin, a phytohormone which induces shooting formation in non-tumorous colonies. Several shoots were eventually observed sprouting from kanamycin-resistant colonies. These shoots may be grown to a desired size, cut off by a sharp blade, and inserted into agar medium without phytohormones, such as MSO, where they may generate roots. If desired, the medium may be supplemented by napthalene acetic acid to induce shooting. The shoots may be grown to a desired size in the agar medium, and then transferred into soil. If properly cultivated, such plants will grow to maturity and generate seed. The acquired trait will be inherited by progeny according to classic Mendelian genetics.

EXAMPLE 12

Creation Of pMON1001

Fifty micrograms (ug) of lambda phage bbkan-1 DNA (Berg et al, 1975) were digested with 100 units of HindIII (all restriction endonucleases were obtained from New England Biolabs, Beverly, Mass., and were used with buffers according to the suppliers instructions, unless otherwise specified) for 2 hours at 37° C. After heat-inactivation (70° C., 10 minutes), the 3.3 kb Tn5 HindIII fragment was purified on a sucrose gradient. One ug of the purified HindIII fragment was digested with BamHI (2 units, 1 hr, 37° C.), to create a 1.8 kb fragment. The endonuclease was heat inactivated.

Plasmid pBR327 (Soberon et al, 1981), 1 ug, was digested with HindIII and BamHI (2 units each, 2 hours, 37° C.) Following digestion, the endonucleases were heat inactivated and the cleaved pBR327DNA was added to the BamHI-HindIII Tn5 fragments. After addition of ATP to a concentration of 0.75 mM, 10 units of T4 DNA ligase (prepared by the method of Murray et al, 1979) was added, and the reaction was allowed to continue for 16 hours at 12°-14° C. One unit of T4 DNA ligase will give 90% circularization of one ug of HindIII-cleaved pBR327 plasmid in 5 minutes at 22° C.

The ligated DNA was used to transform $CaCl_2$-shocked *E. coli* C600 recA56 cells (Maniatis et al, 1982). After expression in Luria broth (LB) for 1 hour at 37° the cells were spread on solid LB media plates containing 200 ug/ml ampicillin and 40 ug/ml kanamycin. Following 16 hours incubation at 37° C., several hundred colonies appeared. Plasmid mini-prep DNA was prepared from six of these. (Ish-Horowicz and Burke, 1981). Endonuclease digestion showed that all six of the plasmids carried the 1.8 kb HindIII-BamHI fragment. One of those isolates was designated as pMON1001 as shown in FIG. 17.

EXAMPLE 13

Creation of pMON40

Five ug of plasmid pMON1001 (described in Example 12) was digested with SmaI. The reaction was terminated by phenol extraction, and the DNA was precipitated by ethanol. A BamHI linker CCGGATCCGG (0.1 ug), which had been phosphorylated with ATP and T4 polynucleotide kinase (Bethesda Research Laboratory, Rockville, Md.) was added to 1 ug of the pMON 1001 fragment. The mixture was treated with T4 DNA ligase (100 units) for 18 hours at 14° C. After heating at 70° C. for 10 minutes to inactivate the DNA ligase, the DNA mixture was digested with BamHI endonuclease (20 units, 3 hours, 37° C.) and separated by electrophoresis on an 0.5% agarose gel. The band corresponding to the 4.2 kb SmaI-BamHI vector fragment was excised from the gel. The 4.2 kb fragment was purified by absorption on glass beads (Vogelstein and Gillespie, 1979), ethanol precipitated and resuspended in 20 ul of DNA ligase buffer with ATP. T4 DNA ligase (20 units) was added and the mixture was incubated for 1.5 hours at room temperature. The DNA was mixed with rubidium chloride-shocked in *E. coli* C600 cells for DNA transformation. (Maniatis et al, 1982). After expression for 1 hour at 37° C. in LB, the cells were spread on LB plates containing 200 ug/ml of ampicillin and 20 ug/ml kanamycin. The plates were incubated at 37° C. for 16 hours. Twelve ampicillin-resistant, kanamycin-resistant colonies were chosen, 2 ml cultures were grown, and mini-plasmid preparations were performed. Endonuclease mapping of the plasmids revealed that ten of the twelve contained no SmaI site and a single BamHI site, and were of the appropriate size, 4.2 kb. The plasmid from one of the ten colonies was designated as pMON40, as shown in FIG. 17.

EXAMPLE 14

Creation of NOS Promoter Fragment

An oligonucleotide with the following sequence, 5'-TG-CAGATTATTTGG-3', was synthesized (Beaucage and Carruthers, 1981, as modified by Adams et al, 1982). This oligonucleotide contained a $^{32}$P radioactive label, which was added to the 5' thymidine residue by polynucleotide kinase.

An M13 mp 7 derivative, designated as S1A, was given to Applicants by M. Bevan and M. D. Chilton, Washington University, St. Louis, Mo. To the best of Applicants' knowledge and belief, the S1A DNA was obtained by the following method. A pTiT37 plasmid was digested with HindIII, and a 3.4 kb fragment was isolated and designated as the HindIII-23 fragment. This fragment was digested with Sau3a, to create a 344 bp fragment with Sau3a ends. This fragment was inserted into double-stranded, replicative form DNA from the M13 mp 7 phage vector (Messing et al, 1981) which had been cut with BamHI. Two recombinant phages with 344 bp inserts resulted, one of which contained the anti-sense strand of the NOS promoter fragment. That recombinant phage was designated as S1A, and a clonal copy was given to the Applicants.

The Applicants prepared the single-stranded form of the S1A DNA (14.4 ug; 6 pmol), and annealed it (10 minutes at 70° C., then cooled to room temperature) with 20 pmol of the 14-mer oligonucleotide, mentioned above. The oligonucleotide annealed to the Sau3a insert at bases 286-300 as shown on FIGS. 15 and 16.

200 ul of the S1A template and annealed oligonucleotide were mixed with the four dNTP's (present at a final concentration of 1 mM, 25 ul) and 50 ul of Klenow polymerase. The mixture incubated for 30 minutes at room temperature. During this period, the polymerase added dNTP's to the 3' end of the oligonucleogide. The polymerase was heat-inactivated (70° C., 3 minutes), and HaeIII (160 units) were added. The mixture was incubated (1 hour, 55° C.), the HaeIII was inactivated (70° C., 3 minutes), and the four dNTP's (1 mM, 12 ul) and T4 DNA polymerase (50 units) were added. The mixture was incubated (1 hour, 37° C.) and the polymerase was inactivated (70° C., 3 minutes). This yielded a fragment of about 570 bp. EcoRI (150 units) was added, the mixture was incubated (1 hour, 37° C.) and the EcoRI was inactivated (70° C., 3 minutes).

Aliquots of the mixture were separated on 6% acrylamide with 25% glycerol. Autoradiography revealed a radioactively labelled band about 310 bp in size. This band was excised. The foregoing procedure is indicated by FIG. 16.

EXAMPLE 15

Creation of pMON58

Figure 18:
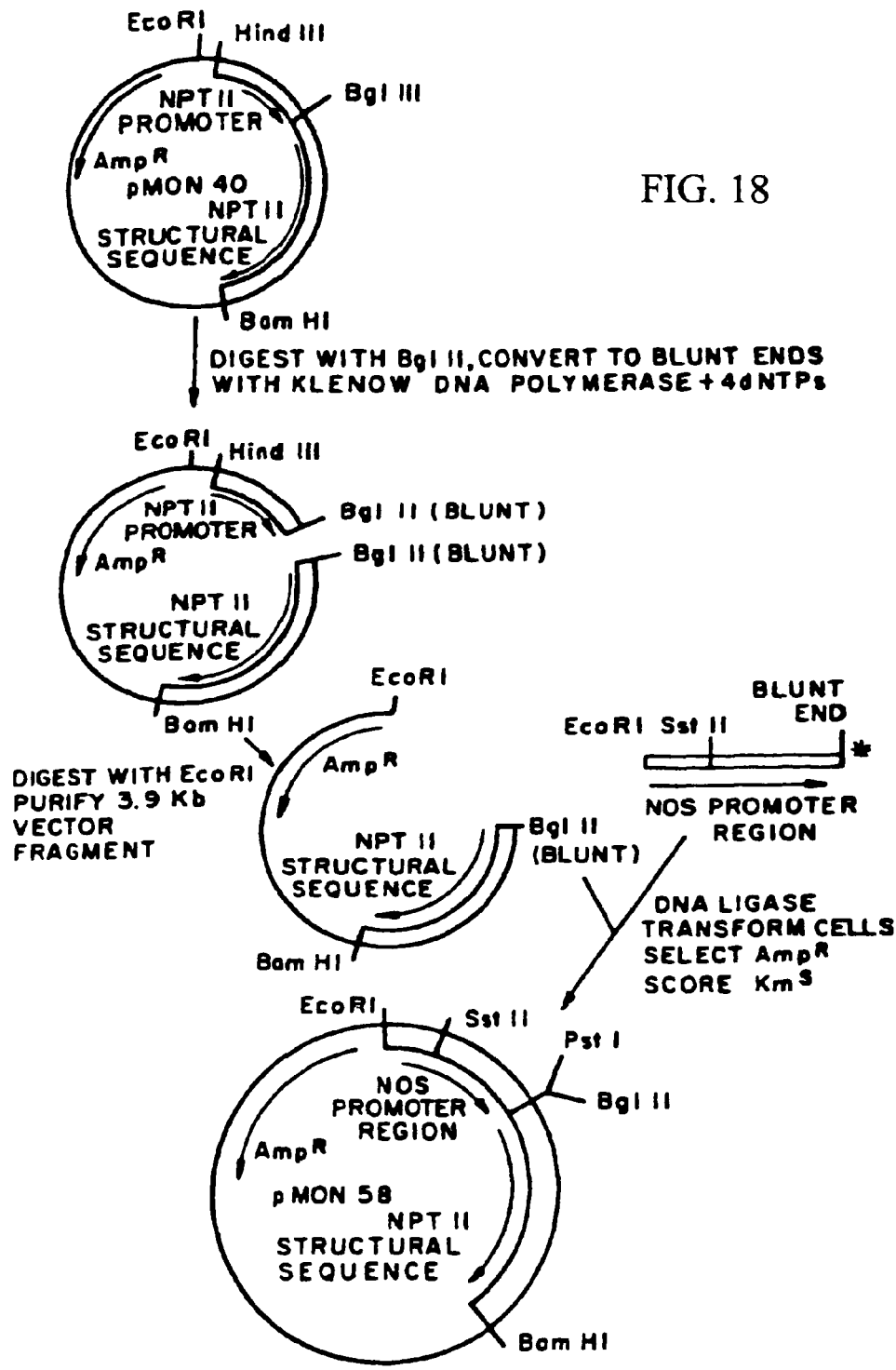
FIG. 18 represents the insertion of a NOS promoter region into plasmid pMON40, to obtain pMON58.

Five ug of plasmid pMON40 (described in Example 13) were digested with BglII (10 units, 1.5 hour, 37° C.), and the BglII was inactivated (70° C., 10 minutes). The four dNTP's (1 mM, 5 ul) and Klenow polymerase (8 units) were added, the mixture was incubated (37° C., 40 minutes), and the polymerase was inactivated (70° C., 10 minutes). EcoRI (10 units) was added and incubated (1 hour, 37° C.), and calf alkaline phosphatase (CAP) was added and incubated (1 hour, 37° C.). A fragment of about 3.9 kb was purified on agarose gel using NA-45 membrane (Scheicher and Scheull, Keene N H). The fragment (1.0 pM) was mixed with the NOS promoter fragment (0.1 pM), described in Example 3, and with T4 DNA ligase (100 units). The mixture was incubated (4° C., 16 hours). The resulting plasmids were inserted into E. coli cells, which were selected on media containing 200 ug/ml ampicillin. Thirty-six clonal Amp$^R$ colonies were selected, and mini-preps of plasmids were made from those colonies. The plasmid from one colony demonstrated a 308 by EcoRI-BglII fragment, a new SstII cleavage site carried by the 308 bp NOS fragment, and a new PstI site. This plasmid was designated as pMON58, as shown in FIG. 18. pMON58 DNA was prepared as described above.

EXAMPLE 16

Creation of pMON42

Plasmid pBR325-HindIII-23, a derivative of plasmid pBR325 (Bolivar, 1978) carrying the HindIII-23 fragment of pTIT37 (see FIG. 14) in the HindIII site, was given to Applicants by M. Bevan and M. D. Chilton, Washington University, St. Louis, Mo. DNA of this plasmid was prepared and 30 ug were digested with HindIII (50 units) and BamHI (50 units). The 1.1 kb HindIII-BamHI fragment was purified by adsorption on glass beads (Vogelstein and Gillespie, 1979) after agarose gel electrophoresis. The purified fragment (0.5 ug) was added to 0.5 ug of the 2.9 kb HindIII-BamHI fragment of pBR327. After treatment with DNA ligase (20 units, 4 hours, 22° C.), the resulting plasmids were introduced to E. coli C600 cells. Clones resistant to ampicillin at 200 ug/ml were selected on solid media; 220 clones were obtained. Minipreps of plasmid DNA were made from six of these clones and tested with the presence of a 1.1 kb fragment after digestion with HindIII and BamHI. One plasmid which demonstrated the correct insert was designated pMON42. Plasmid pMON42 DNA was prepared as described in previous examples.

EXAMPLE 17

Creation of M13 Clone M-2

Seventy-five ug of plasmid pMON42 (described in Example 16) prepared from dam—E. coli cells were digested with RsaI and BamHI (50 units of each, 3 hours, 37° C.) and the 720 bp RsaI-BamHI fragment was purified using NA-45 membrane. Eight ug of the purified 720 bp BamHI-RsaI fragment were digested with MboI (10 minutes, 70° C.), the ends were made blunt by filling in with the large Klenow fragment of DNA polymerase I and the-four dNTP's. Then 0.1 ug of the resulting DNA mixture was added to 0.05 ug of M13 mp 8 previously digested with SmaI (1 unit, 1 hour 37° C.) and calf alkaline phosphatase (0.2 units). After ligation (10 units of T4 DNA ligase, 16 hours, 12° C.) and transfection of E. coli JM101 cells, several hundred recombinant phage were obtained. Duplex RF DNA was prepared from twelve recombinant, phage-carrying clones. The RF DNA (0.1 ug) was cleaved with EcoRI, (1 unit, 1 hour, 37° C.), end-labeled with $^{32}$P-dATP and Klenow polymerase, and re-digested with BamHI (1 unit, 1 hour, 37° C.). The EcoRI and BainHI sites span the SmaI site. Therefore, clones containing the 260 bp MboI fragment could be identified as yielding a labelled 270 bp fragment after electrophoresis on 6% poly-acrylamide gels and autoradiography. Four of the twelve clones carried this fragment. The orientation of the insert was determined by digestion of the EcoRI-cleaved, end-labeled RF DNA (0.1 ug) with HinfI (1 unit, 1 hour, 37° C.). HinfI cleaves the 260 by MboI fragment once 99 bp from the 3' end of the fragment and again 42 bp from the end nearest the NOS coding region. Two clones of each orientation were obtained. One clone, digested as M-2 as shown in FIG. 19, contained the 260 bp fragment with the EcoRI site at the 3' end of the fragment. M-2 RF DNA was prepared using the procedures of Messing, et al 1981.

EXAMPLE 18

Creation of pMON75 and pMON76

Fifty ug of M-2 RF DNA (described in Example 17) were digested with 50 units of EcoRI and 50 units of BamHI for 2 hours at 37°. The 270 bp fragment (1 ug) was purified using agarose gel and NA-45 membrane. Plasmid pMON58 (described in Example 4) was digested with EcoRI and BamHI (50 ug, 50 units each, 2 hours, 37° C.) and the 1300 bp fragment was purified using NA-45 membrane. The 270 bp EcoRI-BamHI (0.1 ug) and 1300 bp EcoRI-BamHI (0.5 ug) fragments were mixed, treated with T4 DNA ligase (2 units) for 12 hours at 14° C. After heating at 70° C. for 10 minutes to inactivate the ligase, the mixture was treated with EcoRI (10 units) for 1 hour at 37° C., then heated to 70° C. for 10 minutes to inactivate the EcoRI. This completed the assembly of a chimeric NOS-NPTII-NOS gene on a 1.6 kb fragment, as shown on FIG. 20.

Plasmid pMON38 is a clone of the pTiT37 HindIII-23 fragment inserted in the HindIII site of pBR327 (Soberon, et al 1980). pMON38 DNA (20 ug) was digested with EcoRI (20 units, 2 hours, 37° C.) and calf alkaline phosphatase (0.2 units, 1 hour, 37° C.) The pMON38 DNA reaction was extracted with phenol, precipitated with ethanol, dried and resuspended in 20 ul of 10 mM Tris-HCl, 1 mM EDTA, pH 8.

0.2 ug of the cleaved pMON38 DNA was added to the chimeric gene mixture described above. The mixture was treated with T4 DNA ligase (4 units, 1 hour, 22° C.) and mixed with Rb chloride-treated *E. coli* C600 recA56 cells to obtain transformation. After plating with selection for ampicillin-resistant (200 ug/ml) colonies, 63 potential candidates were obtained. Alkaline mini-preps of plasmid DNA were made from 12 of these and screened by restriction endonuclease digestion for the proper constructs. Plasmid DNA's that contained a 1.5 kb EcoRI fragment and a new BgII site were digested with BamHI to determine the orientation of the 1.5 kb EcoRI fragment. One of each insert orientation was picked. One plasmid was designated pMON75 and the other pMON76, as shown in FIG. 20. DNA from these plasmids were prepared as described in previous examples.

REFERENCES

A. Bale et al, *Mut. Res.* 59: 157 (1979)
F. Bolivar, *Gene* 4: 121 (1978)
A. Braun and H. Wood, *Proc. Natl. Acad. Sci. USA* 73: 496 (1976)
M. D. Chilton et al, *Cell* 11: 263 (1977)
A. Colman et al, *Eur. J. Biochem* 91: 303-310 (1978)
T. Currier and E. Nester, *J. Bact.* 126: 157 (1976)
M. Davey et al, *Plant Sci. Lett.* 18: 307 (1980)
R. W. Davis et al, *Advanced Bacterial Genetics* Cold Spring Harbor Laboratory, New York, (1980)
H. De Greve et al, *Plasmid* 6: 235 (1981)
G. Ditta et al, *Proc. Natl. Acad. Sci. USA* 77: 7347 (1980)
D. Garfinkel et al, *Cell* 27: 143 (1981)
S. Hasezawa et al, *Mol. Gen. Genet.* 182: 206 (1981)
J. Hernalsteens et al, *Nature* 287: 654 (1980)
D. Ish-Horowicz and J. F. Burke, *Nucleic Acids Res.* 9: 2989-2998 (1981)
B. Koekman et al, *J. Bacteriol.* 141: 129 (1979)
F. Krens et al, *Nature* 296: 72 (1982)
J. Leemans et al, *J. Mol. Appl. Genet.* 1: 149 (1981)
J. Leemans et al, *The EMBO J.* 1: 147 (1982)
A. L. Lehninger, *Biochemistry*, 2nd ed. (Worth Publ., 1975)
P. Lurquin, *Nucleic Acids. Res.* 6: 3773 (1979)
T. Maniatis et al, *Molecular Cloning, A Laboratory Manual* (Cold Spring Harbor Labs, 1982)
L. Marton et al, *Nature* 277: 129 (1979)
T. Matzke and M-D Chilton, *J. Mol. Appl. Genet.* 1: 39 (1981)
J. Messing et al, *Nucleic Acids Res.* 9: 309 (1981)
J. Messing and J. Vieira, *Gene* 19:.269-276 (1982)
J. Miller, *Experiments in Molecular Genetics*, Cold Spring Harbor Laboratory, N.Y. (1972)
N. Murray et al, *J. Mol. Biol.* 132: 493 (1979)
G. Ooms et al, *Plasmid* 7: 15 (1982)
L. Otten and R. Schilperoort, *Biochim. Biophys Acta* 527: 497 (1978)
L. Otten, *Mol. Gen. Genet.* 183: 209 (1981)
R. Roberts, *Nucleic Acids Res.* 10: r117 (1982)
A. Rorsch and R. Schilperoort, *Genetic Engineering*, 189 Elsevier/North Holland, N.Y. (1978)
J. K. Setlow and A. Hollaender, *Genetic Engineering, Principles and Methods* (Plenum Press 1979)
X. Soberon et al, *Gene* 9: 287 (1980)
L. Stryer, *Biochemistry*, 2nd. ed. (W. H. Freeman and Co., 1981)
M. Thomashow et al, *Cell* 19: 729 (1980)
B. Vogelstein and D. Gillespie, *Proc. Natl. Acad. Sci.:* 615-619 (1979)
L. Willmitzer et al, *Nature* 287: 359 (1980)
L. Willmitzer et al, *The EMBO J.* 1: 139 (1982)
N. Yadev et al, *Nature* 287: 1 (1980)
F. Yang et al, *Mol. Gen. Genet.* 177: 707 (1980)
P. Zambryski et al, *J. Mol. Appl. Genet.* 1:361 (1982)
S. Adams et al, Abstract #149, 183rd Meeting of the Amer. Chemical Society (1982)
N. Amrhein et al, *Plant Physiol.* 66: 830 (1980)
E Auerswald et al, *Cold Spr. Hbr. Symp. Quant. Biol.* 45: 107 (1981)
S. Beaucage and M. Carruthers, *Tetrahedron Lett.* 22: 1859 (1981)
E. Beck et al, *Gene* 19: 327 (1982)
J. Beggs, *Nature* 275: 104 (1978)
D. Berg et al, *Proc. Natl. Acad. Sci. USA* 76: 3628 (1975)
M. Capecchi, *Cell* 22: 479 (1980)
A. C. Y. Chang and S. U. Cohen, *J. Bacteriol.* 134: 1141-1156 (1978)
F. Colbece-Garapin, et al, *J. Mol. Biol.* 150:1-14 (1981)
Covey, S. N., G. P. Lomonosoff and R. Hull (1981) *Nucleic Acids Res.*, 9:6735-6747
T. Currier and E. Nester, *J. Bact.* 126: 157 (1976)
M. Davey et al, *Plant Sci. Lett.* 18: 307 (1980)
Dudley, R. et al., *Virology* 117:19 (1982)
R. Fischer and R. Goldberg, *Cell* 29: 651 (1982)
R. Fraley and D. Papahadjopoulos, *Current Topics in Microbiology and Immunology* 96: 171 (1981)

Fraley, R. T., R. B. Horsch, A. Matzke, M. D. Chilton, W. S. Chilton and P. R. Sanders, *Plant Molecular Biology* 3, 371-378 (1984)
Frank, A., H. Guilley, G. Joward, K. Richards and L. Hirth, *Cell* 21, 285-294 (1980)
Gardner, R. C. et al., *Nucleic Acids Research* Vol. 9, No. 12:287 (1981)
D. Garfinkel et al, *Cell* 27: 143 (1981)
L. Guarente, et al, *Science* 209: 1428-1430 (1980)
Howarth, A. S. et al., *Virology* 112:678 (1981)
J. Hyldig-Nielsen, *Nucleic Acids Res.* 10: 689 (1982)
K. Itakura, et al, *Science* 198: 1056-1063 (1977)
A. Jimenez and J. Davies, *Nature* 287: 869 (1980).
M. Kozak, *Cell* 15: 1109 (1978)
S. McKnight, *Cell* 31: 355 (1982)
J. Miller, *Experiments in Molecular Genetics*, Cold Spring Harbor Laboratory, N.Y. (1972)
J. Miller and W. Reznikof, *The Operon,* 2nd edition, Cold Spring Harbor Laboratory, New York (1982)
N. Murray et al, *J. Mol. Biol.* 132: 493 (1979)
H. Pederson et al, *Cell* 29: 1015 (1982)
A. Petit and J. Tempe, *Mol. Gen. Genet.* 167: 145 (1978)
J. Pittard and B. Wallace, *J. Bacteriol.* 91: 1494 (1966)
C. M. Radding, *Annu. Rev. Biochem.* 47: 847-880 (1978)
N. Rao and S. Rogers, *Gene* 7: 79 (1979)
M. Rassoulzadegan et al, *Nature* 295: 257 (1982)
T. Roberts et al, *Proc. Natl. Acad. Sci. USA* 76: 760 (1979)
K. Sakaguchi and M. Okanishi, *Molecular Breeding and Genetics of Applied Microorganisms*, Kodansha/Academic Press (1981)
D. Sciaky et al, *Plasmid* 1: 238 (1978)
D. Shah et al, *Proc. Natl. Acad. Sci. USA* 79: 1022 (1982)
T. Shibata et al, *Proc. Natl. Acad. Sci. USA* 76: 1638-1642 (1979)
P. Southern and P. Berg, *J. Mol. Appl. Gen.* 1: 327-341 (1982)
K. Struhl et al, *Proc. Natl. Acad. Sci. USA* 75: 1929 (1979)
L. Stryer, *Biochemistry,* 2nd edition (Freeman & Co., San Francisco, 1981)
J. Vieira and J. Messing, *Gene* 19: 259 (1982)
T.-K. Wong and E. Neumann, *Bioch. Biophys. Res. Comm.* 107: 584 (1982)
R. Woychik et al, *Nucleic Acids Res.* 10: 7197 (1982)

The invention claimed is:

1. A co-integrate Ti plasmid for use in transforming plant cells comprising a T-DNA region having the following elements, in sequence:
  (a) a first T-DNA border sequence;
  (b) a plant gene comprising a 5' promoter region from a gene which exists naturally in a plant cell or naturally enters a plant cell, a structural coding sequence encoding a polypeptide expressable in plant cells and a 3' non-translated region encoding a polyadenylation signal, said 5' promoter region and 3' non-translated region being operably linked to said structural coding sequence; and
  (c) a second T-DNA border sequence, wherein said T-DNA border sequences enable the transfer and incorporation of T-DNA into the genome of a plant cell and there are no plant tumorigenic genes between and including the two T-DNA border sequences which would render a transformed plant cell tumorous or incapable of regeneration into a morphologically normal plant.

2. A plasmid of claim 1 in which the plant gene functions as a selectable marker in transformed plant cells.

3. A plasmid of claim 2 in which the chimeric gene causes the plant cells to be antibiotic resistant.

4. A plasmid of claim 3 in which the chimeric gene expresses neomycin phosphotransferase.

5. A plasmid of claim 4 wherein the chimeric gene comprises a promoter derived from a plant gene.

6. A plasmid of claim 1 which is obtained by in vivo recombination between a plant tumor inducing plasmid and a chimeric plasmid comprising a gene which functions in plants comprising in sequence:
  (a) a region of homology which is capable of causing in vivo recombination of the chimeric plasmid with a plant tumor inducing plasmid of *Agrobacterium;*
  (b) a plant gene comprising a 5' promoter region from a gene which exists naturally in a plant cell or naturally enters a plant cell, a structural coding sequence encoding a polypeptide which functions in plant cells as a selectable marker and a 3' non-translated region encoding a polyadenylation signal, said promoter and 3' non-translated region being operably linked to said structural coding sequence; and
  (c) an *Agrobacterium* plasmid T-DNA border sequence which enables the transfer and incorporation of T-DNA into the genome of a plant cell;
  said chimeric plasmid containing no plant tumorigenic genes between and including the region of homology and the T-DNA border sequence.

7. A plasmid of claim 6 in which the plant tumor inducing plasmid is a wild-type Ti plasmid.

8. A plasmid of claim 6 in which the plant tumor inducing plasmid is a disarmed Ti plasmid in which the tumorigenic genes and T-DNA left border has been removed.

9. A co-integrate Ti plasmid for use in transforming plant cells having a first gene which functions as a selectable marker gene in bacteria and a T-DNA region comprising:
  (a) a first T-DNA border sequence;
  (b) a second gene which functions as a selectable marker gene in transformed plant cells;
  (c) a third gene which is expressed in plant cells; and
  (d) a second T-DNA border sequence; in which said T-DNA border sequences enable the transfer and incorporation of T-DNA into the genome of a plant cell and there are no plant tumorigenic genes between and including the two T-DNA border sequences.

10. The plasmid of claim 9 in which (c) functions as a scorable marker gene.

11. The plasmid of claim 9 in which (c) is a chimeric gene.

12. The plasmid of claim 9 created by a crossover event between a plant tumor inducing plasmid of *Agrobacterium* and a chimeric plasmid comprising a gene which functions in plants comprising in sequence:
  (a) a region of homology which is capable of causing in vivo recombination of the chimeric plasmid with a plant tumor inducing plasmid of *Agrobacterium;*
  (b) a plant gene comprising a 5' promoter region from a gene which exists naturally in a plant cell or naturally enters a plant cell, a structural coding sequence encoding a polypeptide which functions in plant cells as a selectable marker and a 3' non-translated region encoding a polyadenylation signal, said promoter and 3' non-translated region being operably linked to said structural coding sequence; and
  (c) an *Agrobacterium* plasmid T-DNA border sequence which enables the transfer and incorporation of T-DNA into the genome of a plant cell;
  said chimeric plasmid containing no plant tumorigenic genes between and including the region of homology and the T-DNA border sequence.

13. The plasmid of claim 9 in which the gene of (b) imparts to plant cells antibiotic resistance.

14. The plasmid of claim 13 in which the gene of (b) expresses neomycin phosphotransferase.

15. The plasmid of claim 9 which contains no tumorigenic genes.

16. A microorganism which contains a co-integrate plasmid of claim 1.

17. A microorganism which contains a co-integrate_plasmid of claim 9.

18. A microorganism which contains a co-integrate plasmid of claim 14.

19. A culture of microorganisms of claim 16.

20. A culture of microorganisms which contains a co-integrate Ti plasmid for use in transforming plant cells comprising a T-DNA region having the following elements, in sequence:
(a) a first T-DNA border sequence;
(b) a plant gene comprising a 5' promoter region from a gene which exists naturally in a plant cell or naturally enters a plant cell, a structural coding sequence encoding a polypeptide expressable in plant cells and a 3' non-translated region encoding a polyadenylation signal, said 5' promoter region and 3' non-translated region being operably linked to said structural coding sequence; and
(c) a second T-DNA border sequence,
wherein said T-DNA border sequences enable the transfer and incorporation of T-DNA into the genome of a plant cell and there are no plant tumorigenic genes between and including the two T-DNA border sequences which would render a transformed plant cell tumorous or incapable of regeneration into a morphologically normal plant, and wherein the culture of microorganisms is identified by ATCC number 39266.

21. The culture of microorganisms identified by ATCC number 39263.

* * * * *